US009862995B2

(12) United States Patent
Patel

(10) Patent No.: US 9,862,995 B2
(45) Date of Patent: Jan. 9, 2018

(54) MEASUREMENT OF NUCLEIC ACID VARIANTS USING HIGHLY-MULTIPLEXED ERROR-SUPPRESSED DEEP SEQUENCING

(71) Applicant: Abhijit Ajit Patel, Madison, CT (US)

(72) Inventor: Abhijit Ajit Patel, Madison, CT (US)

( * ) Notice: Subject to any disclaimer, the term of this patent is extended or adjusted under 35 U.S.C. 154(b) by 174 days.

(21) Appl. No.: 14/384,581

(22) PCT Filed: Mar. 13, 2013

(86) PCT No.: PCT/US2013/031014
§ 371 (c)(1),
(2) Date: Sep. 11, 2014

(87) PCT Pub. No.: WO2013/138510
PCT Pub. Date: Sep. 19, 2013

(65) Prior Publication Data
US 2015/0087535 A1   Mar. 26, 2015

Related U.S. Application Data

(60) Provisional application No. 61/609,985, filed on Mar. 13, 2012.

(51) Int. Cl.
*C12Q 1/68* (2006.01)
(52) U.S. Cl.
CPC ......... *C12Q 1/6853* (2013.01); *C12Q 1/6806* (2013.01); *C12Q 1/6858* (2013.01)
(58) Field of Classification Search
CPC ............ C12Q 1/6858; C12Q 2525/155; C12Q 2535/122; C12Q 2537/143; C12Q 2549/119; C12Q 1/6806; C12Q 1/6853; C12Q 2525/161; C12Q 2525/179; C12Q 2563/131; C12Q 2563/179
See application file for complete search history.

(56) References Cited

U.S. PATENT DOCUMENTS

| | | | |
|---|---|---|---|
| 5,846,719 A | 12/1998 | Brenner et al. | |
| 6,172,214 B1 | 1/2001 | Brenner | |
| 7,622,281 B2 * | 11/2009 | Ronaghi | C12Q 1/6874 435/6.14 |
| 7,824,889 B2 | 11/2010 | Vogelstein et al. | |
| 7,935,487 B2 | 5/2011 | Gocke et al. | |
| 8,168,385 B2 | 5/2012 | Brenner | |
| 8,361,726 B2 | 1/2013 | Gocke et al. | |
| 8,470,996 B2 | 6/2013 | Brenner | |
| 8,481,292 B2 | 7/2013 | Casbon et al. | |
| 8,835,358 B2 | 9/2014 | Fodor et al. | |
| 2003/0207300 A1 | 11/2003 | Matray | |
| 2005/0250147 A1 | 11/2005 | Macevicz | |
| 2007/0172873 A1 | 7/2007 | Brenner | |
| 2013/0005585 A1 * | 1/2013 | Anderson | C12N 15/10 506/2 |
| 2013/0040824 A1 | 2/2013 | Lo et al. | |

FOREIGN PATENT DOCUMENTS

| | | | |
|---|---|---|---|
| WO | WO9813522 | * | 2/1998 |
| WO | 2005080604 | A2 | 9/2005 |
| WO | 2005111242 | A2 | 11/2005 |
| WO | 2009036525 | A2 | 3/2009 |
| WO | 2011091046 | A1 | 7/2011 |
| WO | 2012028746 | A1 | 3/2012 |
| WO | 2012142213 | A2 | 10/2012 |
| WO | 2013142389 | A1 | 9/2013 |

OTHER PUBLICATIONS

Bybee et al., Genome Biol. Evol. 3:1312-1323, Oct. 13, 2011.*
International Search Report of PCT/US2013/031014 dated Jun. 25, 2013.
Schmitt et al., "Detection of Ultra-Rare Mutations by Next-Generation Sequencing," Proceedings of the National Academy of Sciences, vol. 109, No. 36, pp. 14508-14513 (2012).
Narayan et al., "Ultrasensitive Measurement of Hotspot Mutations in Tumor DNA in Blood Using Error-Suppressed Multiplexed Deep Sequencing," Cancer Research, vol. 72, No. 14, pp. 3492-3498 (2012).
Casbon, et al.: A method for counting PCR template molecules with application to next-generation sequencing. Nucleic Acids Res Jul, 2011, 39:e81, doi: 10.1093/nar/gkr217.
Craig, et al.: Identification of genetic variants using bar-coded multiplexed sequencing. Nat Methods Oct, 2008, 5:887-893, doi: 10.1038/nmeth.1251.
D'Antoni, et al.: Rapid quantitative analysis using a single molecule counting approach. Anal Biochem May 1, 2006, 352:97-109, doi: 10.1016/j.ab.2006.01.031.
Flaherty, et al.: Ultrasensitive detection of rare mutations using next-generation targeted resequencing. Nucleic Acids Res Jan. 2012, 40:e2, doi: 10.1093/nar/gkr861.
Fu, et al.: Counting individual DNA molecules by the stochastic attachment of diverse labels. Proc Natl Acad Sci U S A May 31, 2011, 108:9026-9031, doi: 10.1073/pnas.1017621108.
Hamady, et al.: Error-correcting barcoded primers for pyrosequencing hundreds of samples in multiplex. Nat Methods Mar. 2008, 5:235-237, doi: 10.1038/nmeth.1184.
Jabara, et al.: Accurate sampling and deep sequencing of the HIV-1 protease gene using a Primer ID. Proc Natl Acad Sci U S A Dec. 13, 2011, 108:20166-20171, doi: 10.1073/pnas.1110064108.
Kinde, et al.: Detection and quantification of rare mutations with massively parallel sequencing. Proc Natl Acad Sci U S A Jun. 7, 2011, 108:9530-9535, doi: 10.1073/pnas.1105422108.
Kivioja, et al.: Counting absolute numbers ff molecules using unique molecular identifiers. Nat Methods Nov 20, 2011, 9:72-74, doi: 10.1038/nmeth.1778.
Leary, et al.: Development of personalized tumor biomarkers using massively parallel sequencing. Sci Transl Med Feb. 24, 2010, 2:20ra14, doi: 10.1126/scitranslmed.3000702.
Li, et al.: Mapping short DNA sequencing reads and calling variants using mapping quality scores. Genome Res Nov. 2008, 18:1851-1858, doi: 10.1101/gr.078212.108.

(Continued)

*Primary Examiner* — Cynthia B Wilder
(74) *Attorney, Agent, or Firm* — Barnes & Thornburg LLP

(57) ABSTRACT

Methods and compositions are disclosed for measuring low-abundance DNA variants from a complex mixture of DNA molecules. Embodiments of the methods allow for extremely sensitive detection and can distinguish true variants from sequencer misreads and PCR misincorporations.

14 Claims, 18 Drawing Sheets

(56) References Cited

OTHER PUBLICATIONS

McCloskey, et al.: Encoding PCR products with batch-stamps and barcodes. Biochem Genet Dec, 2007, 45:761-767 doi: 10.1007/s10528-007-9114-x.

Smith, et al.: Highly-multiplexed barcode sequencing: an efficient method for parallel analysis of pooled samples. Nucleic Acids Res Jul, 2010, 38:e142, doi: 10.1093/nar/gkq368.

Varley, et al.: Nested Patch PCR enables highly multiplexed mutation discovery in candidate genes. Genome Res Nov. 2008, 18:1844-1850, doi: 10.1101/gr.078204.108.

\* cited by examiner

Figure 2 Combining modular oligonucleotide segments

Primer mixtures for samples 1 and 2 contain identical ratios of multiple gene-specific sequences. Each mixture has a distinct sample-specific barcode.

Figure 4
A
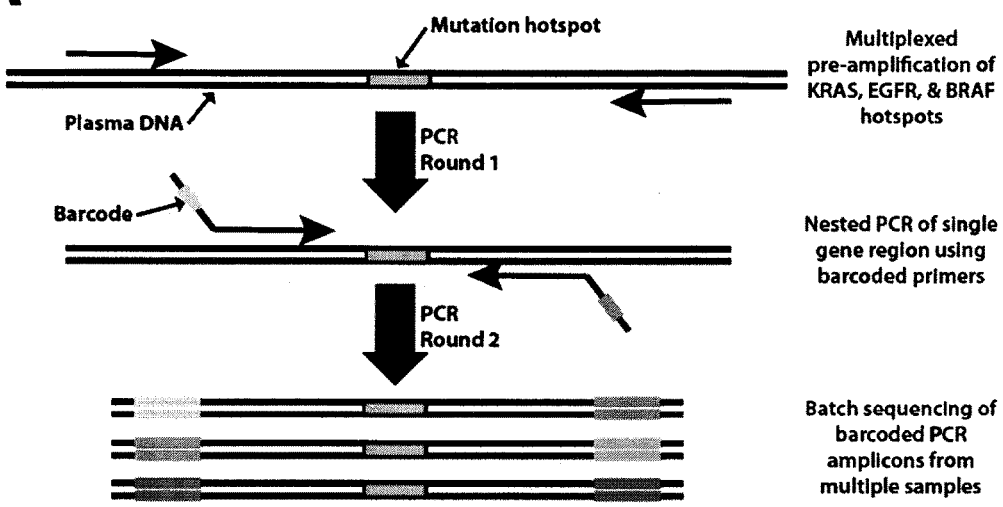
B
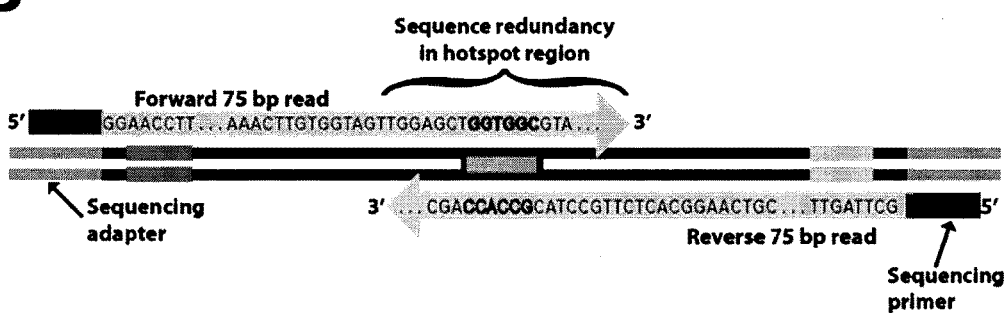

Ratio of DNA added (mutant : wild-type)

Figure 7
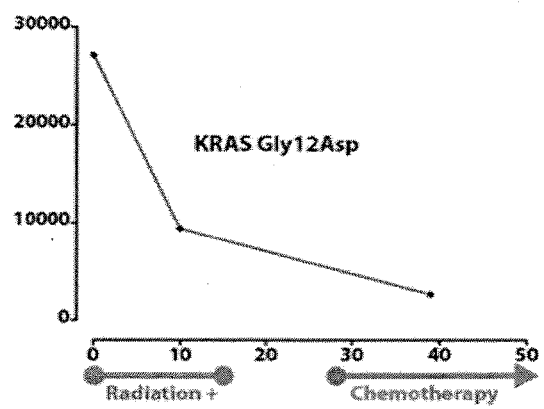
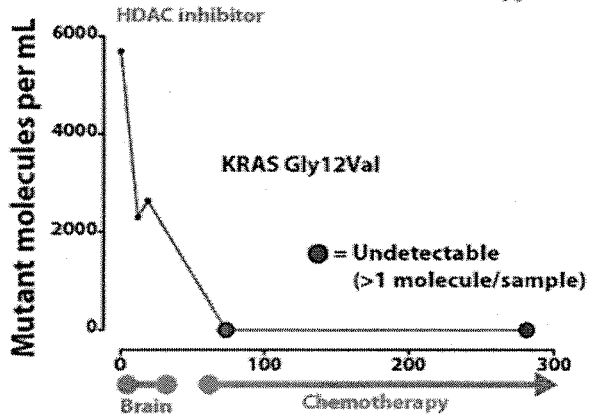
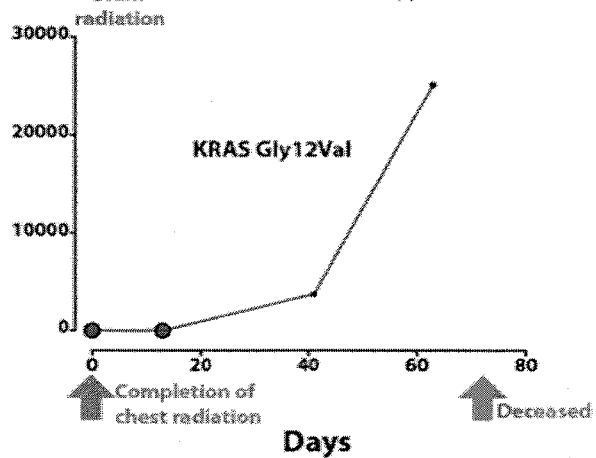

Figure 10 Schematic of process described in Example 2

Figure 11    Workflow of process described in Example 2

N = degenerate sequence position at which there is an approximately equal probability of an A, C, G, or T being present.

Figure 13 Schematic of splint-mediated ligation of modular oligonucleotides
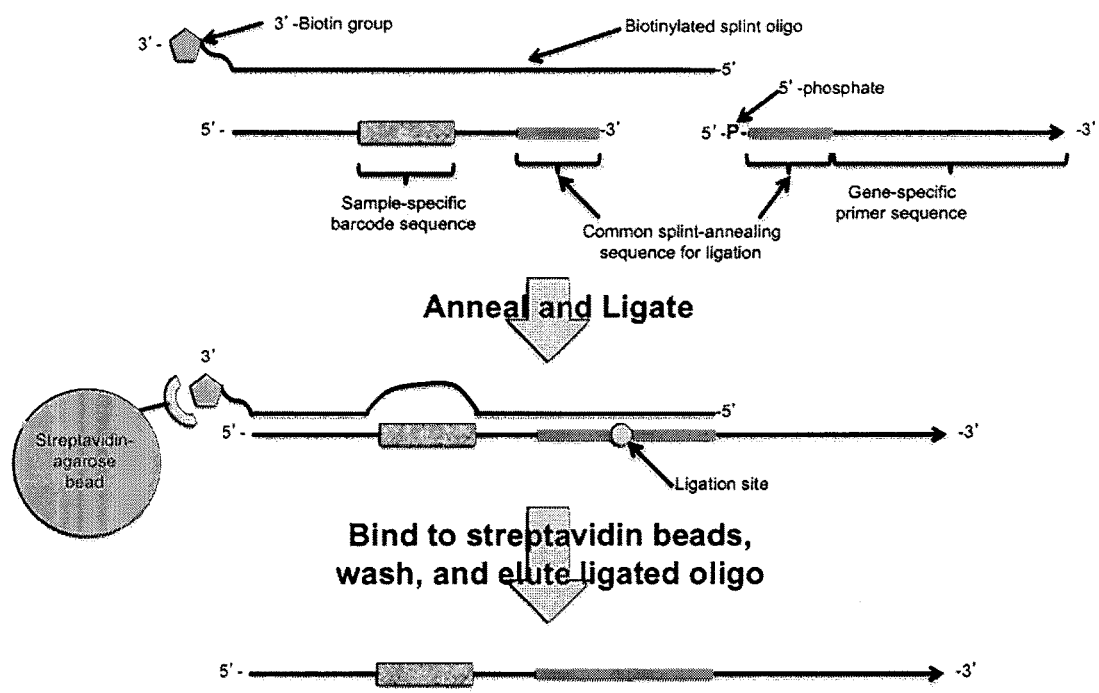

Figure 14

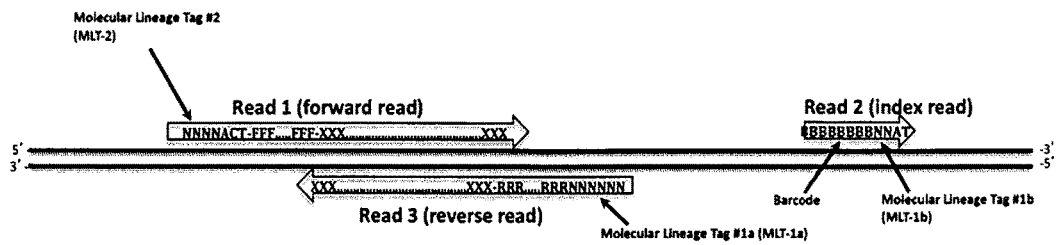

X= amplicon target region (area to be analyzed for presence of mutations)
F= forward primer sequence
R= reverse primer sequence
B= barcode sequence (specifies the sample of origin)
N= Degenerate sequence (equal probability of A,C, G, or T at each position; allows tracking of molecular lineage;
   also promotes more accurate cluster discrimination during Illumina sequencing).
Note: MLT-1 is created by concatenating the sequences of MLT-1a and MLT-1b
Note: In Example 3, the sequence "NNNNACT" in the region of MLT-2 is replaced by "NNNNNN"

Molecular Lineage Tags permit variants derived from true mutant template molecules to be distinguished from errors of sequencing or amplification; they also serve to minimize misclassification of molecules caused by replacement of barcodes during multiplexed amplification.

Figure 15

```
Gene Segment: TP53-1
Sample Barcode: 36
Total clones in bin: 58378
Exact matches to Wild-type: 51246
Consistent variants: 2395
Inconsistent variants: 4737

Mismatch Table:
Pos:                    *       -       +       #A|#C|#G|#T     A       C       G       T
1:A     58372   3       1       0       00|00|00|00     0       2       0       0
2:C     58294   53      4       1       00|00|01|00     2       0       23      1
3:C     58376   2       0       0       00|00|00|00     0       0       0       0
4:C     58320   43      5       0       00|00|00|00     5       0       3       2
5:C     58370   6       0       0       00|00|00|00     1       0       1       0
etc...

Consistent variants:                                                    Multiply occurring MLTs: (count of MLTs occurring N times)
        ACCCCCGCCCGGCACCCGCGTCCGCGCCATGGCCATCTA [SEQ ID NO: 339]   N: 15 | 14 | 13 | 12 | 11 | 10 | 09 | 08 | 07 | 06 | 05 | 04 | 03 | 02 | Total
167     -A------------------------------------- [SEQ ID NO: 340]      0    0    0    0    0    0    0    0    0    0    0    0    0    0    0
145     --------------------------------------- [SEQ ID NO: 341]      0    0    0    0    0    0    0    0    0    0    0    0    0    1    1
120     --------------------------------------- [SEQ ID NO: 342]      0    0    0    0    0    0    0    0    0    0    0    0    0    0    0
113     T-------------------------------------- [SEQ ID NO: 343]      0    0    0    0    0    0    0    0    0    0    0    0    0    2    2
96      --------------------------------------- [SEQ ID NO: 344]      0    0    0    0    0    0    0    0    0    0    0    0    0    0    0
84      ----G-----------------------------A---- [SEQ ID NO: 345]      0    0    0    0    0    0    0    3    6    2    0    0    0    0    11
81      --------------------------------------- [SEQ ID NO: 346]      0    0    0    0    0    0    0    0    0    0    0    0    0    0    0
etc...
```

•Mismatches to the wild-type reference sequence are indicated by:
  •A "*" if the mismatch is found in a read from one strand, but not confirmed by the read from the opposite strand.
  •A "-" if the mismatch is a deletion that is confirmed by overlapping paired-end reads.
  •A "+" if the mismatch is an insertion that is confirmed by overlapping paired-end reads (the inserted nucleotides counts are listed under #A, #C, #G, or #D).
  •An "A" if the mismatch is a point mutation in which the nucleotide is replaced by an "A" and has been confirmed by overlapping paired-end reads.
  •A "C" if the mismatch is a point mutation in which the nucleotide is replaced by a "C" and has been confirmed by overlapping paired-end reads.
  •A "G" if the mismatch is a point mutation in which the nucleotide is replaced by a "G" and has been confirmed by overlapping paired-end reads.
  •A "T" if the mismatch is a point mutation in which the nucleotide is replaced by a "T" and has been confirmed by overlapping paired-end reads.

•Variant sequences that are likely to be arising from mutant template DNA molecules rather than from errors of amplification or sequencing are boldfaced.

Figure 16. Example of processed data for BRAF target region

Figure 18

[Figure contains low-resolution tabular data that is largely illegible]

MEASUREMENT OF NUCLEIC ACID VARIANTS USING HIGHLY-MULTIPLEXED ERROR-SUPPRESSED DEEP SEQUENCING

GOVERNMENTAL INTERESTS

The research leading to this application was funded by the National Institutes of Health from grant RR014139. The government has certain rights in this invention.

BACKGROUND

Tumor-derived DNA is released into the bloodstream from dying cancer cells in patients with various types of malignancies. Such circulating tumor DNA (ctDNA) is showing excellent promise as a non-invasive cancer biomarker. However, an assay that is capable of exploiting ctDNA for early cancer detection presents several challenges. In the bloodstream, ctDNA can be distinguished from normal background DNA based on the presence of tumor-specific mutations. However, mutant ctDNA is usually only present in small amounts, having been previously reported to comprise an average of 0.2% of total plasma DNA (Diehl et al., *Nat Med.* 2008; 14: 985-990). If variant DNA sequences are low in abundance, detecting and quantifying these variants can be more challenging. Small amounts of mutation-harboring ctDNA can be obscured by a relative excess of background wild-type plasma DNA. Thus, an assay with extremely high detection sensitivity is required.

There is a need for a method that is able to detect and quantify rare variant sequences to detect cancers in situations where the amount of DNA in a given sample is limited. Unlike existing approaches, a test should be able to evaluate an entire panel of mutation-prone regions without needing to divide DNA samples into separate reactions (which could reduce detection sensitivity by providing fewer template DNA copies per reaction). Methods and compositions are described herein that provide a multiplex assay to detect minute amounts of ctDNA and address the current deficiencies to assay ctDNA.

SUMMARY

Described herein are compositions and methods relating to next-generation sequencing and medical diagnostics. Methods include identifying and quantifying nucleic acid variants, particularly those available in low abundance or those obscured by an abundance of wild-type sequences. Also described herein are methods related to identifying and quantifying specific sequences from a plurality of sequences amid a plurality of samples. Methods as described herein also include detecting and distinguishing true nucleic acid variants from misincorporation errors, sequencer errors, and sample misclassification errors. Methods include early attachment of barcodes and molecular lineage tags (MLTs) to targeted nucleic acids within a sample. Methods also include clonal overlapping paired-end sequencing to achieve sequence redundancy.

In an embodiment, a method includes measuring nucleic acid variants by tagging and amplifying low abundance template nucleic acids in a multiplexed primer extension or PCR. Low abundance template nucleic acids may be fetal DNA, circulating tumor DNA (ctDNA), viral RNA, viral DNA, DNA from a rejected transplanted organ, or bacterial DNA. A multiplex PCR may include gene specific primers, wherein primers are specific for a mutation prone region (e.g., within KRAS, EGFR, etc.). In an embodiment, a mutation prone region may be associated with cancer. As disclosed herein, a multiplex PCR can include more than one round of PCR and/or primer-extension. In an embodiment, a multiplex PCR can include two or three rounds of PCR.

In an embodiment, primers comprise a barcode and/or a molecular lineage tag (MLT). In an embodiment, a MLT can be 2-10 nucleotides. In another embodiment, a MLT can be 6, 7, or 8 nucleotides. In an embodiment, a barcode can identify the sample of template nucleic acid. In an embodiment, a PCR reaction mixture includes template nucleic acids from multiple samples (e.g., patients), wherein the barcode identifies the sample origin of the template nucleic acid. In an embodiment, a primer extension reaction employs targeted early barcoding. In targeted early barcoding, a plurality of different primers specific for different nucleic acid regions all have an identical barcode. An identical barcode identifies the nucleic acids from a particular sample. In an embodiment, primers used for targeted early barcoding are produced by combining a unique barcode-containing oligonucleotide segment with a uniform mixture of gene-specific primer segments in a modular fashion.

In an embodiment, multiplex assays described herein can be used for clinical purposes. In an embodiment, nucleic acid variants within blood can be identified and measured before and after treatment. In an example of cancer, a nucleic acid variant (e.g., cancer-related mutation) can be identified and/or measured prior to treatment (e.g., chemotherapy, radiation therapy, surgery, biologic therapy, combinations thereof). Then after treatment, the same nucleic acid variant can be identified or measured. After treatment, a decrease or absence of the nucleic acid variant can indicate that the therapy was successful.

BRIEF DESCRIPTION OF THE DRAWINGS

FIG. 4A and FIG. 4B are schematics of error-suppressed multiplexed deep sequencing. FIG. 4A shows cell-free DNA purified from plasma undergoing two rounds of amplification by PCR. The first round amplifies mutation hotspot regions of several genes from a given sample in a single tube. The second round separately amplifies each hotspot region using nested primers incorporating unique combinations of barcodes to label distinct samples. The barcoded PCR products are then pooled and subjected to deep sequencing. Millions of sequences are sorted and counted to determine the ratio of mutant to wild-type molecules derived from each sample. The total number of plasma DNA fragments is measured by real-time PCR and can be used to calculate the absolute concentration of mutant ctDNA. FIG. 4B shows sequence redundancy in mutation hotspot regions is produced by partial overlap of paired-end reads from the forward and reverse strands of each clone. This yields highly accurate base-calls, permitting detection and quantitation of rare mutations with greater sensitivity.

FIG. 5A shows filtered reads from one end of the amplicon have relatively frequent mismatches when directly compared to the wild-type sequence. Data from 3 replicate amplifications are shown. FIG. 5B indicates sequencer errors are greatly reduced by requiring both partially overlapping paired-end reads from each clone to exactly match a specific mutation. The Gly12Ser mutation is now readily distinguished from the remaining low-level errors that were likely introduced during DNA amplification and processing. Insertions and deletions are no longer seen in this region after requiring agreement of overlapped reads. FIG. 5C shows a further reduction in the relative error level can be achieved by calculating the mean values of 3 replicate measurements, since mutations found in the original DNA sample should produce more consistent counts than randomly occurring errors.

FIG. 6A is a linear plot of DNA from the KRAS-mutant cell line over the range of concentrations tested. FIG. 6B and FIG. 6C show that BRAF- and EGFR-mutant lines, respectively, contained a small amount of wild-type DNA, thereby yielding a plateau at higher mutant to wild-type ratios. Non-linear least-squares fits were performed using the equation $y=10^{\wedge}(slope*log((1-C)*x/(C*x+1))+intercept)$ where C was the fraction of wild-type molecules found in DNA extracted from mutant cell lines. Error bars indicate the standard deviation of 3 measurements.

FIGS. 7A-C show the changes in ctDNA levels with treatment or disease progression. Measurements of mutant ctDNA from patients with NSCLC are shown at various times in relation to therapeutic interventions and disease status. ctDNA was considered undetectable if sequence counts yielded a quantity of less than one mutant molecule per sample. Median genome equivalents per sample, as determined by real-time PCR were 9602 (IQR=5412-11513) FIG. 7A shows the timeline of treatment for Patient 3 who had stage IV lung adenocarcinoma with a 4.3 cm right upper lobe tumor and large metastases in the abdomen and supraclavicular region. She was treated concurrently with an experimental histone deacetylase (HDAC) inhibitor and palliative radiation therapy directed at her painful 6.9 cm supraclavicular lesion. She began chemotherapy treatment shortly afterwards. FIG. 7B shows the timeline of treatment for Patient 5 who had a 7.5 cm lung adenocarcinoma with eight small brain metastases ranging from 3 mm to 15 mm in size at presentation. He was treated with palliative whole-brain radiation therapy, followed by long-term weekly chemotherapy. Follow-up imaging revealed an excellent, durable response with shrinkage of the lung tumor to ~15% of its original volume at 7 months after diagnosis. No evidence of disease progression was seen during this time period. FIG. 7C shows the timeline of treatment for Patient 9 who underwent definitive radiation treatment for locally advanced, stage IIIB undifferentiated NSCLC. Other health conditions prevented him from undergoing surgery or concurrent chemotherapy. Blood sample collection commenced upon completion of his treatment. Although his disease was confined to the thorax prior to initiating radiation therapy, a PET scan performed 8 weeks after treatment showed marked progression of disease with multiple osseous, hepatic, and subcutaneous metastases. He expired 10 weeks after completing treatment.

FIG. 8A shows the timeline of treatment for Patient 11 who had stage IV lung adenocarcinoma with widespread metastatic disease in the bones of her spine, ribs, sternum, clavicle, humerus, and pelvis. She was treated with a short course of palliative radiation therapy for a pathologic fracture in her lumbar spine. A single blood sample was obtained on her last day of treatment. She passed away approximately 1 week after completion of therapy. FIG. 8B shows the timeline of treatment for Patient 14 who had stage IV lung adenocarcinoma. He received palliative radiation therapy to a painful 8.9×5.9×4.9 cm lesion in his left posterior chest wall, given concurrently with an experimental histone deacetylase (HDAC) inhibitor. He had additional metastatic lesions in his liver, kidneys, and peri-splenic region. He was hospitalized for profound weakness 10 days post-treatment, and expired shortly afterwards. FIG. 8C shows the timeline of treatment for Patient 15 who had stage IV undifferentiated NSCLC with metastasis in the supraclavicular and inguinal regions, as well as several small tumors in his brain. His brain lesions were treated with single-fraction stereotactic radiosurgery. He then began palliative radiation therapy for a painful 7.1 cm left upper lobe lung mass, which was threatening to obstruct his left mainstem bronchus. He received concurrent treatment with a HDAC inhibitor as part of a clinical trial. He passed away unexpectedly after receiving 8 of 10 planned radiation treatments.

FIG. 13 is a schematic of a process of splint-mediated ligation of modular oligonucleotide segments. A 5'-segment containing a particular barcode sequence can be ligated to a mixture of 3'-segments having a variety of gene-specific primer sequences using a biotinylated splint oligonucleotide. Hybridization to the splint oligonucleotide is mediated by common annealing sequences. A 5'-phosphate is necessary on the 3'-segments to permit enzymatic ligation. The biotinylated splint can be used to capture and wash and elute the ligated products.

FIG. 14 shows elements of a sequence output using the Illumina® platform. Read 1 and read 3 are from opposite strands, and provide sequence redundancy via overlap in the mutation-prone region. This clonal redundancy allowed sequences resulting from sequencer errors to be identified and discarded, permitting greater sensitivity for detection of rare sequence variants.

FIG. 15 shows hypothetical processing of data from sequences assigned to a single gene and a single barcode. The example illustrates how analysis of variant sequences and associated molecular lineage tags can be performed.

FIG. 16 shows processed data from sequences generated using methods described in Example 2. Data are shown for a single gene and a single barcode. Symbols used in the mismatch table are as defined in FIG. 15. MLT counts associated with variant sequences are displayed in the format "N×Z" where N is the number of copies of a particular MLT sequence, and Z is the number of different MLT sequences having N copies.

FIG. 18 shows processed data from sequences generated from the methods described in Example 3. Data are shown for a single gene and a single barcode. Results are displayed in a format similar to FIG. 15, but in this case analysis of two separate MLT sequence regions (MLT-1 and MLT-2) was performed for variant and wild-type sequences. To report these counts in a succinct format, MLT counts are binned by powers of two. For example, an MLT-1 count of 13 would be placed into bin 4 (because 2^4 is the smallest power of 2 that is greater than or equal to 13). Thus, a report of 4×5 means that there were five instances of counts in the range of 9 to 16. Similarly, a report of 3×6 means that there were six instances of counts in the range of 5 to 8. For a given collection of MLT-1 counts, the associated MLT-2 counts were reported in a similar format, to the right of the MLT-1 counts and separated by colons. For example, 4×5:2×3:1×7 meant that among 5 sets of MLT-1 sequences occurring between 9 and 16 times, there were 3 instances of MLT-2 sequences that occurred between 3 and 4 times, and 7 instances of MLT-2 sequences that occurred twice. Different MLT-1 bins were separated by a space.

DETAILED DESCRIPTION

Definitions

Figure 1:
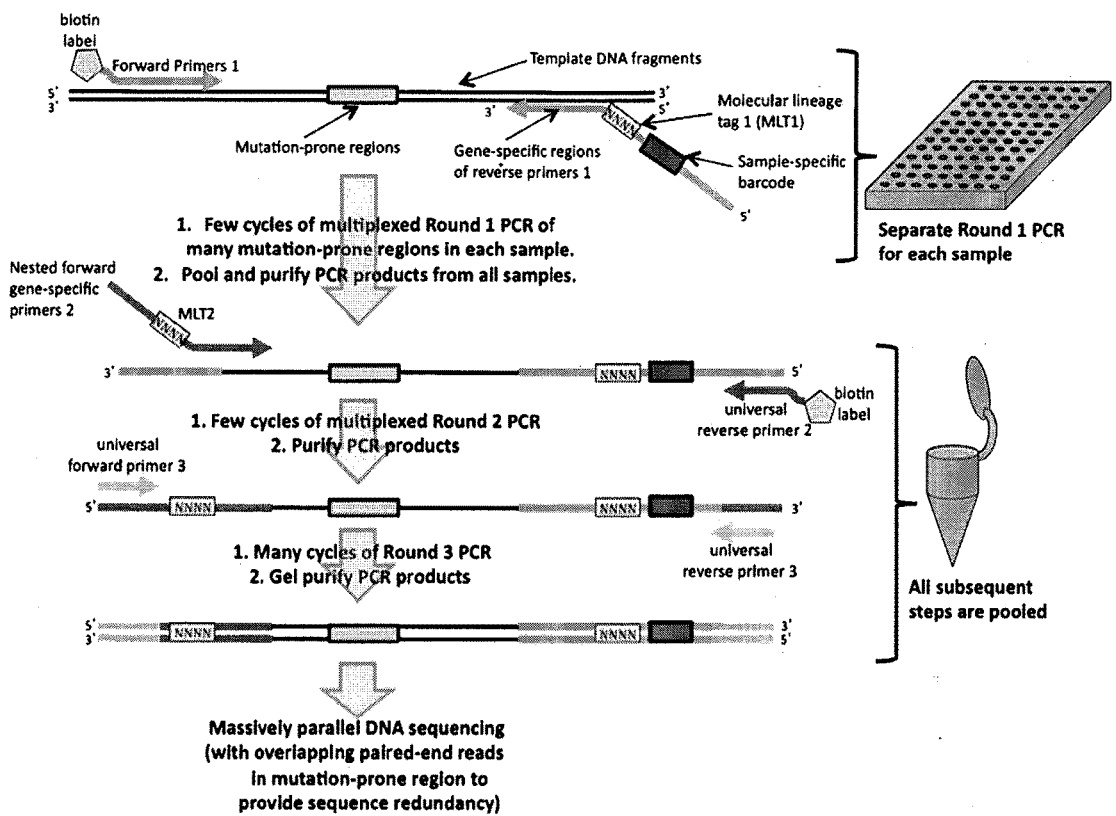
FIG. 1 is a schematic of a copying, tagging, amplification, and sequencing process. Two rounds of limited-cycle PCR were performed to attach barcode sequences and molecular lineage tag sequences to copies of targeted template DNA fragments. Stringent purification of the PCR products was carried out between rounds in order to remove unextended primers, spurious extension products, and template DNA. A final round of PCR was performed using universal primers to further amplify the purified products from Round 2. Final amplification products were gel-purified and subjected to clonal overlapping paired-end massively parallel sequencing. Use of primers synthesized from modular segments allowed early barcoding of targeted template DNA during the first round of PCR, enabling subsequent steps to be performed in a combined reaction volume.

The terms "nucleic acid," "nucleotide," "polynucleotide," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "base", in its singular form, refers to a single residue within a nucleic acid molecule or to a single position within a nucleic acid sequence read.

The term "biological sample" refers to a body sample from any animal, but preferably is from a mammal, more preferably from a human. Such samples include biological fluids such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, and cellular extracts.

As used herein, "buffer" refers to a buffered solution that resists changes in pH by the action of its acid-base conjugate components. Buffers may optionally comprise a salt such as $MgCl_2$, $MnCl_2$, or the like. Buffers may also optionally comprise other constituents to improve the efficiency of reverse transcription or amplification, including, but not limited to, betaine, dimethyl sulfoxide, surfactant, bovine serum albumin, etc.

The term "cDNA" refers to a complementary DNA molecule synthesized using a ribonucleic acid strand (RNA) as a template. RNA may be mRNA, tRNA, rRNA, microRNA, or another form of RNA, such as viral RNA. The cDNA may be single-stranded, double-stranded or may be hydrogen-bonded to a complementary RNA molecule as in an RNA/cDNA hybrid.

The term "polymerase chain reaction" or "PCR" refers to a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51:263 (1987); Erlich, ed., PCR Technology, (Stockton Press, NY, 1989).

The term "reverse transcription polymerase chain reaction" or "RT-PCR" refers to the transcription of cDNA from a RNA template by the enzyme reverse transcriptase. The cDNA is then amplified by known PCR methods.

The term "primer-extension" refers to an enzymatic process whereby a primer is hybridized to a template nucleic acid strand and is polymerized using said strand as a template. Polymerization can be mediated by enzyme classes including but not limited to DNA polymerases or reverse transcriptases. Primer-extension can take place as an isolated reaction (single extension of a primer on a template), or as part of a repetitive process such as PCR.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates (dNTPs) and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized. A primer can have some sequences that are not designed to hybridize to the targeted template DNA, including sequences at the 5'-end of the primer that becomes incorporated into the amplified products. Such sequences can include universal primer binding sites to be used in subsequent amplifications, sample-specific barcodes, or molecular lineage tags. In addition to serving the purpose of copying a nucleic acid template, a primer can also be used to append labels or other sequences to the copied products. Primers and other synthetic oligonucleotides disclosed herein have undergone either polyacrylamide gel purification or reverse-phase cartridge purification unless otherwise specified. A primer can also be modified by attachment of one or more chemical moieties including but not limited to biotin, a fluorescent tag, a phosphate, or a chemically reactive group.

The term "gene-specific primer" refers to a primer that is designed to hybridize to and be extended on a particular nucleic acid target. The 3'-segment of a gene-specific primer is complementary to its targeted RNA or DNA sequence, but other portions of the primer need not be complementary to any target. The target need not be a "gene" in the strict sense of the word. Possible targets include but are not limited to genomic DNA, mitochondrial DNA, viral DNA, mRNA, microRNA, viral RNA, tRNA, rRNA, and cDNA.

The term "nested primer" refers to a primer that is designed to hybridize to a primer-extended or PCR amplified product at a position that is either entirely or partially within the target region that was flanked by the original primers. The 3'-end of a nested primer is complementary to target sequences that would not have been contained within the original primers, but rather would have been copied by extension of the original primers on the desired template. Nested primers thus provide additional specificity for copying or amplifying a desired target after an initial round of primer-extension or PCR.

The terms "reaction mixture" or "PCR reaction mixture" or "PCR master mix" refer to an aqueous solution of constituents in a PCR or RT-PCR reaction that can be constant across different reactions. An exemplary PCR reaction mixture includes buffer, a mixture of deoxyribonucleoside triphosphates, reverse transcriptase, primers, probes, and DNA polymerase. Generally, template DNA is the variable in a PCR reaction.

The terms "sequence variant" or "mutation" are used interchangeably and refer to any variation in a nucleic acid sequence including but not limited to single point-mutations, multiple point-mutations, insertions/deletions (indels), and single-nucleotide polymorphisms (SNPs). These terms are used interchangeably in this document, and it is understood that when reference is made to a method for evaluating one type of variant, it could be equally applied to evaluation of any other type of variant. The term "variant" can also be used to refer to a single molecule whose sequence deviates from a reference sequence, or a collection of molecules whose sequences all deviate from the reference sequence in the same way. Similarly, "variant" can refer to a single sequence (or read) that deviates from a reference sequence or a set of sequences that deviate from a reference sequence.

The terms "mutation-prone region" and "mutation hotspot" are used interchangeably, and refer to a sequence region of a nucleic acid obtained from a biological source that has a higher probability of being mutated than surrounding sequence regions within the same nucleic acid. In the case of tumor-derived DNA, mutation-prone regions can be found in certain cancer-related genes. The mutation-prone region can be of any length, but mutation-prone regions that are analyzed using the methods disclosed herein are less than 100 nucleotides long. A mutation can be found anywhere within a mutation-prone region.

The term "target region" refers to a region of a nucleic acid that is targeted for primer extension or PCR amplification by specific hybridization of complementary primers.

The term "clonal overlapping paired-end sequencing" refers to a massively parallel sequencing method in which paired-end reads are obtained for each clonal sequence such that portions of the two reads from opposite strands are able to cover the same region of DNA. This approach is used to reduce or suppress or distinguish sequencer-derived errors, thereby allowing base-calls to be made with greater confidence. The region of DNA that is covered by the overlapping reads is effectively read twice in opposite directions, once from each strand of the duplex. Thus, by including the mutation-prone region within the area of sequence overlap, the mutation prone region is read in one direction and then proofread in the opposite direction. Read-pairs that do not have perfect sequence consistency in the overlapping region (after obtaining a reverse-complement of one of the reads) can be attributed to sequencer error and can be discarded from the analysis. This approach greatly reduces the background of sequencer-generated errors and allows rare mutant molecules to be detected with greater sensitivity.

The terms "barcode", "tag", and "index" are used interchangeably and refer to a sequence of bases at certain positions within an oligonucleotide that is used to identify a nucleic acid molecule as belonging to a particular group. A barcode is often used to identify molecules belonging to a certain sample when molecules from several samples are combined for processing or sequencing in a multiplexed fashion. A barcode can be any length, but is usually between 6 and 12 bases long (need not be consecutive bases). Barcodes are usually artificial sequences that are chosen to produce a barcode set, such that each member of the set can be reliably distinguished from every other member of the set. Various strategies have been used to produce barcode sets. One strategy is to design each barcode so that it differs from every other barcode in the set at a minimum of 2 distinct positions.

The term "sample-specific barcode" refers to a barcode sequence that is assigned to molecules that are derived from a particular sample.

The term "template nucleic acid" refers to any nucleic acids that can serve as targets for primer-extension, reverse-transcription, or PCR. A template nucleic acid can be DNA or RNA. Methods described herein for analysis of DNA can also be applied to the analysis of RNA after reverse-transcribing the RNA to produce cDNA. Methods for evaluating DNA can be equally applied to the evaluation of RNA.

The terms "deep sequencing" and "ultra-deep sequencing" are used interchangeably herein and refer to approaches that use massively parallel sequencing technologies to obtain large numbers of sequences corresponding to relatively short, targeted regions of the genome. A targeted region can include, for example, an entire gene or small segment of a gene (such as a mutation hotspot). In some cases, many thousands of clonal sequences are obtained from a short targeted segment allowing identification and quantitation of sequence variants.

The term "clonal sequence" refers to a sequence that is derived from a single molecule within a sample that is subjected to massively parallel sequencing. Specifically, each clonal sequence that is generated by massively parallel sequencing is derived from a distinct DNA molecule within a sample that serves as the "input" for the sequencing workflow.

The terms "targeted early barcoding", "early barcoding", "attachment of early barcodes", and "assignment of early barcodes" are used interchangeably and refer to assignment of barcodes to selected nucleic acid targets within a sample by specific hybridization and polymerization of barcode-containing primers at an early processing step. Preferably, barcode assignment occurs during the first enzymatic step that is performed after template nucleic acid molecules are purified from a biological sample. This first enzymatic step can be primer-extension, reverse-transcription, or PCR. When multiple different target sequences are to be tagged and copied from a given sample, a mixture of several different target-specific primers are used in a single reaction volume, with every primer in the mixture having the same sample-specific barcode. Separate early barcoding reactions are carried out for each sample, using similar mixtures of primers bearing distinct barcodes for each sample. Targeted early barcoding allows molecules from different samples to be combined into a single volume for all subsequent processing steps.

The term "degenerate sequence" refers to a stretch of sequence in which, within a population of nucleic acid molecules, two or more different bases can be found at each position. Most often, degenerate sequences are produced such that there is an approximately equal probability of each position having A, C, G, or T (in the case of DNA), or having A, C, G, or U (in the case of RNA). However, in certain situations, different bases can be incorporated in varying ratios at different positions, and some bases can be omitted at certain positions if desired. A degenerate sequence can be of any length.

The terms "molecular lineage tag", "MLT", and "MLT sequence" are used interchangeably and refer to a stretch of degenerate sequence that is contained within a synthetic oligonucleotide (e.g. a primer) and is used to assign a set of diverse sequence tags to copies of template nucleic acid molecules. A molecular lineage tag is designed to have between 2 and 10 degenerate base positions, but preferably has between 6 and 8 base positions. The bases need not be consecutive, and can be separated by constant sequences. The number of possible MLT sequences that can be generated in a population of oligonucleotide molecules is generally determined by the length of the MLT sequence and the number of possible bases at each degenerate position. For example, if an MLT is 8 bases long, and has an approximately equal probability of having A, C, G, or T at each position, then the number of possible sequences is $4^8=65,536$. A molecular lineage tag is not designed to assign a completely unique sequence tag to each molecule, but rather is designed to have a low probability of assigning any given sequence tag to a particular molecule. The greater the number of possible MLT sequences, the lower the probability of any particular sequence being assigned to a molecule. When many template molecules are copied and tagged, the same MLT sequence can be assigned to more than one template molecule. MLT sequences are used to track the lineage of molecules from initial copying through amplification, processing and sequencing. They can be used to distinguish sequences that arise from polymerase misincorporations or sequencer errors from sequences that are derived from true mutant template molecules. MLTs can also be used to distinguish sequences that have the wrong barcode assignment as a result of cross-over of barcodes during pooled amplification. Because the same MLT sequence can be assigned to more than one template molecule, meaningful analysis of MLT sequences requires first identifying variant target sequences and then analyzing the distribution of MLT sequences associated with those variants.

The term "molecular lineage tagging" refers to the process of assigning molecular lineage tags to nucleic acid templates molecules. MLTs can be incorporated within primers, and are attached to copies made from targeted nucleic acids by specific extension of primers on the templates.

The term "include" and its derivations should be understood to mean "including, but not limited to". The words "a", "an", and "the" include both singular and plural referents unless the context indicates otherwise.

Embodiments of the Methods

Methods and compositions are disclosed herein for identifying and quantifying nucleic acid sequence variants. Methods disclosed herein can identify and quantify low-abundance sequence variants from complex mixtures of DNA or RNA. Embodiments of the methods can measure small amounts of tumor-derived DNA that can be found in the circulation of patients with various types of cancer.

Assessment of rare variant DNA sequences is important in many areas of biology and medicine. Small amounts of fetal DNA can be found in the circulation of pregnant women. An embodiment includes analyzing rare fetal DNA that can be used to assess disease-associated genetic features or the sex of the fetus. An organ that is undergoing rejection by the recipient can release small amounts of DNA into the blood, and this donor-derived DNA can be distinguished based on genetic differences between the donor and the recipient. An embodiment includes measuring donor-derived DNA to provide information about organ rejection and efficacy of treatment. In another embodiment, nucleic acids can be detected from an infectious agent (e.g., bacteria, virus, fungus, parasite, etc.) in a patient sample. Genetic information about variations in pathogen nucleic acids can help to better characterize the infection and to guide treatment decisions. For instance, detection of antibiotic resistance genes in the bacterial genome infecting a patient can direct antibiotic treatments.

Detection and measurement of low-abundance mutations has many important applications in the field of oncology. Since tumors are known to acquire somatic mutations, some of which promote the unregulated proliferation of cancer cells, identifying and quantifying these mutations has become a key diagnostic goal. Companion diagnostics have become an important tool in identifying the mutational cause of cancer and then administering effective therapy for that particular mutation. Furthermore, some tumors acquire new mutations that confer resistance to targeted therapies. Thus, accurate determination of a tumor's mutation status can be a critical factor in determining the appropriateness of particular therapies for a given patient. However, detecting tumor-specific somatic mutations can be difficult, especially if tumor tissue obtained from a biopsy or a resection has few tumor cells in a large background of stromal cells. Tumor-derived mutant DNA can be even more challenging to measure when it is found in very small amounts in blood, sputum, urine, stool, pleural fluid, or other biological samples.

Tumor-derived DNA is released into the bloodstream from dying cancer cells in patients with various types of malignancies. Detection of circulating tumor DNA (ctDNA) has several applications including, but not limited to, detecting presence of a malignancy, informing a prognosis, assessing treatment efficacy, tracking changes in tumor mutation status, and monitoring for disease recurrence or progression. Since unique somatic mutations can be used to distinguish tumor-derived DNA from normal background DNA in plasma, a new class of highly specific DNA-based cancer biomarkers are described with clinical applications that may complement those of conventional serum protein markers. In an embodiment, methods include screening ctDNA for presence of tumor-specific, somatic mutations. In such embodiments, false-positive results are very rare since it would be very unlikely to find cancer-related mutations in the plasma DNA of a healthy individual. Described herein are methods that specifically and sensitively measure rare mutant DNA molecules that are shed into blood from cancer cells. Achieving extremely high detection sensitivity is especially important for detection of a small tumor at an early (and more curable) stage.

Since somatic mutations can occur at many possible locations within various cancer-related genes, a clinically useful test for analyzing ctDNA would need to be able to evaluate mutations in many genes simultaneously, and preferably from many samples simultaneously. In embodiments, analysis of a plurality of mutation-prone regions from a plurality of samples allows more efficient use of large volumes of sequence data that can be obtained using massively parallel sequencing technologies. In an embodiment, labeling molecules arising from a given sample with a sample-specific DNA sequence tag, also known as a barcode or index, facilitates simultaneous analysis of more than one sample. By using distinct barcode sequences to label molecules derived from different samples, it is possible to combine molecules and to carry out massively parallel sequencing on a mixture. Resultant sequences can then be sorted based on barcode identity to determine which sequences were derived from which samples. To minimize chances of misclassification, barcodes are designed so that any given barcode can be reliably distinguished from all other barcodes in the set by having distinct bases at a minimum of two positions.

In most protocols that are currently used to prepare samples for massively parallel sequencing, barcodes are attached after several steps of sample processing (e.g. purification, amplification, end repair, etc). Barcodes can be attached either by ligation of barcoded sequencing adapters or by incorporation of barcodes within primers that are used to make copies of nucleic acids of interest. Both approaches typically require several processing steps to be performed separately on nucleic acids derived from each sample before barcodes can be attached. Only after barcodes are attached can samples be mixed.

In an embodiment, barcodes are assigned to targeted molecules at a very early step of sample processing. Targeted early barcode attachment not only permits sequencing of multiple samples to be performed in batch, it also enables most antecedent processing steps to be performed in a combined reaction volume. Once barcodes are attached to nucleic acid molecules in a sample-specific manner, molecules can be mixed, and all subsequent steps can be carried out in a single tube. If a large number of samples are analyzed, targeted early barcoding can greatly simplify the workflow. Since all molecules can be processed under identical conditions in a single tube, the molecules would experience uniform experimental conditions, and inter-sample variations would be minimized. In an embodiment, tagging of nucleic acids from different samples can be achieved in consistent proportions and then used to enable quantitative comparisons of nucleic acid concentrations across samples. In addition to quantifying DNA, targeted early barcoding can enable quantifying RNA (e.g., RNA expression levels across different samples). Once barcodes are attached, targeted nucleic acids bearing different sample-specific barcodes can be amplified in a combined reaction volume by competitive end-point PCR, and relative counts of different barcodes in amplified products could be used to quantify associated nucleic acids in various samples. Thus, early barcoding can be used to quantify a total amount of various targeted nucleic acids, and not just variants, across many samples.

In an embodiment, well-defined mixtures of primers are produced containing combinations of sample-specific barcodes and consistent ratios of gene-specific segments. Such primers can be used for targeted early barcoding and subsequent batched sample processing. These primers can also be used for quantitation of DNA or RNA in different samples. In an embodiment, such primers allow parallel processing and analysis of multiple mutation-prone genomic target regions from multiple samples in a simplified and uniform manner.

Embodiments include methods that accurately quantify mutant DNA rather than simply determining its presence or absence. In an embodiment, an amount of mutant DNA provides information about tumor burden and prognosis. Embodiments are capable of analyzing DNA that is highly fragmented due to degradation by blood-borne nucleases as well as due to degradation upon release from cells undergoing apoptotic death. Since somatic mutations can occur at many possible locations within various cancer-related genes, an embodiment can evaluate mutations in many genes simultaneously from a given sample. Embodiments are capable of finding mutations in ctDNA without knowing beforehand which mutations are present in a patient's tumor. An embodiment is able to screen for many different types of cancer by evaluating multiple regions of genomic DNA that are prone to developing tumor-specific somatic mutations. An embodiment includes multiple samples combined together in the same reaction tube to minimize inter-sample variations.

Although the methods described herein have been optimized for measurement of small amounts of mutant circulating tumor DNA (ctDNA) in a background of normal (wild-type) cell-free DNA in the plasma or serum of a patient having cancer, it is understood that they could be applied more broadly to the analysis of nucleic acid variants from a variety of sources. Examples of such sources include, but are not limited to lymph nodes, tumor margins, pleural fluid, urine, stool, serum, bone marrow, peripheral white blood cells, cheek swabs, circulating tumor cells, cerebrospinal fluid, peritoneal fluid, amniotic fluid, cystic fluid, frozen tumor specimens, and tumor specimens that have been formalin-fixed and paraffin-embedded.

Features:

Methods include identifying and measuring low-abundance variants occurring in multiple mutation-prone regions of genomes from multiple samples in parallel. One aspect includes early attachment of sample-specific DNA barcodes to a plurality of nucleic acid targets that are derived from a plurality of samples. Specifically, a mixture of gene-specific primers, all bearing the same barcode, are used to make tagged copies of several different genomic target regions from nucleic acids in a given sample in a single reaction volume. For each additional sample, this process is repeated in a separate reaction volume using a similar mixture of gene-specific primers bearing a different barcode. All members of a given primer mix have the same sample-specific barcode, but different primer mixes have different barcodes. Once barcodes have been attached, the DNA from multiple samples can be combined into a single volume for further processing.

If many DNA targets from many samples are to be analyzed, large numbers of primers would need to be produced, each having different combinations of barcoded 5' segments and gene-specific 3' segments. Targeted early barcoding allows combining nucleic acids from different samples and processing of the nucleic acids together in a combined reaction volume. Batched processing has an advantage of simplified workflow and greater experimental consistency and uniformity across different samples. Batched processing decreases potential quantitative variability arising from very small inter-sample concentration or temperature differences. Although the variability may be small at time of initial input, the end result may have substantial variability due to the exponential nature of PCR. Amplification of differently barcoded nucleic acid copies in a combined reaction volume by competitive end-point PCR followed by high throughput sequencing of the products would allow direct enumeration of the various barcodes associated with a given genomic target region. The relative quantity of each targeted nucleic acid in the different samples could be deduced from the relative abundance of the various barcodes within the sequence data.

Another aspect includes producing primers by combining modular oligonucleotide segments. Implementing targeted early barcoding requires generating well-defined mixtures of large numbers of primers. Primer mixtures are produced in such a way that each mixture contains identical proportions of 3'-gene-specific segments, ensuring that target nucleic acids from different samples are copied in consistent ratios. This makes it possible to quantitatively compare nucleic acid concentrations across different samples. In an embodiment, combining modular oligonucleotide segments is used. More specifically, to generate each mixture, a portion of a uniform pool of various gene-specific 3' oligonucleotide segments is joined to a single, uniquely-barcoded 5' segment. Since the 3' segments used to produce each final mixture are derived from a common pool (or master-mix), each uniquely barcoded primer mix has similar proportions of the different 3' gene-specific segments. Several approaches are described herein for joining the modular 5' and 3' segments. This modular approach to producing primer mixes allows the production of thousands of primer and barcode combinations that would have otherwise been very costly and laborious to produce. Furthermore, the consistency of gene-specific primer ratios that can be achieved across different mixes would not be possible by mixing individually synthesized primers. Methods described herein utilize next-generation, high-throughput DNA sequencing technologies to identify and quantify nucleic acid variants. These technologies are able to quickly and inexpensively produce sequences from millions of DNA molecules in a massively parallel fashion. By oversampling sequences of a large number of DNA molecules from a particular genomic region using ultra-deep sequencing, it would be possible to identify and enumerate rare sequence variants. The sensitivity of the sequencing is limited by the inherent error rate of the sequencer since incorrectly read bases might be mistaken for true mutant DNA copies. Mutant ctDNA has been reported to comprise on average 0.2% of total plasma DNA (Diehl et al., *Nat Med.* 2008; 14: 985-990)—a range in which sequencer misreads can be problematic. This is a limitation of massively parallel sequencing to measure very low-abundance mutations.

Herein methods are described that use clonal overlapping paired-end sequencing to achieve sequence redundancy in mutation-prone regions, thereby allowing base calls to be made with much greater confidence. Embodiments include methods of reducing, suppressing, and distinguishing sequencer-derived errors. Using an Illumina® next-generation sequencing platform, an embodiment includes obtaining a read in one direction from a clonal cluster of DNA molecules, and then subsequently obtaining a read in the opposite direction (from the opposite strand of the duplex). The length of each "paired-end" read can be 36, 50, 75, 100, or 150 bp or longer. An embodiment includes sequencing short PCR amplicons in a paired-end fashion to obtain overlapping reads from both strands of a clone. By designing the mutation-prone region to be in the area of sequence overlap, clonal sequence redundancy can be achieved in this region. Thus, each clonal sequence from a mutation-prone region is read in one direction, and then is proofread in the other direction. Read-pairs that do not have perfect agreement in the overlapping region (after obtaining a reverse-complement of one of the reads) can be attributed to sequencer error, and can be ignored in the final analysis. In this way, sequencer-generated errors in a region of interest can be reduced since a probability of finding the same sequencer error in reads from both strands of a clone is exceedingly low. By reducing the background of sequencer errors, it becomes possible to achieve better detection sensitivity for rare mutant molecules. Detection sensitivity is especially important in patients with early-stage cancers who are likely to have a very low concentration of mutant ctDNA molecules in their blood.

Another aspect includes distinguishing nucleotide misincorporation errors that can be introduced during DNA copying, amplification, or processing. After suppression of sequencer-derived errors, variant sequences are still found that do not correspond to authentic mutations arising from mutant template DNA molecules. A majority of these variant sequences arise from incorporation of incorrect nucleotides when DNA template molecules are copied or amplified. Possible causes of such misincorporation errors include but are not limited to DNA damage (for example, cytosine deamination during heating) or polymerase-induced errors.

To distinguish variant sequences arising from true mutant template molecules versus those arising from misincorporation errors, an embodiment includes molecular lineage tagging. In molecular lineage tagging, a degenerate sequence called a molecular lineage tag (MLT) is incorporated into primers that make a small number of copies (between 2 to 20) of an original template DNA molecule. An MLT is a stretch of degenerate sequence having an approximately equal probability of having A, T, C, or G at each position and can be about 2 to about 10 bases in length, but preferably would be 6, 7, or 8 bases long. An MLT sequence can also be split into segments that are separated by non-degenerate positions within an oligonucleotide.

It is not necessary that each template molecule be tagged with a unique MLT, but only that each template molecule should have a low probability of being tagged with any given MLT-sequence. For example, if the MLT region consisted of 8 degenerate positions, then 4^8=65,536 possible MLT sequences could be generated. MLT-containing primers are used to make a limited number of copies of the template DNA molecules, via either a few cycles (2 to 4) of PCR or primer-extension. Thus, each template copy would be tagged with one of 65,536 possible MLT sequences. When these tagged copies are amplified by PCR, the "progeny" molecules derived from amplification of a given "parent" copy should retain the same identifying MLT sequence as the parent molecule. If a variant sequence arose from a true mutant template molecule, then many copies of a given MLT sequence should be associated with that variant sequence (since that MLT was associated with the mutant copy at the beginning of the amplification process). On the other hand, if an error was introduced during amplification or processing, one would expect a smaller number of copies of a given MLT to be associated with the erroneous variant sequence (unless the error occurred at a very early cycle of amplification). It is important to note that if several thousand template molecules are tagged with MLTs, there is a high probability that some MLT sequences may be assigned to more than one template molecule.

With non-unique MLT's, it is less informative to evaluate the percentage of mutant and wild-type sequences associated with a particular MLT sequence. Rather, it is preferable to identify mutant sequences, and then to evaluate distribution of MLT sequences associated with those variants. If the number of sampled clonal sequences (post-amplification) is several-fold greater than the number of tagged template copies, then variant sequences arising from true mutant template molecules would be associated with multiple copies of a given MLT sequence, whereas variants arising from misincorporation errors would be likely to be associated with fewer copies of any given MLT. Analysis of MLT distributions (number of different MLT sequences and number of copies of each sequence) associated with a particular variant made it possible to identify the majority of variants arising from misincorporation errors, thereby further improving the sensitivity for detecting true template-derived mutations.

Another aspect includes distinguishing sequences that are misclassified as belonging to a wrong sample. Such incorrect classification of a sequence can occur if it is associated with an inappropriate barcode. Since barcodes are designed to differ from all other barcodes in a set at a minimum of two distinct positions, misclassification due to barcode sequence errors would be rare. However, cross-over of barcodes has been observed from differently barcoded molecules that undergo combined polymerization or amplification in the same reaction volume. This can happen, for example, if primer-extension stalls before a polymerase has completed extending on a template during a given cycle of PCR. That partially-extended strand (possibly containing a mutant or wild-type sequence) could then anneal to a different template during the next cycle of PCR, and could incorporate an inappropriate barcode. Alternatively, if two strands of DNA containing different barcodes are annealed to each other via a common complementary sequence, the 3'-5' exonuclease activity of a proofreading polymerase can digest the barcode on one strand and then extend that strand using the opposite strand's barcode as a template. MLT sequences can be used to distinguish sequences derived from such barcode "cross-over" events. If an MLT region is positioned in proximity to or adjacent to a barcode sequence, then it can be used to track the lineage of the barcode. If a variant is tagged with an inappropriate barcode as a result of cross-over during the process of amplification, then one would expect fewer than average copies of a particular MLT sequence to be associated with that barcode/variant combination. To further aid in distinguishing cross-over sequences, a second MLT can be positioned on the opposite side of the mutation-prone region (so that the sequence order, for example, could be MLT-1/Barcode/mutation-prone region/MLT-2). In this case, DNA molecules that undergo cross-over between a barcode and a mutation prone region would also undergo cross-over of MLT-1 between MLT-2. Thus, such crossed-over sequences could be identified because the number of copies of a particular MLT-1/MLT-2 combination would be lower than for sequences that did not undergo cross-over. Thus, MLT sequences can allow differently barcoded molecules to be amplified in a combined reaction volume while maintaining accurate assignment of mutations to specific samples.

Another aspect includes highly-specific tagging, copying, and amplification of several genomic target regions from several samples simultaneously in a single reaction volume while minimizing accumulation of unwanted, spurious amplification products. Such highly multiplexed processing and amplification is prone to accumulation of spurious products because of the presence of large numbers of different primers. Having a complex mixture of primers with different combinations of barcodes, degenerate sequence regions, and gene-specific regions in a single PCR amplification can lead to formation of many primer dimers and non-specific amplification products. An embodiment includes multi-step tagging and amplifying without having to compromise primer concentrations. An embodiment of a process includes highly stringent purification of desired amplification products between each amplification step to remove unextended primers, spurious extension products, and genomic template DNA as well as enzyme, buffer, and nucleotides. An embodiment utilizes biotin-tagged oligonucleotides to mediate specific isolation of desired products. Another embodiment utilizes high-temperature washes when using biotin-tagged oligonucleotides. Another embodiment includes digesting unwanted single-stranded products and primers with an exonuclease to further improve amplification specificity. An embodiment also uses nested primers to provide further selectivity for desired products. An embodiment includes universal PCR primers for the final amplification. Under the stringent conditions described herein, universal PCR primers can be used for the final amplification without significant accumulation of spurious products.

Methods:

Producing Combinations of Modular Oligonucleotide Segments for Tagging of Nucleic Acids In an embodiment, tagged copies of multiple nucleic acid targets are made from template DNA or RNA derived from a given sample. To produce such tagged copies, a mixture of primers is used in which the 3'-segments of the primers are able to hybridize to RNA or DNA targets by sequence complementarity (as illustrated, for example, by the reverse primers 1 in FIG. 1). A polymerase (such as a reverse transcriptase or a DNA polymerase) can then be used to extend the primers in the 5' to 3' direction using the targeted nucleic acids as templates. In an embodiment, a sample-specific DNA barcode sequence can be incorporated into the 5'-segment of each primer such that the barcode becomes attached to the copy of the target template after undergoing primer-extension. Since multiple target templates are to be copied from a given sample in a single reaction tube, a mixture of primers is required having various target-specific sequences in their 3'-segments and all having the same sample-specific barcode sequence in their 5'-segments. If several different samples are to be analyzed, then similar mixtures of primers must be made for each sample, with each mixture containing a unique, sample-specific barcode sequence in the 5'-segment. In some embodiments, the 5'-segment of each primer can also contain other elements such as sequencing adapters (to facilitate sequencing of the copied DNA), binding sites for PCR primers, or stretches of degenerate sequence (having equal probability of A, C, T, or G bases at each position) that can serve as tags to follow the lineage of molecules during copying, amplification, and sequencing.

In an embodiment, a barcode comprises a unique sequence (typically 6 to 12 nucleotides long) that is used to identify molecules derived from a particular sample after molecules from multiple samples are pooled and sequenced in batch. In an embodiment, a computer program can be used to sort clonal sequences derived from each molecule based on barcode identity. In order to minimize the chance that a sequence derived from one sample might be misclassified as being derived from another sample, each barcode sequence is designed to differ from all other barcodes in the set by at least 2 nucleotides (so that a single sequencing error would not lead to misclassification).

In an embodiment, multiple gene-specific primer regions (at the 3'-ends of primers) are attached in separate batches, to unique sample-specific barcodes (near the 5'-regions of primers). If many genomic targets are to be analyzed from many samples, the number of combinations of primer 3'-ends and 5'-ends can become very large. For example, if 40 target gene regions are to be evaluated from 96 different samples, 40×96=3,840 different oligonucleotides would need to be made, each with a unique combination of 3' gene-specific sequence and 5' barcode. If conventional oligonucleotides were individually synthesized, a mixture of 40 different gene-specific primers having a particular barcode would be used to primer-extend nucleic acid targets from a given sample within a single tube. Thus, all 40 target regions would be tagged with the same sample-specific barcode. However, synthesis and purification of 3,840 oligonucleotides individually would be impractical. Because termination sequences would be abundant when making long primers, full-length oligonucleotides would have to be purified by methods including but not limited to polyacrylamide gel electrophoresis, high performance liquid chromatography, or reverse-phase cartridge purification.

Figure 2:
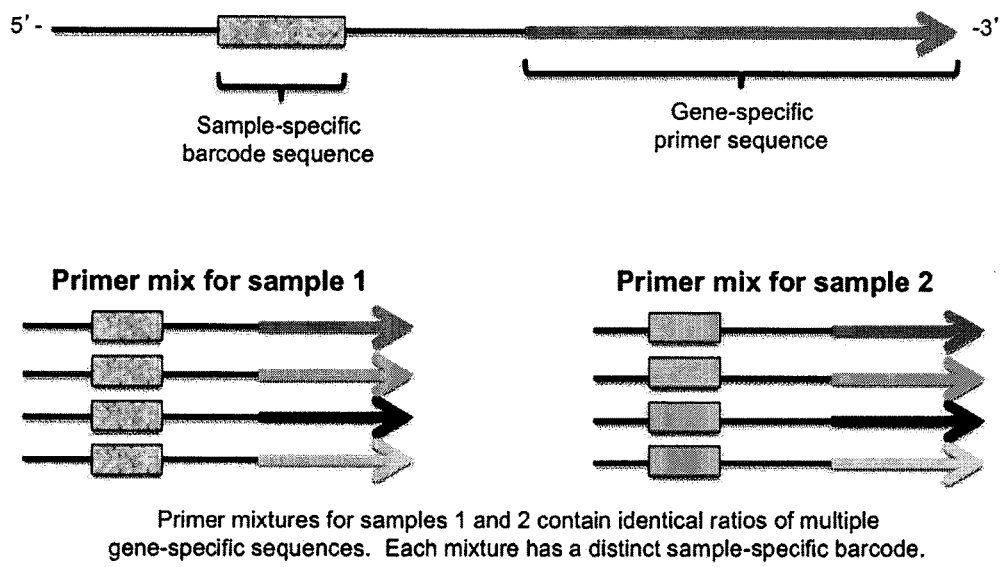
FIG. 2 illustrates a general approach to combining modular oligonucleotide segments to produce mixtures of gene-specific barcoded primers. Primers produced by combining modular segments allow primer-extension and early barcoding of multiple targeted gene regions in a given sample. A primer mix used for a particular sample may have a unique barcode and multiple gene-specific primer sequences. For a different sample, the mix can have the same set of gene-specific sequences in identical ratios, but a different barcode.

To address the need for producing uniform mixtures of multiple gene-specific primer, with each mixture having a unique barcode sequence, embodiments are described in which combinations of modular gene-specific 3' oligonucleotide segments can be attached to a modular barcoded 5' oligonucleotide segment. In various embodiments, production of modular oligonucleotides allows multiple gene-specific 3' segments to be synthesized and uniformly mixed, and then attached in separate batches to each barcoded 5' segment (FIG. 2). Resulting uniquely barcoded primer mixes would each have consistent ratios of gene-specific primer sequences. In some embodiments, such uniform primer mixes could be used to copy and label DNA or RNA molecules from different samples with consistent efficiency (so that the resulting tagged copies would be proportionate to the amount of target nucleic acids in each sample). Subsequent pooled amplification of differently barcoded molecules by competitive PCR, followed sequencing to count barcoded sequences, would enable accurate quantitation of DNA or RNA targets in the various samples. Such uniform primer mixes would be very difficult to achieve by simply mixing individually synthesized primers.

In some embodiments, multiple 3' oligonucleotide segments are produced and mixed, and then the mixture is joined in separate batches to unique 5' oligonucleotide segments. In an embodiment (FIG. 3), different 3'-segments can be synthesized in separate columns on an automated oligonucleotide synthesizer (on solid supports). Synthesis can then be paused and the solid supports from the different columns can be uniformly mixed. Then the mixture can be dispensed into several fresh columns. Synthesis can then be continued, adding a uniquely barcoded 5' segment to each new column. After cleavage, deprotection, and purification, the desired uniquely barcoded uniform primer mixtures are obtained. In another embodiment, mixtures of 5'-phosphorylated 3'-segments can be ligated to different barcoded oligonucleotides using splint-mediated enzymatic ligation. In another embodiment, primer extension can be used to produce combinations of modular segments. In this approach, a single barcoded 5' oligonucleotide can be hybridized via a common sequence to a mixture of complementary templates. These templates can be designed to produce various gene-specific 3'-ends when the barcoded oligonucleotide is primer extended on these templates. In an embodiment, biotin tags on the templates can be used to separate the templates from the desired uniquely barcoded primer mix. Similar primer extension reactions can be performed in separate reaction volumes using different barcoded oligonucleotides to produce several similar uniform primer mixes. In yet another embodiment, mixtures of 3' oligonucleotide segments having reactive chemical conjugation moieties on their 5'-end can be combined in separate batches with uniquely barcoded 5' oligonucleotides segments having reactive conjugation moieties on at their 3' ends. Such chemical conjugation would allow post-synthesis combination of oligonucleotide segments. Special conjugation chemistries have been previously described that can conjugate two oligonucleotide segments together leaving a phosphodiester bond at the junction (or similar bond that would be compatible with subsequent enzymatic processes).

Isolation of Template DNA

Embodiments provide methods for purification or isolation of DNA or RNA from various clinical or experimental specimens. Many kits and reagents are commercially available to facilitate nucleic acid purification. Depending on the type of sample to be analyzed, appropriate nucleic acid isolation techniques can be selected. Substances that might inhibit subsequent enzymatic reaction steps (such as polymerization) should be removed or reduced to non-inhibitory concentrations in purified DNA or RNA samples. A yield of nucleic should be maximized whenever possible. It would be disadvantageous to lose DNA during purification, wherein the lost DNA might include rare variant DNA. When isolating DNA from plasma, about 10 ng to 100 ng of cell-free DNA can be purified from 1 mL of plasma, which corresponds to 3,500 to 35,000 genome copies. To note, DNA yields can vary dramatically, especially in patients with an ongoing disease process such as cancer.

In an embodiment, DNA can also be analyzed from other sample types, including but not limited to the following: pleural fluid, urine, stool, serum, bone marrow, peripheral white blood cells, circulating tumor cells, cerebrospinal fluid, peritoneal fluid, amniotic fluid, cystic fluid, lymph nodes, frozen tumor specimens, and tumor specimens that have been formalin-fixed and paraffin-embedded.

Producing a Limited Number of Tagged Copies of Targeted Nucleic Acids

In an embodiment, a limited number of tagged copies (e.g., fewer than 20) of targeted nucleic acid molecules are made at an early step in the process. After DNA or RNA is purified from the original sample, targeted nucleic acid template molecules can be copied by specifically hybridizing and polymerizing tagged primers. When a plurality of target regions are to be copied and tagged from a given sample, a mixture of modular barcoded primers can be used (as described above). In an embodiment, targeted nucleic acid regions are mutation-prone regions (also called mutation hotspots). A mixture of primers for a given sample can contain sequences at their 3'-ends that specifically hybridize to an area of DNA near or adjacent to a target region. All primers used for a given sample would have the same sample-specific barcode sequence, and different samples would have different barcodes. In some embodiments, the primers can also contain stretches of degenerate bases known as molecular lineage tags (MLTs) that can be helpful in distinguishing sequences arising from true mutant template molecules versus those arising from misincorporation errors occurring during amplification or processing. The MLTs can also help to identify sequences that are assigned to the wrong barcode due to cross-over of barcodes during pooled amplification of differently barcoded molecules. In an embodiment, primers can also contain adapter sequences that are necessary for sequencing, and universal primer binding sites that can be used in subsequent amplifications.

In an embodiment, a DNA polymerase can be used to extend the primers on hybridized templates, thus producing copies of the target nucleic acids with sample-specific barcodes attached. A DNA polymerase can be a thermostable or non-thermostable enzyme, and may or may not have proof-reading activity. Examples of polymerases include, but are not limited to, Taq, Phusion®, $Vent_R$®, Pfu, Pfx, DNA Polymerase I (Klenow fragment), or reverse transcriptase. When specific primer annealing and extension is to be carried out at temperatures above 50° C., thermostable polymerases with hot-start capability are preferred in order to minimize spurious polymerization at room temperature during reaction set-up. Copies of template nucleic acids can be made by a single primer extension step, by a few cycles of primer extension (1 to 10 cycles, with heat-denaturation of the extended products between cycles), or by a few cycles of PCR in which opposite primers are also added (2 to 5 cycles). A few tagged copies of each template molecule can be produced so that a complete sampling of sequences can be obtained even if there is some loss of copies during the various purification, processing, and amplification steps. However, the number of tagged copies must be limited to avoid assigning too many different MLTs to each template molecule, which would require greater sequencing depth for analysis. In an embodiment, after a limited number of tagged copies are made, the polymerase is inactivated, and barcoded copies from different samples can then be pooled into a combined volume for further processing.

Purification of Tagged Copies

In an embodiment, tagged, primer-extended copies of target sequences are purified away from un-extended and non-specifically extended primers and from excess template nucleic acids. Purification also removes other reaction components such as buffer, dNTPs, and polymerase. Removal of un-extended primers and non-specifically extended primers is preferred so that they are not carried over to the next polymerization step. Also, removal of excess primers and template molecules allows greater specificity of polymerization in subsequent steps.

Figure 10:
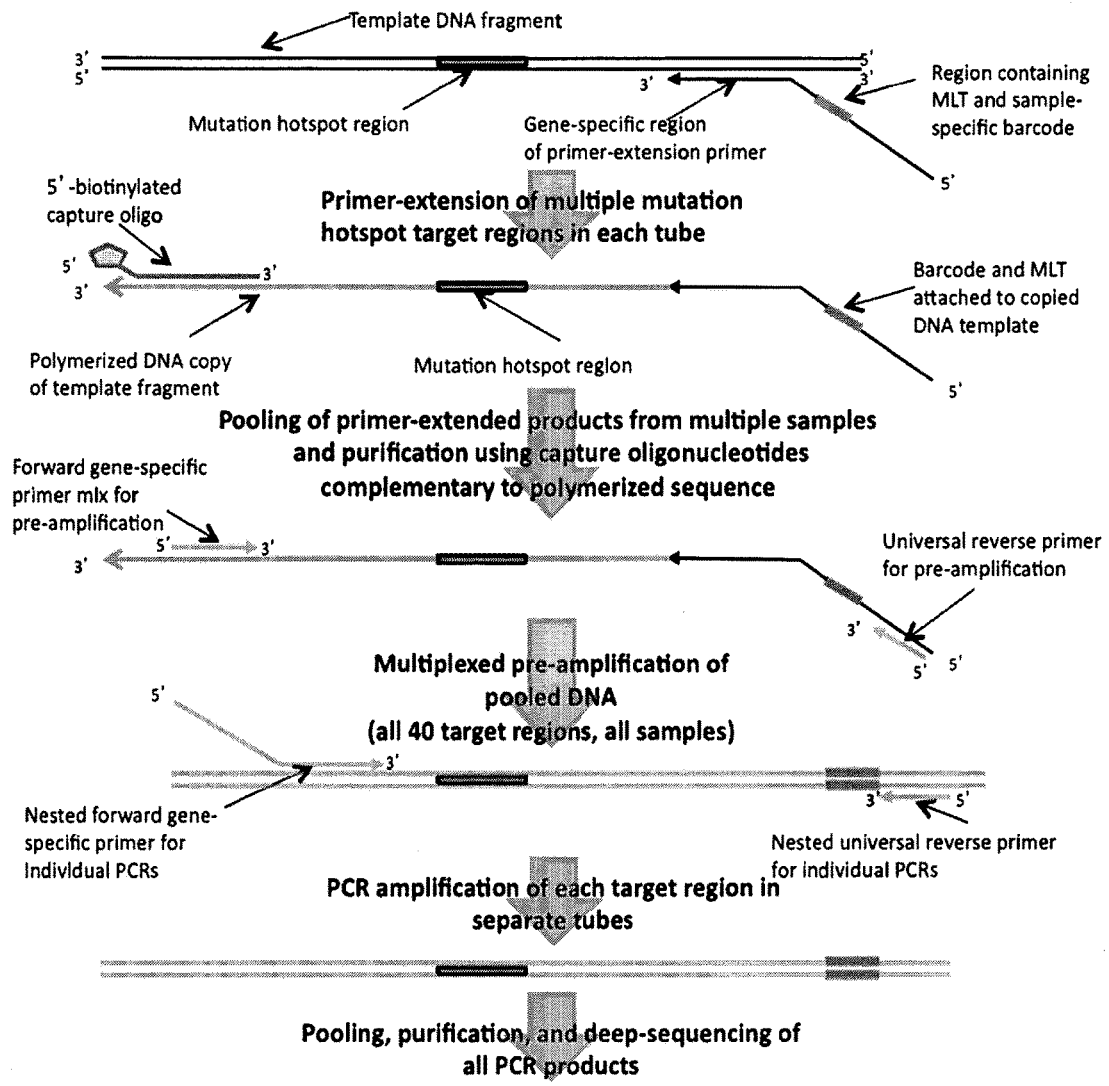
FIG. 10 is a schematic of a process described in Example 2. First, a primer extension step was carried out using primers that assign sample-specific barcodes and MLT sequences to copied template DNA. For a given sample, multiple targeted sequences were copied using multiple gene-specific primers, all bearing the same sample-specific barcode. After stringent purification of specifically extended products, a pre-amplification step was performed in order to produce many copies of the tagged molecules. This allowed splitting of the products into different tubes for separate amplification of each target site, while ensuring that copies of the original templates are adequately sampled. The products of the final PCRs were combined and subjected to clonal overlapping paired-end deep sequencing. Nested primers were used to enhance target specificity at each step.

In an embodiment, purification of specifically tagged and extended products is mediated by capture using biotin-labeled complementary oligonucleotides that hybridize to the specifically extended products. Oligonucleotides can be designed to anneal to sequences produced when tagged primers are extended beyond the mutation-prone region (or target region). Such hybridization of the biotin-labeled capture oligonucleotides to the extended tagged copies can be achieved either by using the biotinylated primers in PCR (FIG. 1), or by subsequently annealing them to primer-extended copies (FIG. 10). In an embodiment, immobilized streptavidin (or an analogue with affinity for biotin) is used to isolate and purify the tagged, extended copies that hybridize to the capture oligonucleotides. Immobilized streptavidin is available in many forms, including but not limited to surface-bound, agarose bead-bound, magnetic bead-bound, or filter-bound. In some embodiments, removal of non-specifically annealed nucleic acids can be achieved by washing the bound molecules at room temperature or at elevated temperatures that would selectively disrupt short, non-specific stretches of hybridization, but would not disrupt specifically-annealed products. In some embodiments, nuclease treatment of the bound molecules can also be used to digest non-specifically annealed products. Nucleases that could be used include but are not limited to Exonuclease I, Exonuclease VII, and Rec Jf. In some embodiments, elution of specifically-annealed copies can be achieved by heat-denaturation or by alkaline-denaturation to separate biotin-labeled strands from the desired single-stranded tagged copies. Biotin labeled strands should remain attached to the immobilized streptavidin since the biotin-streptavidin interaction is not substantially disrupted by heat or moderate alkaline conditions.

In another embodiment, specifically primer-extended copies can be purified by carrying out limited cycles of PCR and then digesting single-stranded nucleic acids to remove un-extended primers. In yet another embodiment, oligonucleotides can be specifically hybridized to primer-extended products to protect their 3'-ends from digestion by a 3' to 5' single-stranded exonuclease such as Exonuclease I.

Double-stranded products that survive digestion can be purified by a variety of approaches, including but not limited to ethanol precipitation, silica membrane partitioning, or binding to magnetic Solid Phase Reversible Immobilization (SPRI) beads.

Second Round of Tagging, Copying, and Purification

In an embodiment, the tagged, pooled, and purified DNA copies from multiple samples can be subjected to another round of limited-cycle primer-extension or limited-cycle PCR (similar number of cycles as described for the first round). Primers used in this second round would be designed to incorporate MLTs on the opposite side of the mutation-prone region relative to the MLTs incorporated in the first round (FIG. 1). This second MLT region could be used to distinguish sequences arising from barcode cross-over events that occurred during pooled amplification or processing. Use of nested primers in the second round of PCR or primer-extension would provide additional selectivity for the targeted genomic sequences. In an embodiment, primers used in the second round could contain universal primer binding sites that would be used for subsequent amplification with universal primers. In an embodiment, primers could also contain adapter sequences that facilitate sequencing using a next-generation sequencer.

In an embodiment, a limited number of specifically primer-extended copies produced in the second round could be purified away from un-extended or non-specifically extended primers and other reaction components using similar approaches as described for the first round. In an embodiment, purification can be achieved using biotinylated capture oligonucleotides designed to specifically hybridize to sites on the opposite primer-extended strands (relative to the hybridization sites of the biotinylated oligonucleotides used in the first round). In an embodiment, nuclease treatment may be used to digest un-extended or non-specifically extended primers.

Amplification and Purification of Specifically Copied and Tagged Products

In an embodiment, products from the first two rounds of copying, tagging, and purification are used as templates for further PCR amplification. In an embodiment, universal primers are used for PCR that are designed to bind to sequences introduced by primers in the first two rounds. Since universal primers are used, it is very important that only desired targeted products remain as templates for the final PCR after the second-round purification. Presence of even small amounts of primer dimers or other spurious products could lead to competitive amplification of undesired templates by the universal primers. In an embodiment, this round of PCR can be carried out for a larger number of cycles than were used in the first 2 rounds. A total of 5 to 40 PCR cycles may be used, depending on the amount of template nucleic acid present and the number of samples being multiplexed. A final PCR is designed to produce sufficient DNA as required for massively parallel sequencing (which can differ depending on the sequencing platform being used). In some embodiments, a final PCR may not be necessary if the required input of the sequencer is satisfied by the amount of DNA product generated after the first 2 rounds. In some embodiments, the DNA products are gel-purified to select products of the desired size and to eliminate unused primers before subjecting to massively parallel sequencing. In some embodiments, other approaches to purification could be used, including but not limited to high-performance liquid chromatography, capillary electrophoresis, silica membrane partitioning, or binding to magnetic Solid Phase Reversible Immobilization (SPRI) beads.

Massively Parallel Sequencing and Data Analysis

In an embodiment, a next-generation sequencer is used to obtain large numbers of sequences from the tagged, amplified, and purified products. Clonal sequences (each sequence arising from a single nucleic acid molecule) produced by such a sequencer can be used to identify and quantify variant molecules using an approach known as ultra-deep sequencing. In principle, because large numbers of sequences can be obtained for each target site and for each sample, rare variants can be detected and measured. However, the error rate of the sequencer can limit the sensitivity of detection because such errors might be mistaken as true variants. To minimize the contribution of sequencer errors, an embodiment uses clonal overlapping paired-end sequences. By separately sequencing opposite strands of DNA from each clonal population, and comparing the overlapping regions of the sequences, the vast majority of variants arising from sequencer errors can be eliminated. In an embodiment, the region of sequence overlap is designed to be in the mutation-prone area. In an embodiment, only read-pairs that perfectly match in the overlapping region are retained for further analysis. For such analysis, instruments that produce clonal paired-end reads (such as the Illumina platform) are preferred. In some embodiments, other massively parallel sequencing platforms that provide sequence redundancy can also be utilized.

In an embodiment, errors introduced into the DNA during amplification or processing can be distinguished from true template-derived mutant sequences by analyzing the distribution of molecular lineage tags (MLTs) associated with variant sequences. In an embodiment, MLTs can also be used to distinguish sequences bearing incorrect barcodes due to cross-over events during pooled amplification.

The present technology may be better understood by reference to the following examples. These examples are intended to be representative of specific embodiments of the invention and are not intended to limit the scope of the invention.

EXAMPLES

Example 1

This example demonstrates application of a deep sequencing approach in which 3 mutation hotspot regions were analyzed from multiple plasma samples. The method in this example includes redundancy within each clonal sequence to produce extremely high quality base-calls in short, mutation-prone regions of plasma DNA. Amplification of both mutated and wild-type sequences was carried out by unbiased PCR in the same tube, ensuring highly accurate and reproducible quantitation. The scheme was designed to have flexibility to simultaneously analyze mutations in several genes from multiple patient samples, making it practically feasible to screen plasma samples for mutant ctDNA without prior knowledge of the tumor's mutation profile.

Materials and Methods
Patient Plasma and Tumor Samples

Under the approval of the Human Investigation Committees at the Yale School of Medicine and at Lawrence & Memorial Hospital, plasma samples were obtained from 30 patients with stage I-IV non-small cell lung cancer (NSCLC) between July 2009 and July 2010. Informed consent was obtained from all patients. Most patients were recruited in the radiation oncology clinic, and underwent treatment with radiation therapy, chemotherapy, targeted systemic therapy, and/or surgery. Whenever possible, blood samples were collected from patients before starting the current course of treatment and then at subsequent times during and after treatment. A total of 117 samples were obtained. Formalin-fixed, paraffin-embedded tumor specimens were obtained for all patients with non-squamous histology whose tumors had not already been tested for mutations by a clinical laboratory, and for whom sufficient tissue was available in the block after standard pathology evaluation.

Extraction and Amplification of Plasma DNA

Blood was collected in EDTA-containing tubes (Becton Dickinson) and was centrifuged at 1000 g for 10 minutes within 3 hours of collection. Plasma was transferred to cryovials, being careful to avoid the buffy coat, and was stored at −80° C. until further processing. Frozen plasma aliquots stored at −80° C. were thawed to room temperature, and DNA was purified using the QIAamp® DNA Blood Mini kit (Qiagen Sciences, Valencia, Calif.) as per the manufacturer's instructions. 5 μg of carrier RNA was added to each 200 μL plasma sample as recommended to improve adsorption of low-concentration nucleic acids to the silica membrane.

Purified plasma DNA was then subjected to 2 rounds of amplification by PCR (in triplicate) using primers designed to amplify short DNA segments that included codons 12 and 13 of KRAS, codon 858 of EGFR, and codon 600 of BRAF. The sequences of the primers used in both rounds of PCR are listed in Table 1.

TABLE 1

Primers used in first and second rounds of PCR.

| PCR Primer | Sequence (5'-3') | SEQ ID NO: |
|---|---|---|
| Round 1 Forward KRAS* | GGCCTGCTGAAAATGACTGAATATAAAC | 1 |
| Round 1 Reverse KRAS* | TTCGTCCACAAAATGATTCTGAATTAGC | 2 |
| Round 1 Forward BRAF* | TCATGAAGACCTCACAGTAAAAATAGGTG | 3 |
| Round 1 Reverse BRAF* | CACAAAATGGATCCAGACAACTGTTC | 4 |
| Round 1 Forward EGFR* | GTACTGGTGAAAACACCGCAGCAT | 5 |
| Round 1 Reverse EGFR* | CTTACTTTGCCTCCTTCTGCATGGTATT | 6 |
| Round 2 Forward KRAS | GG[FWD BC]CGAACAGTCTCCGAATATAAACTTGTGG TAGTTGG | 7 |
| Round 2 Reverse KRAS | GC[REV BC]GGATGAGTGCAGTGAATTAGCTGTATCG TCAAG | 8 |
| Round 2 Forward BRAF | GG[FWD BC]CGAACAGTCTCCAAATAGGTGATTTT GGTCTAGC | 9 |
| Round 2 Reverse BRAF | GC[REV BC]GGATGAGTGCAGCCAGACAACTGTTCAA ACTGA | 10 |
| Round 2 Forward EGFR | GG[FWD BC]CGAACAGTCTCCCAGCATGTCAAGAT CACAGATT | 11 |
| Round 2 Reverse EGFR | GC[REV BC]GGATGAGTGCAGGCATGGTATTCTTT CTCTTCC | 12 |

*Primers were gel-purified prior to use.
FWD BC = Forward barcode
REV BC = Reverse barcode In a first round of PCR, all hotspot regions from a given sample were amplified in a multiplexed fashion. Three aliquots of purified plasma DNA from each sample were used as templates in three identical multiplexed PCRs containing 1× Kapa Fidelity buffer (Kapa Biosystems, Inc., Woburn, Mass.), 300 μM each dNTP, 50 nM each primer (Round 1 Forward and Reverse KRAS, BRAF, and EGFR primers), and 1 unit/50 μL HiFi Hotstart DNA polymerase (Kapa Biosystems). Mineral oil was added to all PCR tubes to minimize evaporation during heating. Temperature cycling parameters were 95° C. for 2 minutes, followed by 35 cycles of 98° C. for 20 sec, 64° C. for 20 sec, and 72° C. for 30 sec. A final extension was performed at 72° C. for 1 minute, prior to cooling the reaction at 4° C. EDTA was then added at a final concentration of 5 mM to stop polymerase activity.

The amplicons from each first round PCR were diluted 5000-fold and used as templates for 3 separate second round PCRs to individually amplify the hotspot regions of KRAS, BRAF, or EGFR. To promote specific amplification, the second-round primers were nested relative to the primers used in the first round of PCR. The nested primers were labeled with sample-specific barcode sequences to allow multiplexed sequencing of DNA from many samples. The barcode sequences were 6 nucleotides in length, and were designed to differ from all other barcodes in the set at a minimum of 2 positions so that a single sequencing error would not lead to misclassification of samples. Different combinations of 16 forward and 16 reverse barcoded primers could be used to uniquely identify up to 256 different samples. PCR was carried out using the same reaction conditions as were used in the first round, with the following modifications: the annealing temperature was increased to 65° C., and the 3 pairs of multiplexed primers were replaced with a single pair of barcoded primers (Round 2 Forward and Reverse KRAS, BRAF, or EGFR primers listed in Table 1) at a final concentration of 200 nM each. After addition of 5 mM EDTA, the PCR products were mixed together to produce 3 pools, one for each of the 3 replicate reactions. All PCR steps were carried out using a high-fidelity polymerase (HiFi HotStart, Kapa Biosystems).

Production of Barcoded PCR Primers

Figure 9:
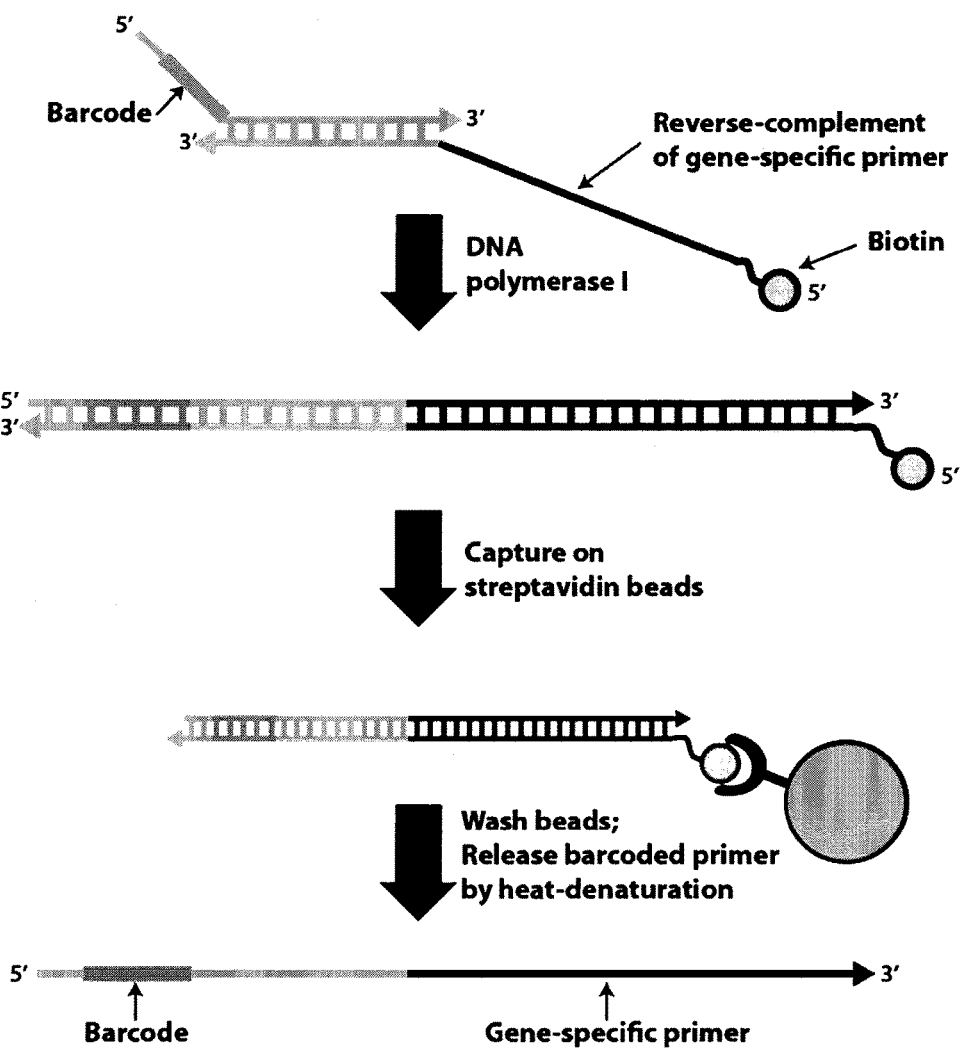
FIG. 9 shows a scheme for appending modular barcodes to gene-specific primers. An ability to combine barcodes and gene-specific primers in a modular fashion provides flexibility to modify or expand a panel of genes or number of samples being tested. A gene-specific primer was added to the 3'-end of a barcoded oligonucleotide by polymerization on a biotinylated template. A biotin tag was used to capture a double-stranded product onto streptavidin resin. A barcoded primer was then released into solution by heat-denaturation. In a similar manner, a mixture of biotinylated templates can be used to produce a mixture of gene specific primers, all having the same barcode. Separate reactions use different barcoded oligonucleotides to produce uniquely barcoded primer mixes that can be used for targeted early barcoding.

In order to build flexibility and scalability into the design of the deep sequencing scheme, barcoded oligonucleotides and gene-specific PCR primers were combined in a modular fashion, as illustrated in FIG. 9. A set of 16 unique barcodes was produced for the forward primers, and a different set of 16 barcodes was produced for the reverse primers. These barcodes were 6 nucleotides in length, and were designed to differ from all other barcodes in the set by at least 2 nucleotides (to minimize the probability that miscalled bases would cause misclassification of sequences). Each barcode was incorporated into an oligonucleotide, which was primer-extended using a partially complementary single-stranded template containing the reverse-complement of the gene-specific primer sequence. The sequences of the template and barcode-containing oligonucleotides are listed in Table 2.

TABLE 2

Oligonucleotides used to produce barcoded primers.

| Oligonucleotide | Sequence (5'-3') | SEQ ID NO: |
|---|---|---|
| Forward KRAS template | Biotin-CCAACTACCACAAGTTTATATTCGGAGACTGTTCG | 13 |
| Forward EGFR template | Biotin-AATCTGTGATCTTGACATGCTGGGAGACTGTTCG | 14 |
| Forward BRAF template | Biotin-GCTAGACCAAAATCACCTATTTGGAGACTGTTCG | 15 |
| Forward barcode 1 oligo | GGAACCTTCGAACAGTCTCC | 16 |
| Forward barcode 2 oligo | GGAACGTACGAACAGTCTCC | 17 |
| Forward barcode 3 oligo | GGAAGCATCGAACAGTCTCC | 18 |
| Forward barcode 4 oligo | GGAAGGAACGAACAGTCTCC | 19 |
| Forward barcode 5 oligo | GGATCCATCGAACAGTCTCC | 20 |
| Forward barcode 6 oligo | GGATCGAACGAACAGTCTCC | 21 |
| Forward barcode 7 oligo | GGATGCAACGAACAGTCTCC | 22 |
| Forward barcode 8 oligo | GGATGGTACGAACAGTCTCC | 23 |
| Forward barcode 9 oligo | GGTACCTACGAACAGTCTCC | 24 |
| Forward barcode 10 oligo | GGTACGAACGAACAGTCTCC | 25 |
| Forward barcode 11 oligo | GGTACGTTCGAACAGTCTCC | 26 |
| Forward barcode 12 oligo | GGTAGCTTCGAACAGTCTCC | 27 |
| Forward barcode 13 oligo | GGTAGGATCGAACAGTCTCC | 28 |
| Forward barcode 14 oligo | GGTTCGATCGAACAGTCTCC | 29 |
| Forward barcode 15 oligo | GGTTGCATCGAACAGTCTCC | 30 |

TABLE 2-continued

Oligonucleotides used to produce barcoded primers.

| Oligonucleotide | Sequence (5'-3') | SEQ ID NO: |
|---|---|---|
| Forward barcode 16 oligo | GGTTGCTACGAACAGTCTCC | 31 |
| Reverse KRAS template | Biotin-CTTGACGATACAGCTAATTCACTGCACTCATCC | 32 |
| Reverse EGFR template | Biotin-GGAAGAGAAAGAATACCATGCCTGCACTCATCC | 33 |
| Reverse BRAF template | Biotin-TCAGTTTGAACAGTTGTCTGGCTGCACTCATCC | 34 |
| Reverse barcode 1 oligo | GCAATCAAGGATGAGTGCAG | 35 |
| Reverse barcode 2 oligo | GCAATGATGGATGAGTGCAG | 36 |
| Reverse barcode 3 oligo | GCAAGATAGGATGAGTGCAG | 37 |
| Reverse barcode 4 oligo | GCAACATTGGATGAGTGCAG | 38 |
| Reverse barcode 5 oligo | GCATCATAGGATGAGTGCAG | 39 |
| Reverse barcode 6 oligo | GCATAGTTGGATGAGTGCAG | 40 |
| Reverse barcode 7 oligo | GCATCAATGGATGAGTGCAG | 41 |
| Reverse barcode 8 oligo | GCATGTATGGATGAGTGCAG | 42 |
| Reverse barcode 9 oligo | GCTAACATGGATGAGTGCAG | 43 |
| Reverse barcode 10 oligo | GCTAGTAAGGATGAGTGCAG | 44 |
| Reverse barcode 11 oligo | GCTATGTAGGATGAGTGCAG | 45 |
| Reverse barcode 12 oligo | GCTTACAAGGATGAGTGCAG | 46 |
| Reverse barcode 13 oligo | GCTTCATTGGATGAGTGCAG | 47 |
| Reverse barcode 14 oligo | GCTTAGTAGGATGAGTGCAG | 48 |
| Reverse barcode 15 oligo | GCTTCTAAGGATGAGTGCAG | 49 |
| Reverse barcode 16 oligo | GCTACAATGGATGAGTGCAG | 50 |

Barcode sequences are boldfaced and underlined.

Each forward barcode oligo (8 µM) was annealed to each forward template oligo (8 µM) in separate reaction tubes containing 1×NEBuffer 2 (New England Biolabs, Ipswich, Mass.), 200 µM each dNTP, and 1 mM dithiothreitol. Annealing was carried out by heating the solution to 95° C. for 2 minutes, 60° C. for 1 minute, and then slowly cooling to 25° C. over approximately 15 minutes. All possible combinations of forward barcode and template oligos were produced. The set of reverse oligos were annealed in a similar manner. 1 unit/10 µL of DNA polymerase I, Large (Klenow) Fragment (New England Biolabs) was added to each tube, and the reaction was incubated at 25° C. for 30 minutes. The reaction was stopped by adding 25 mM ethylenediaminetetraacetic acid (EDTA) and heating to 75° C. for 20 minutes. A biotin tag attached to the 5'-end of the template oligonucleotide was used to purify the primer-extended products from the reaction mix by binding to high capacity streptavidin-coated agarose resin (ThermoFisher Scientific, Wilmington, Mass.) (5 µL resin slurry added per 50 µL reaction). The resin particles were agitated constantly in the solution at room temperature for 8 hours. The resin was washed three times in buffer containing 10 mM Tris pH 7.6 and 50 mM NaCl. The barcoded PCR primers were then released from the resin-bound template oligos into a fresh 40 µL volume of the same buffer by heat denaturation at 95° C. for 1 minute. After concentration adjustment, the primers were ready for use in PCR.

Analysis of Cell Line DNA

Genomic DNA was purified from human cancer cell lines using the same method used for purifying plasma DNA, after suspending cells in 0.2 mL of phosphate-buffered saline. The following cell lines were used: A549 (having a KRAS Gly12Ser mutation), H1957 (having an EGFR Leu858Arg mutation), and YUSAC (having a BRAF Val600Glu mutation). Cells were passed in culture for no more than 6 months after being thawed from original stocks. Because cell lines were used only for analysis of short regions of genomic DNA, authentication of lines by our laboratory was limited to sequencing of those regions. To test the performance of the deep sequencing method for a particular gene, DNA derived from cells known to be either mutant or wild-type with respect to that gene was mixed in various ratios between 10,000:1 and 1:10,000. Cell line DNA samples were then amplified and sequenced according to the same methods that were used for plasma DNA.

Ultra-Deep Sequencing

Barcoded PCR products from all samples were mixed to produce 3 separate pools, each corresponding to one set of replicate reactions. Uniquely indexed TruSeq® adapters (Illumina, Inc., San Diego, Calif.) were ligated to each of the 3 pools of PCR amplicons using a modified version of the manufacturer's protocol. Amplicon pools were purified by phenol-chloroform-isoamyl alcohol (PCA, Sigma-Aldrich Co., St. Louis, Mo.) extraction followed by ethanol precipitation. Addition of deoxyadenosine to the 3'-ends of the blunt-ended amplicons was performed according to Illumina's recommendations. PCA extraction and ethanol precipitation were again used for purification. TruSeq adapters were ligated and the products were purified on a 2% agarose gel according to the standard protocol. DNA concentration was estimated using a Bioanalyzer 2100 (Agilent Technologies, Santa Clara, Calif.). Without further amplification, the 3 pools were combined and loaded onto a single lane of an Illumina HiSeq® 2000 instrument. Prior to loading, the samples were diluted by adding between 2- and 8-fold excess Phi-X DNA to improve cluster discrimination. Sequencing was carried out in multiplexed, 75 base pair, paired-end mode at the Yale Center for Genomic Analysis.

Data Analysis

A computer script was written to filter, assort, align, and count millions of paired-end sequences. First, a read-pair was assigned to a data bin based on the barcode of each read in the pair. Then, based on PCR primer sequences, the pair was assigned to one of the reference genes. Next, the longest stretch of perfect sequence agreement between each pair of reads was determined, and this was used to align the reads to the reference sequence for the gene. A read pair was discarded if either member did not pass Illumina filtering or a nucleotide was reported to be "."; if there was an inconsistency in barcodes, strands, or PCR tags; or if their region of perfect sequence agreement was less than 36 nucleotides in length. Finally, variant sequences confirmed by reads from both strands were identified and counted within each data bin based on comparison to the reference sequence. A module used to perform sequence alignments using a Smith-Waterman algorithm was taken, with permission, from Dr. Conrad Huang, Resource for Biocomputing, Visualization & Informatics, University of California, San Francisco. A module used to determine the longest common substring was taken from a web resource.

Confirmation of Mutations in Tumor Tissue

Genomic DNA was isolated from paraffin-embedded tumor tissue samples using the QUICKEXTRACT FFPE DNA extraction kit (a kit used to isolate DNA from formalin-fixed, paraffin-embedded tissues) (Epicentre Biotechnologies, Madison, Wis.). Mutation hotspot regions of KRAS, BRAF, and EGFR were amplified using the same PCR primers that were used in the first round of PCR described above. Sanger sequencing was performed on gel-purified amplicons, and mutations were identified from chromatograms using Mutation Surveyor software (SoftGenetics LLC, State College, Pa.).

Determining the Absolute Concentration of Mutant DNA in Plasma.

Real-time quantitative PCR was used to measure the concentration of KRAS DNA fragments in each patient's plasma sample. This value was multiplied by the fraction of mutant molecules as determined by deep sequencing in order to calculate the absolute mutant KRAS DNA concentration. PCR conditions were the same as those used in the first round of amplification described above except for the use of a single pair of primers (Round 1 KRAS Fwd and Rev) at 200 nM final concentration, and the addition of SYBR® Green dye (Stratagene, La Jolla, Calif.) at 1:60,000 final dilution. Amplification was carried out using an IQ5 Real-time PCR Detection System with version 2.1 software (Bio-Rad Laboratories, Hercules, Calif.). To enable determination of absolute copy numbers, a standard curve was generated using known concentrations of a cartridge-purified oligonucleotide that was designed to mimic the fragment of KRAS DNA being amplified from plasma. The sequence of the oligonucleotide was: 5'-AAGGCCTGCT-GAAAATGACTGAATATAAACTTGTGGTAGATG-GAGCTGGTGGCGTA AGCAAGAGTG CCTTGACGA-TACAGCTAATTCAGAATCATTTTGTGGACGAATA-3' (SEQ ID No: 51). Real-time PCRs were performed in triplicate, and the KRAS DNA concentration was determined using the mean of the 3 measurements.

Results

Error Suppression Reveals Low-Abundance Variants

To determine the relative abundance of tumor-specific mutations, massively parallel sequencing was performed on PCR amplicons derived from plasma DNA fragments containing known mutation hotspots. Thousands of clonal sequence reads from each plasma sample were compared to reference sequences in order to identify and quantify variants. For proof of concept, analysis was restricted to frequently mutated codons within 3 oncogenes that commonly develop somatic mutations in various malignancies: codons 12 and 13 of KRAS, codon 600 of BRAF, and codon 858 of EGFR. By designing PCR primers that flank very short regions (<50 bp) surrounding these mutation hotspots, adequate amplification of highly fragmented plasma DNA could be ensured and greater sequence depth could be achieved. Modular attachment of DNA barcode tags to the 5'-ends of the PCR primers allowed sequencing of up to 256 DNA samples in batch (FIG. 4A and FIG. 9). A median depth of 108,467 read pairs was obtained per mutation site per sample after filtering and de-multiplexing a total of 86,359, 980 raw sequences generated on a single lane of an Illumina HiSeq® 2000 flow cell.

Importantly, the design of short PCR amplicons enabled us to devise a sequencing strategy that could distinguish mutant from wild-type DNA molecules with very high confidence. Illumina's paired-end sequencing mode was modified to achieve partial overlap of 75 base-pair bidirectional reads obtained sequentially from the forward and reverse strands of each clonal DNA cluster on the flow cell (FIG. 4B). Mutation hotspots were included in the overlapping sequence region so that the hotspot within each clone would be read from one strand and then proofread from the opposite strand. By discarding clones that did not have perfect sequence agreement between the two paired-end reads, the vast majority of sequencer-generated errors were eliminated. Imperfect sequence agreement was found in 22% of read pairs that had already passed Illumina's chastity filter. A median error frequency of 0.31% per base was observed when directly comparing single reads derived from either strand of wild-type control samples to known reference sequences. The frequency of such errors was reduced to 0.07% per base in the region of overlap after removing read pairs that lacked sequence consistency.

Figure 5:
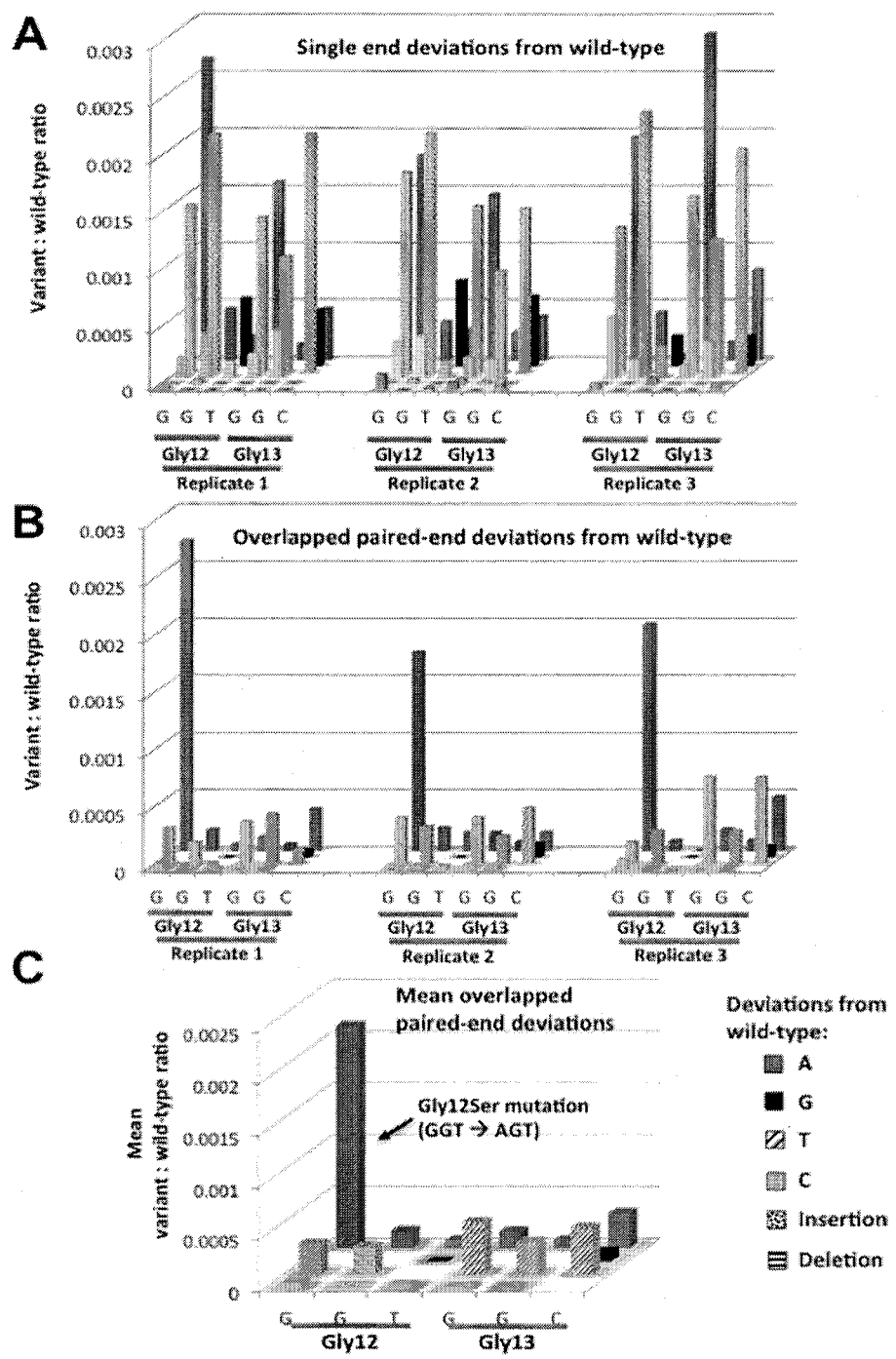
FIGS. 5A-C are graphs depicting suppression of spurious mutation counts to reveal low-abundance variants. Each bar indicates the frequency of a particular deviation from the wild-type sequence occurring within the codon 12/13 hotspot region of KRAS. The tested sample contains 0.2% DNA derived from a lung cancer cell line that is known to be homozygous for a KRAS Gly12Ser mutation.

Any remaining errors were highly unlikely to be caused by coincidentally consistent misreads from opposite ends of a clone. Rather, most of these errors were probably present within the DNA molecules being sequenced, introduced by polymerase misincorporations or DNA damage. To further discriminate true mutations from such errors, all amplification and processing steps were performed in triplicate, and the mean of the three mutation counts was determined. This was done based on the premise that true mutations would be reproducibly counted in all three instances, whereas counts from randomly occurring errors would be more variable (recognizing that the distribution of errors is not entirely random). Using this approach, the frequency of miscalls of specific mutations from known wild-type samples was reduced to a median value of 0.014% (interquartile range [IQR]: 0.0052% to 0.023%; Table 3). Suppression of errors in this manner permitted rare mutations to be identified with a high degree of certainty (FIG. 5).

TABLE 3

Background level of spurious mutation counts obtained from known wild-type samples.

| Mutation Type | Fraction of mutant: wild-type counts (from 3 replicate PCRs) |
|---|---|
| BRAF Val600Glu | 0.00013 |
| EGFR Leu858Arg | 0.000047 |
| KRAS Gly12Ser | 0.00029 |
| KRAS Gly12Val | 0.00018 |
| KRAS Gly12Arg | 0.000057 |
| KRAS Gly12Asp | 0.00015 |
| KRAS Gly12Ala | 0.000014 |
| KRAS Gly12Cys | 0.00025 |
| KRAS Gly13Ser | 0.00015 |
| KRAS Gly13Val | 0.00029 |
| KRAS Gly13Arg | 0.000050 |
| KRAS Gly13Asp | 0.000044 |
| KRAS Gly13Ala | 0.000058 |
| KRAS Gly13Cys | 0.00049 |
| Median Value | 0.00014 |
| Interquartile range | 0.000052 to 0.00023 |

Sensitive and Accurate Quantitation of Mutant DNA

Figure 6:
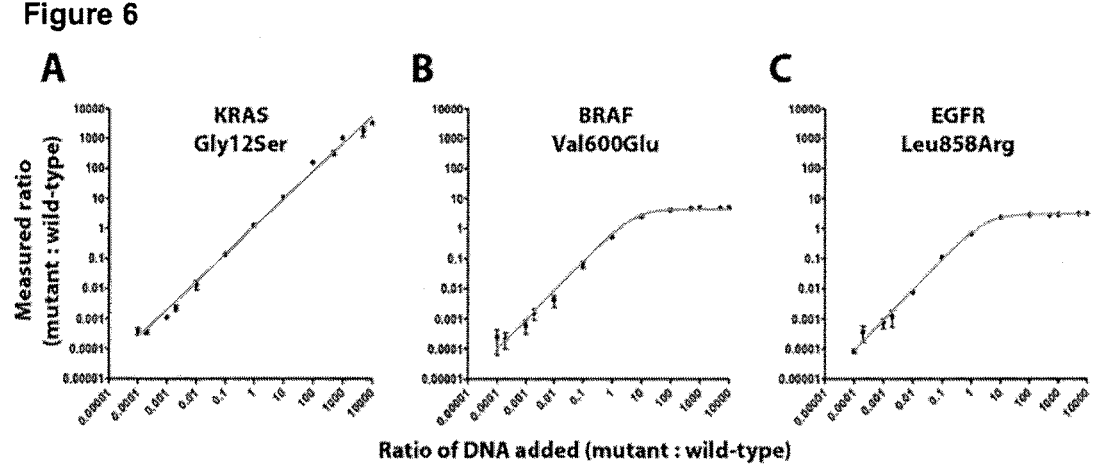
FIGS. 6A-C indicates the performance of error-suppressed deep sequencing. Measurements of DNA extracted from mutant and wild-type cancer cell lines mixed in various ratios ranging from 1:10,000 to 10,000:1 show a high degree of accuracy and reproducibility.

Next, mutant and wild-type DNA levels were measured over a broad range of relative concentrations. Genomic DNA from KRAS-, BRAF-, or EGFR-mutant cancer cell lines was mixed in different ratios, and then subjected to amplification and deep sequencing. Mutant DNA could be accurately and reproducibly measured in a linear manner over approximately 8 orders of magnitude and down to levels as low as 1 in 10,000 molecules (FIG. 6). Also, by testing combinations of DNA from multiple mutant cell lines, the assay was able to simultaneously quantify more than one mutation from a given sample.

Monitoring ctDNA Levels in Cancer Patients

To compare with clinical samples, plasma collected from patients with non-small cell lung cancer (NSCLC) at various times before, during, or after treatment was analyzed. Patients were enrolled in the study (and their plasma DNA was tested) without prior knowledge of the mutation status of their tumors. A total of 117 samples were obtained from 30 patients (17 patients with adenocarcinoma, 9 with undifferentiated NSCLC, and 4 with squamous cell carcinoma). KRAS Gly12Asp, Gly12Val, Gly12Cys, or Gly13Asp point-mutations were detectable in the plasma DNA of 6 patients out of 26 with adenocarcinoma or undifferentiated NSCLC. As expected, no KRAS mutations were found in specimens from patients with squamous cell carcinoma. BRAF and EGFR mutations were not detectable in any plasma samples. This was somewhat surprising for EGFR, which has a reported prevalence of activating mutations in NSCLC of approximately 10% (Lynch et al., *N Engl J Med.* 2004; 350: 2129-2139; Paez et al., *Science.* 2004; 304: 1497-1500; Pao et al., *Proc. Natl. Acad. Sci. USA.* 2004; 101: 13306-13311). However, evaluation of 21 available tumor tissue specimens confirmed the absence of EGFR mutations in this population (mutations occurring outside of the sequenced hotspot region may have been missed). The presence or absence of KRAS mutations in all tested tumor samples was tested to be concordant with the findings in plasma: 5 patients had identical KRAS mutations in both tumor and plasma, and 16 patients had no KRAS mutations detected from either source. Tumor tissue was unavailable or insufficient for 1 patient with mutant KRAS in the plasma, and for 4 patients with no plasma mutations. Table 4 lists the clinical characteristics and mutation findings for all enrolled patients.

TABLE 4

Clinical characteristics and mutation findings.

| Patient No. | Sex | Age | Stage | Plasma Samples | | Tumor Tissue | | |
| | | | | Mutation Type* | No. of Samples | NSCLC Histology | Tissue Source | Tissue Mutation | Method of Mutation Testing |
|---|---|---|---|---|---|---|---|---|---|
| 1 | M | 82 | IV | KRAS WT EGFR WT BRAF WT | 2 | Adeno | Cells in pleural fluid | KRAS WT EGFR WT | Clinical lab |
| 2 | M | 68 | IV | KRAS WT | 2 | Adeno | Lung core | Tissue not available from | |

TABLE 4-continued

Clinical characteristics and mutation findings.

| Patient No. | Sex | Age | Stage | Plasma Samples Mutation Type* | No. of Samples | NSCLC Histology | Tumor Tissue Tissue Source | Tissue Mutation | Method of Mutation Testing |
|---|---|---|---|---|---|---|---|---|---|
| | | | | EGFR WT BRAF WT | | | Bx | outside hospital | |
| 3 | F | 51 | IV | KRAS Gly12Asp EGFR WT BRAF WT | 3 | Adeno | Tracheal Bx | KRAS Gly12Asp EGFR WT BRAF WT | Sanger seq. |
| 4 | M | 71 | IIIB | KRAS WT EGFR WT BRAF WT | 12 | Squam | Para-tracheal lymph node Bx | Not tested (squamous histology) | |
| 5 | M | 44 | IV | KRAS Gly12Val EGFR WT BRAF WT | 5 | Adeno | Lung core Bx | KRAS Gly12Val EGFR WT BRAF WT | Sanger seq. |
| 6 | M | 68 | Lung: IA Prost.: II Esoph.: III | KRAS WT EGFR WT BRAF WT | 13 | Adeno | Lung core Bx | Excess tissue not available | |
| 7 | M | 59 | IIIA | KRAS WT EGFR WT BRAF WT | 8 | Squam | Lung core Bx | Not tested (squamous histology) | |
| 8 | F | 70 | IIIA | KRAS WT EGFR WT BRAF WT | 3 | Adeno | Lung core Bx | KRAS WT EGFR WT BRAF WT | Sanger seq. |
| 9 | M | 72 | IIIB | KRAS Gly12Val EGFR WT BRAF WT | 4 | Undiff | Bronchial brushing | KRAS Gly12Val EGFR WT BRAF WT | Sanger seq. |
| 10 | F | 62 | Lung: IV Breast: I | KRAS WT EGFR WT BRAF WT | 1 | Lung Adeno and Breast Adeno | Iliac wing core Bx | KRAS WT EGFR WT BRAF WT | Sanger seq. |
| 11 | F | 79 | IV | KRAS Gly12Val EGFR WT BRAF WT | 1 | Adeno | Lung fine needle aspirate | KRAS Gly12Val EGFR WT BRAF WT | Sanger seq. |
| 12 | M | 69 | IV | KRAS WT EGFR WT BRAF WT | 3 | Adeno | Scapula mass Bx | KRAS WT EGFR WT | Clinical lab |
| 13 | F | 61 | Lung: IV Breast: I | KRAS WT EGFR WT BRAF WT | 3 | Undiff | Pre-tracheal lymph node needle aspirate | KRAS WT EGFR WT | Clinical lab |

TABLE 4-continued

Clinical characteristics and mutation findings.

| Patient No. | Sex | Age | Stage | Plasma Samples Mutation Type* | No. of Samples | Tumor Tissue NSCLC Histology | Tissue Source | Tissue Mutation | Method of Mutation Testing |
|---|---|---|---|---|---|---|---|---|---|
| 14 | M | 77 | IV | KRAS Gly12Cys EGFR WT BRAF WT | 2 | Adeno | Calf mass excision | KRAS Gly12Cys EGFR WT BRAF WT | Sanger seq. |
| 15 | M | 65 | IV | KRAS Gly13Asp EGFR WT BRAF WT | 2 | Undiff | Bronchial brushing | Excess tissue not available | |
| 16 | F | 73 | IV | KRAS WT EGFR WT BRAF WT | 3 | Undiff | Bronchial Bx | KRAS WT EGFR WT BRAF WT | Sanger seq. |
| 17 | F | 65 | IA | KRAS WT EGFR WT BRAF WT | 5 | Adeno | Lung core Bx | KRAS WT EGFR WT BRAF WT | Sanger seq. |
| 18 | F | 77 | IV | KRAS WT EGFR WT BRAF WT | 1 | Adeno | Lung core Bx | Excess tissue not available | |
| 19 | F | 75 | IV | KRAS WT EGFR WT BRAF WT | 2 | Adeno | Bronchial Bx | KRAS WT EGFR WT | Clinical lab |
| 20 | M | 73 | IB | KRAS WT EGFR WT BRAF WT | 5 | Squam | Lung lobectomy | Not tested (squamous histology) | |
| 21 | M | 73 | IIB | KRAS WT EGFR WT BRAF WT | 4 | Adeno | Lung core Bx | KRAS WT EGFR WT BRAF WT | Sanger seq. |
| 22 | F | 68 | IV | KRAS WT EGFR WT BRAF WT | 3 | Undiff | Lung tumor excision | KRAS WT EGFR WT | Clinical lab |
| 23 | F | 79 | IA | KRAS WT EGFR WT BRAF WT | 3 | Undiff | Lung core Bx | Tissue not available from outside hospital | |
| 24 | M | 64 | IIIB | KRAS WT EGFR WT BRAF WT | 8 | Squam | Lung core Bx | Not tested (squamous histology) | |

TABLE 4-continued

Clinical characteristics and mutation findings.

| Patient No. | Sex | Age | Stage | Plasma Samples Mutation Type* | No. of Samples | NSCLC Histology | Tumor Tissue Tissue Source | Tissue Mutation | Method of Mutation Testing |
|---|---|---|---|---|---|---|---|---|---|
| 25 | F | 73 | Locally recur. IB | KRAS WT EGFR WT BRAF WT | 8 | Undiff | Lung lobectomy | KRAS WT EGFR WT BRAF WT | Sanger seq. |
| 26 | F | 63 | IIIB | KRAS WT EGFR WT BRAF WT | 1 | Adeno | Lung core Bx | KRAS WT EGFR WT BRAF WT | Sanger seq. |
| 27 | F | 74 | IIIA | KRAS WT EGFR WT BRAF WT | 4 | Undiff | Paratracheal lymph node Bx | KRAS WT EGFR WT BRAF WT | Sanger seq. |
| 28 | F | 61 | IV | KRAS WT EGFR WT BRAF WT | 3 | Adeno | Spine Met Bx | KRAS WT EGFR WT BRAF WT | Sanger seq. and Clinical lab |
| 29 | F | 82 | IV | KRAS WT EGFR WT BRAF WT | 2 | Undiff | Lung core Bx | KRAS WT EGFR WT BRAF WT | Sanger seq. and Clinical lab |
| 30 | F | 69 | Lung: IV Breast: IV | KRAS WT EGFR WT BRAF WT | 1 | Adeno | Lung fine needle aspirate | KRAS WT EGFR WT BRAF WT | Sanger seq. |

The list is ordered by date of first specimen collection.
*Plasma DNA was only tested for mutations at codons 12 and 13 of KRAS, 858 of EGFR, and 600 of BRAF.
Squam = Squamous cell carcinoma
Adeno = Adenocarcinoma
Undiff = Undifferentiated NSCLC (not otherwise specified)
WT = Wild-type
Bx = Biopsy
Sanger Seq. = Direct Sanger sequencing of tissue-derived PCR amplicons by our laboratory.
Clinical lab = Mutations tested for clinical purposes in a laboratory certified under the Clinical Laboratory Improvement Amendments of 1988 (CLIA). Tissue was not tested for BRAF mutations by clinical laboratories because of low prevalence in NSCLC.

Figure 8:
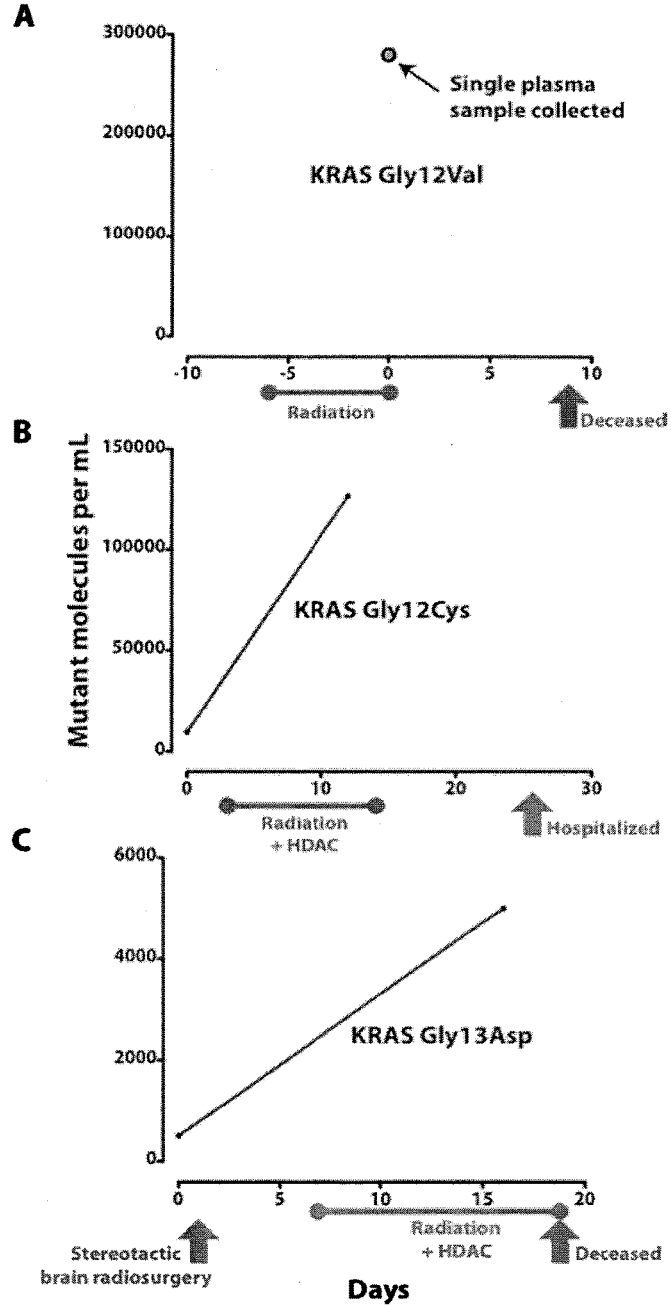
FIGS. 8A-C show the ctDNA levels in patients with fewer than 3 time-points.

For patients with detectable plasma DNA mutations, changes in measured ctDNA levels were followed in the context of therapeutic interventions or disease progression. To determine the absolute concentration of mutant KRAS DNA fragments in a plasma sample, the total concentration of KRAS fragments was measured by real-time PCR and then multiplied by the fraction of mutant molecules determined by deep sequencing. The median concentration among samples with detectable mutations was 5,694 mutant KRAS molecules per mL (IQR: 2,655 to 25,123). Timecourses of mutant ctDNA measurements for patients who had 3 or more samples collected are shown in FIG. 7 (data for patients with fewer measurements are shown in FIG. 8). In two cases, the ctDNA level decreased upon treatment with radiation and/or systemic therapy. Aggressive progression of metastatic disease in a different patient was accompanied by a substantial rise in ctDNA. In another two cases, ctDNA levels increased shortly after initiating treatment, perhaps because more tumor DNA was released into the bloodstream as cancer cells were being killed.

Example 2

Figure 11:
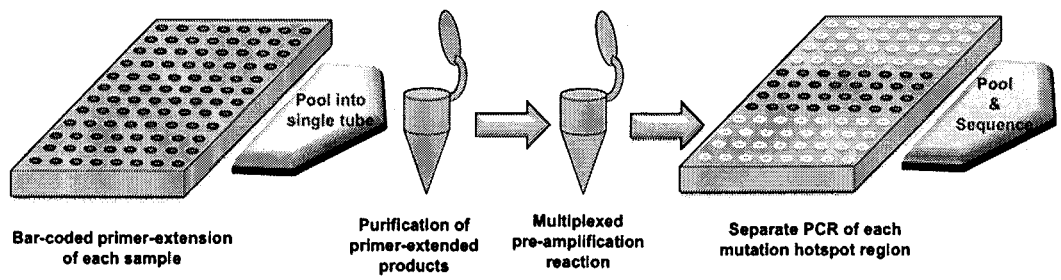
FIG. 11 shows a workflow of a process described in Example 2. Separate primer-extension reactions were initially carried out for each sample. Barcoded products were then be mixed into a single volume for purification and pre-amplification steps. Purified products were then split into separate tubes and underwent final single-target PCR in separate reaction volumes.
Figure 12:
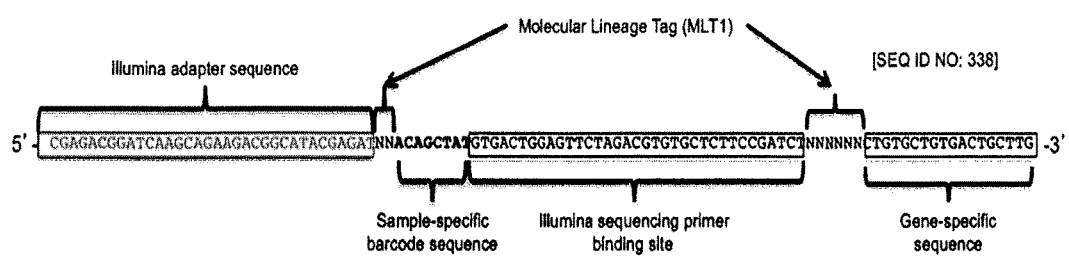
FIG. 12 shows an example of a Round 1 reverse primer sequence, highlighting various elements of the sequence. Note that the gene-specific sequence at the 3'-end can act as a primer for either PCR or primer-extension by a DNA polymerase. The 5'-segment contains a sample-specific barcode sequence, a Molecular Lineage Tag (MLT), as well as adapter sequences required by the next-generation sequencing platform. In this example, a gene-specific segment is specific for a mutation prone-region of TP53. For Round 1 PCR or primer-extension of a given sample, a mixture of several reverse primers would be used, all having the same sample-specific barcode sequence, and multiple different gene-specific sequences. A similar mixture, but with another barcode, would be used for Round 1 PCR or primer-extension of a different sample.

This example includes methods that incorporate elements of Example 1, but also includes several modifications. (FIGS. 10 and 11). In this example, 40 different genomic target regions were analyzed. Of the 40 genomic target regions, 38 were prone to developing somatic mutations, and 2 were included as controls that were not expected to be mutated.

Figure 3:
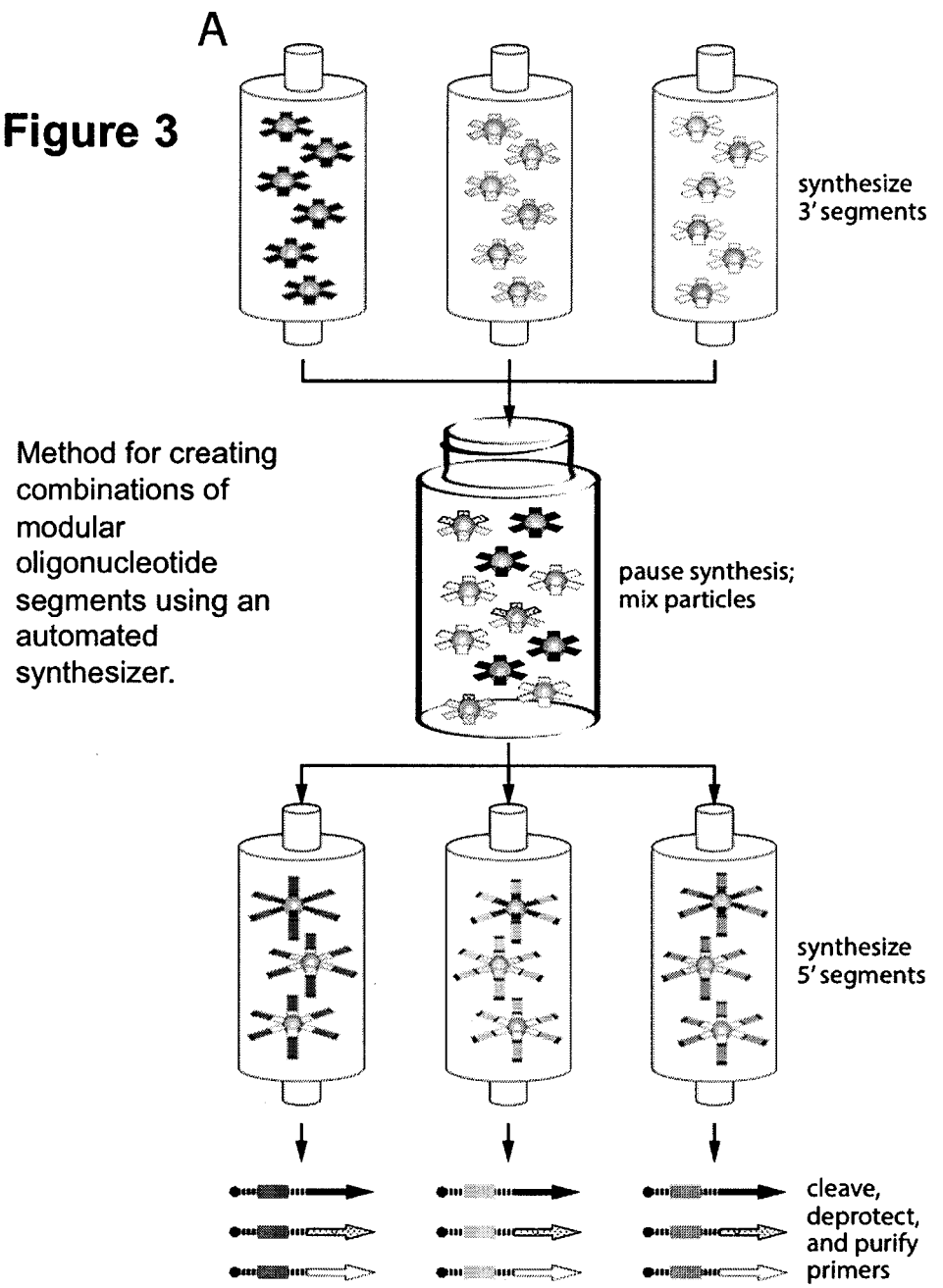
FIG. 3 illustrates a method for producing combinations of modular oligonucleotide segments using an automated oligonucleotide synthesizer. First, gene-specific 3'-segments of oligonucleotides were synthesized on solid supports on separate synthesis columns. The oligonucleotides were synthesized in a 3' to 5' direction. The synthesis was then paused, and the partially-synthesized oligonucleotides were left in a protected state on solid support particles. The contents of all columns were evenly mixed, and the mixture of solid support particles was then dispensed into separate fresh columns. Synthesis of the barcode-containing 5'-segment of the oligonucleotides was then continued in the new columns. A uniquely barcoded 5'-segment was added in each column. After cleavage, deprotection and purification, the resulting barcoded oligonucleotide mixtures all had identical ratios of 3'-segments.

Preparation of Mixtures of Primers Having Combinations of Modular Oligonucleotide Segments As described previously, early tagging of targeted DNA template molecules required the production of mixtures of primers having a common barcode in their 5' region, and having several different gene-specific primer segments at their 3' end. Herein modular oligonucleotide segments were combined during oligonucleotide synthesis on an automated synthesizer, "modular automated synthesis and purification", and the approach is illustrated in (FIG. 3).

Each different gene-specific 3'-portion was synthesized on separate oligonucleotide synthesis columns. Standard phosphoramidite chemistry was used, and the oligonucleotides were grown on a solid support. Both polystyrene and controlled-pore-glass were used as solid supports, but polystyrene was preferable. Both types of supports performed similarly. The solid support consisted of small particles that appeared as a powder. The powder was contained within an oligonucleotide synthesis column, sandwiched loosely between two frits. Multiple different 3'-segments were grown (oligomerized by chemical coupling of phosphoramidite monomers) in separate synthesis columns on an automated synthesizer in the 3' to 5' direction. The synthesis was paused, and partially synthesized oligonucleotides were left on the column in the protected state with the trityl group left on.

"Pipette tip"-style oligonucleotide synthesis columns were utilized with sufficient controlled-pore glass (1000 angstrom pore size) or polystyrene to synthesize oligos at the 40 nanomole or 200 nanomole scale (3-Prime, Aston, Pa.). Forty different partial 3' oligonucleotide segments were synthesized on 40 separate columns using a Dr. Oligo 192 automated synthesizer. The oligonucleotides were not cleaved from the solid supports, were not deprotected, and the trityl group was left on so that further synthesis could be continued. The sequences of these 40 different 3' segments are listed in Table 5.

TABLE 5

List of forty 3'oligonucleotide segments synthesized in separate columns for first phase of modular automated synthesis.

| Name | DNA Sequence | SEQ ID NO: |
|---|---|---|
| 3'segment1 | AGACGTGTGCTCTTCCGATCTNNNNNNCTGTGCTGTGACTGCTTG | 52 |
| 3'segment2 | AGACGTGTGCTCTTCCGATCTNNNNNNTAGCACATGACGGAGGTT | 53 |
| 3'segment3 | AGACGTGTGCTCTTCCGATCTNNNNNNACAAATACTCCACACGCAAATT | 54 |
| 3'segment4 | AGACGTGTGCTCTTCCGATCTNNNNNNATATTTGGATGACAGAAACACTT | 55 |
| 3'segment5 | AGACGTGTGCTCTTCCGATCTNNNNNNCTGTGATGATGGTGAGGATGG | 56 |
| 3'segment6 | AGACGTGTGCTCTTCCGATCTNNNNNNCTGGGACGGAACAGCTTTGAG | 57 |
| 3'segment7 | AGACGTGTGCTCTTCCGATCTNNNNNNTGCAATTTCTACACGAGATCCTCT | 58 |
| 3'segment8 | AGACGTGTGCTCTTCCGATCTNNNNNNTCTTTGGAGTATTTCATGAAACAAATGA | 59 |
| 3'segment9 | AGACGTGTGCTCTTCCGATCTNNNNNNAACAGTAAAAATAGGTGATTTTGGTCTA | 60 |
| 3'segment10 | AGACGTGTGCTCTTCCGATCTNNNNNNTGCAACTACTGGACGCTGGAC | 61 |
| 3'segment11 | AGACGTGTGCTCTTCCGATCTNNNNNNCTCAATTTTGTTTCAGGACCTGCT | 62 |
| 3'segment12 | AGACGTGTGCTCTTCCGATCTNNNNNNCTGGCAGCAACAGTCTTACCT | 63 |
| 3'segment13 | AGACGTGTGCTCTTCCGATCTNNNNNNACCC AGC TTG GAG GCT GC | 64 |
| 3'segment14 | AGACGTGTGCTCTTCCGATCTNNNNNNAGCCAGGCCGCTGAAGACA | 65 |
| 3'segment15 | AGACGTGTGCTCTTCCGATCTNNNNNNGGCAATTCACTGTAAAGCTGGAAAG | 66 |
| 3'segment16 | AGACGTGTGCTCTTCCGATCTNNNNNNATGAAGATATATTCCTCCAATTCAGGAC | 67 |
| 3'segment17 | AGACGTGTGCTCTTCCGATCTNNNNNNGCGTTTCCTTTAACCACATAATTAGAATC | 68 |

TABLE 5-continued

List of forty 3'oligonucleotide segments synthesized in separate columns for first phase of modular automated synthesis.

| Name | DNA Sequence | SEQ ID NO: |
|---|---|---|
| 3'segment18 | AGACGTGTGCTCTTCCGATCTNNNNNNGTTTTCCCTTTCTCCCCACAG | 69 |
| 3'segment19 | AGACGTGTGCTCTTCCGATCTNNNNNNGTTCCTGTAGCAAAACCAGAAATC | 70 |
| 3'segment20 | AGACGTGTGCTCTTCCGATCTNNNNNNCGGTGAGAAAGTTAAAATTCCCGTC | 71 |
| 3'segment21 | AGACGTGTGCTCTTCCGATCTNNNNNNAAGCATGTCAAGATCACAGATTTTG | 72 |
| 3'segment22 | AGACGTGTGCTCTTCCGATCTNNNNNNCTCACCTCCACCGTGCAGCT | 73 |
| 3'segment23 | AGACGTGTGCTCTTCCGATCTNNNNNNGACCACCCGCACGTCTGT | 74 |
| 3'segment24 | AGACGTGTGCTCTTCCGATCTNNNNNNTCTTCCATACTTGATTCATGATATTTTACT | 75 |
| 3'segment25 | AGACGTGTGCTCTTCCGATCTNNNNNNGACCTCCTCAAACAGCTCAAAC | 76 |
| 3'segment26 | AGACGTGTGCTCTTCCGATCTNNNNNNATGGGAGATCTTCACGCTGG | 77 |
| 3'segment27 | AGACGTGTGCTCTTCCGATCTNNNNNNTCCCTGAGCGTCATCTGCC | 78 |
| 3'segment28 | AGACGTGTGCTCTTCCGATCTNNNNNNCGCTGGTGGAGGCTGACGA | 79 |
| 3'segment29 | AGACGTGTGCTCTTCCGATCTNNNNNNGTTCCCTATCAAATATGTCAACGACT | 80 |
| 3'segment30 | AGACGTGTGCTCTTCCGATCTNNNNNNAATTTTGGTCTTGCCAGAGACA | 81 |
| 3'segment31 | AGACGTGTGCTCTTCCGATCTNNNNNNTATCGACTCCACCGAGGTCA | 82 |
| 3'segment32 | AGACGTGTGCTCTTCCGATCTNNNNNNATACTTGGAGGACCTGCACG | 83 |
| 3'segment33 | AGACGTGTGCTCTTCCGATCTNNNNNNGTCGTCAAGGCACTCTTGCCT | 84 |
| 3'segment34 | AGACGTGTGCTCTTCCGATCTNNNNNNCGATATTCTCGACACAGCAGGT | 85 |
| 3'segment35 | AGACGTGTGCTCTTCCGATCTNNNNNNATCAGTGCGCTTTTCCCA | 86 |
| 3'segment36 | AGACGTGTGCTCTTCCGATCTNNNNNNTGACATACTGGATACAGCTGGA | 87 |
| 3'segment37 | AGACGTGTGCTCTTCCGATCTNNNNNNGTGGTCAGCGCACTCTTGCCC | 88 |
| 3'segment38 | AGACGTGTGCTCTTCCGATCTNNNNNNTCATCCTGGATACCGCCGGC | 89 |
| 3'segment39 | AGACGTGTGCTCTTCCGATCTNNNNNNATCCTGTTTATAATATTGACAAAACACCT | 90 |
| 3'segment40 | AGACGTGTGCTCTTCCGATCTNNNNNNATCAGGACAAAGTCCGGATTGA | 91 |

These oligonucleotides were synthesized at the 200 nanomole scale, with the oligo left on the column in the protected state with the trityl group left on. Positions marked "N" have equal probability of being A, C, G, or T.

The solid supports of all 40 partially synthesized oligonucleotides were dried by blowing argon gas through the columns, and then the controlled-pore glass or polystyrene powder from all 40 columns was mixed by pouring the contents of each column (after cutting the tops off of the columns) into a common container (such as a glass vial). The solid support particles were then suspended in a solvent of similar density so that the particles could be thoroughly mixed and then the mixture could be dispensed into fresh oligonucleotide synthesis columns. When using polystyrene supports, a 3:1 mixture of dichloromethane:acetonitrile was used as the suspension liquid, and when using controlled-pore glass supports, a 5:1 mixture of 1,2-dibromoethane:acetonitrile was used as the suspension liquid. The particles were maintained as a uniform slurry in the liquid by constantly swirling or agitating the vial while using a pipette to dispense equal volumes of the slurry into fresh columns (with the bottom frit already in place). The slurry was dispensed into 96 fresh columns. The particles settled onto the frits, while the liquid drained out from the bottom of the columns by gravity. To ensure that the particles had all settled onto the frit, the columns were filled with acetonitrile and this was again allowed to drain out from the bottom by gravity. After the acetonitrile had fully drained out, the top frits were put in place to secure the powder into the columns.

The new columns were then placed back on the automated synthesizer, and the oligonucleotide synthesis was continued. Each column was assigned a different barcode sequence that was incorporated into the 5' oligonucleotide segment. A "dummy base" was added to the 3' end of the 5' segment sequence when programming the synthesizer in order to account for the partially synthesized oligonucleotides that were already present on the solid supports. The sequences of the 96 different 5' segments consisted of the following common sequence with each of 96 different barcodes inserted in the position marked [BC1-96]. One unique barcode was used per oligonucleotide synthesis column.

```
                                              (SEQ ID NO: 92)
5'-CGAGACGGATCAAGCAGAAGACGGCATACGAGATNN[BC1-
96]GTGACTGGAGTTC(T)-3'
```

The "T" in parentheses at the 3'-end of the sequence is the "dummy base". The 96 barcodes that were used are listed in Table 6. The automated synthesizer was programmed to carry out synthesis at a 40 nmole scale (which determines the volume of reagents passed through the columns), although the actual amount of solid support in each column was likely to produce less than 40 nmoles of oligonucleotides.

TABLE 6

List of 96 sample-specific barcodes

| Barcode # | Sequence (BBBBBBBB) |
|---|---|
| 1 | CCGATATT |
| 2 | GCCATATT |
| 3 | TCTGGATT |
| 4 | ACTCGATT |
| 5 | TCACGATT |
| 6 | ACTGCATT |
| 7 | TCAGCATT |
| 8 | TCTCCATT |
| 9 | ATTGGTGT |
| 10 | TTAGGTGT |
| 11 | ATACGTGT |
| 12 | ATAGCTGT |
| 13 | ATTCCTGT |
| 14 | TTACCTGT |
| 15 | CTCTATGT |
| 16 | CTCTTAGT |
| 17 | CTGATAGT |
| 18 | GTCATAGT |
| 19 | ATAGGAGT |
| 20 | ATTCGAGT |
| 21 | TTACGAGT |
| 22 | ATTGCAGT |
| 23 | TTAGCAGT |
| 24 | ATACCAGT |
| 25 | AGTGGTCT |
| 26 | TGAGGTCT |
| 27 | TGTCGTCT |
| 28 | TGTGCTCT |
| 29 | AGTCCTCT |
| 30 | TGACCTCT |
| 31 | CGCTATCT |
| 32 | CGCTTACT |
| 33 | CGGATACT |
| 34 | GGCATACT |
| 35 | TGTGGACT |
| 36 | AGTCGACT |
| 37 | TGACGACT |
| 38 | AGTGCACT |
| 39 | TGAGCACT |
| 40 | TGTCCACT |

TABLE 6-continued

List of 96 sample-specific barcodes

| Barcode # | Sequence (BBBBBBBB) |
|---|---|
| 41 | TCATTGTG |
| 42 | TCTATGTG |
| 43 | ACTATCTG |
| 44 | ACTTACTG |
| 45 | TCATACTG |
| 46 | ATTATCGG |
| 47 | TTATACGG |
| 48 | TGATTGCG |
| 49 | TGTATGCG |
| 50 | AGTATCCG |
| 51 | AGTTACCG |
| 52 | TGATACCG |
| 53 | ACTATGTC |
| 54 | ACTTAGTC |
| 55 | TCATAGTC |
| 56 | TCATTCTC |
| 57 | TCTATCTC |
| 58 | ATTATGGC |
| 59 | TTATAGGC |
| 60 | TTATTCGC |
| 61 | AGTATGCC |
| 62 | AGTTAGCC |
| 63 | TGATAGCC |
| 64 | TCTGGTTA |
| 65 | TCACGTTA |
| 66 | TCAGCTTA |
| 67 | TCTCCTTA |
| 68 | CCGTATTA |
| 69 | GCCTATTA |
| 70 | CCGTTATA |
| 71 | GCCTTATA |
| 72 | TCAGGATA |
| 73 | TCTCGATA |
| 74 | TCTGCATA |
| 75 | TCACCATA |
| 76 | CTGATTGA |
| 77 | GTCATTGA |
| 78 | TTACGTGA |
| 79 | TTAGCTGA |
| 80 | CTGTATGA |
| 81 | GTCTATGA |
| 82 | CGGATTCA |
| 83 | GGCATTCA |
| 84 | TGTGGTCA |
| 85 | TGACGTCA |
| 86 | TGAGCTCA |
| 87 | TGTCCTCA |
| 88 | CGGTATCA |
| 89 | GGCTATCA |
| 90 | CGGTTACA |
| 91 | GGCTTACA |
| 92 | CGCATACA |
| 93 | TGAGGACA |
| 94 | TGTCGACA |
| 95 | TGTGCACA |
| 96 | TGACCACA |

After completion of the second phase of the modular synthesis, the oligos were cleaved off the solid supports with the trityl group still left on. They underwent rapid deprotection followed by purification on a separate Glen-Pak DNA reverse-phase cartridge for each of the 96 oligonucleotide mixtures (Glen Research, Sterling, Va.). The trityl group at the 5'-end of completed oligonucleotides was selectively retained by the cartridge, enriching for full-length products and removed failure sequences that did not contain the trityl group. The trityl group was removed upon completion of purification. The purified oligonucleotides were then dried and re-suspended in 10 mM Tris pH 7.6 to produce a 33 micromolar working stock solution. Polyacrylamide gel purification was used in some cases to further purify the full-length oligonucleotides.

Collection and Processing of Patient Plasma Samples

Blood was collected by venipuncture into a vacuum tube containing potassium-EDTA. Various tube sizes were used, typically between 3 mL and 10 mL. Blood was inverted in the tube several times at the time of collection to ensure even mixing of the $K_2$-EDTA. Samples were stored temporarily and transported at room temperature (20-25° C.) prior to separation of plasma. Plasma was separated and frozen as soon as possible after blood collection, preferably within 3 or 4 hours. The collection tubes were centrifuged at 1000×g for 10 minutes in a clinical centrifuge with a swinging bucket rotor with slow acceleration and deceleration (brake off). Plasma was removed from the red blood cells and buffy coat using a 1 mL pipette, being careful not to disturb the cells at the bottom of the tube (to avoid aspirating white blood cells which would lead to increased background wild-type DNA levels). The plasma was dispensed into 1.5 mL cryovials in 0.5 to 1 mL aliquots. The plasma was then frozen at −80° C. until needed for further processing.

Extraction and Purification of DNA from Plasma

Plasma was removed from the −80° C. freezer and was thawed at room temperature for 15 to 30 minutes before proceeding with DNA extraction. Thawed plasma was then centrifuged at 6800×g for 3 minutes to remove any cryoprecipitate. The supernatant was transferred to a fresh tube for further processing.

The QiaAmp® DNA Blood Mini Kit (Qiagen) was used for purification from plasma volumes up to 200 μL (elution volume of 50 μL), and the QiaAmp® MinElute® Virus Vacuum Kit (Qiagen) has also been used for plasma volumes up to 1 mL (elution volume as low as 20 μL). For larger volumes of a particular sample of plasma, more than one column of the QiaAmp® MinElute® Virus Vacuum Kit was used for purification. All kits were used according to the manufacturer's instructions, generally eluting the DNA into the lowest recommended volume (preferably 20 μL). To process 1 mL of plasma using the QiaAmp® MinElute® Virus Vacuum Kit, 5 micrograms of carrier RNA (cRNA; Qiagen) were added per mL, and the user-developed protocol found on the Qiagen website was followed.

Primer-Extension Reaction

Specific mutation-prone regions of purified, plasma-derived template DNA molecules were copied using targeted gene-specific primers. The number of different gene-specific primer sequences used in each tube depended on the number of targeted DNA regions within the genome. A combination of 40 different gene-specific primers were used in each sample to target 40 different gene regions. As described previously, each set of gene-specific primers had a unique, sample-specific DNA sequence (a barcode) near the 5'-end of the primers that were incorporated in a modular fashion. Each sample underwent primer-extension using an approximately equimolar concentration of 40 different gene-specific primers, all of which had the same sample-specific barcode. These primers also included degenerate sequence regions known as molecular lineage tags (MLTs) as well as common sequences at the 5'-end that allowed for hybridization of "universal" PCR primers in subsequent steps.

Control DNA molecules containing known mutations were spiked into each primer extension reaction to serve as internal quantitative standards. These DNA molecules were cartridge-purified oligonucleotides that were synthesized to contain variations from the wild-type sequence at two distinct positions (which would be extremely unlikely to occur in plasma-derived DNA). These variations allowed the control sequences to be readily distinguished from other variants within DNA purified from a clinical sample. The sequences of the top strands of these control DNA oligonucleotides are listed in Table 7. Reverse complements of these 40 sequences were also separately synthesized to produce bottom strands. In order to make the control DNA as similar as possible to the clinically-derived DNA, both strands were annealed to make them double-stranded before adding them to the primer-extension reaction. The double-stranded DNA was quantified by UV spectrometry and then diluted to the desired concentration. To each primer-extension reaction, approximately 200 copies of the double-stranded control DNA fragments corresponding to each of the 40 gene target sites were added.

TABLE 7

List of spiked-in quantitative standard oligonucleotides containing mutations at 2 distinct sites relative to wild-type.

| Name | DNA Sequence | SEQ ID NO: |
|---|---|---|
| CFTP-1 | TCAACAAGATGTTTTGCCAACTGGCCAAGACCTGCCC TGTGCAGCTGTGGGTTGATTCCACACCCCCGCCCGGC ACCCGCGTCCGCGTCATGACCATCTACAAGCAGTCAC AGCACATGA | 93 |
| CFTP-2 | TCACAGCACATGACGGAGGTTGTGAGGCGCTGCCACC ACCATGTGCGCTGCTCAGATAGCGATGGTGAGCAGCT GGGGCTGGAGAGACGACAGGGCTG | 94 |
| CFTP-3 | ACAGGGCTGGTTGCCCAGGGTCCCCAGGCCTCTGATT CCTCACTGATTGCTCTTAGGTCTGGCCCCTCCTCAGCA TCATATCCGAGTCGAAGGAAATTTGCGTGTGGAGTAT TTGGATG | 95 |
| CFTP-4 | GAGTATTTGGATGACAGAAACACTTTTCGACACAGTG TGGTGATGCCCTATGAGCCGCCTGAGGTCTGGTTTGC AACTGGGGTCTCTGGGAGGAGGGGTTAAGGGTGGTT GTCAGTGGCCCTC | 96 |
| CFTP-5 | CTGGCCTCATCTTGGGCCTGTGTTATCTCCTAGGTTGG CTCTGACTGTACCACCATCCACTACAACGACATGTGT AACTGTTCCTGCATGGGCGGCATGAACCGGAGGCCCA TCCTCACCATCATCACACTGG | 97 |
| CFTP-6 | TACTGGGACGGAACAGCTTTGAGGTGCGTGTTTGTGC ATGTCCTGGGACAGACCGGCGCACAGAGGAAGAGAA TCTCCGCAAGAAAGGGGAGCCTCACCACGAGCTGCC CCCAG | 98 |
| CFPIK-1 | CAAAGCAATTTCTACACGAGATCCTCTCTCTGAAGTC AGTGAGCAGGAGAAAGATTTTCTATGGAGTCACAGG TAAGTGCTAAAATGGAGATTCTCTGTTTCTTTTTC | 99 |
| CFPIK-2 | GAGGCTTTGGAGTATTTCATGAAACAAATGAATCATA CACATCATGGTGGCTGGACAACAAAAATGGATTGGA TCTTCCACACAATTAAACAGCATGCATTGAACTGAAA AG | 100 |
| CFBRAF | CCTCACAGTAAAAATAGGTGATTTTGGTCTAGCGACA GTGAAAGCTCATGGGAGTGGGTCCCATCAGTTTGAAC AGTTGTCTGGATCCATTTTGTGGATGGTAAGAATT | 101 |
| CFFox | AAGGGCAACTACTGGACGCTGGACCCGACCTGCGCA GACATGTTCGAGAAGGGCAACTACCGGCGCCGCCGC CGCATGAAGAGGCCCTTCCGGCCG | 102 |
| CFGNAS | ACCTCAATTTTGTTTCAGGACCTGCTTCACTGCCGTAT CCTGACTTCTGGAATCTTTGAGACCAAGTTCCAGGTG GACAAAGTCAACTTCCAGTAAGCCAACT | 103 |
| CFCTNN | CACTGGCAGCAACAGTCTTACCTGGACTCTGGAATCC ATTCTGATGCCACTACCACAGATCCTTCTCTGAGTGG TAAAGGCAATCCTGAGGAAGAGGATGTGGATACCTC CCAAGTCCTGTAT | 104 |
| CFPPP-1 | CTGCCTGCTGCCTCAGGATCCCCGTCCCCGACTCCCA GGTACTTCCGGAACCTGTGCTCAGATGACACCCCCAC GGTGCGGCGGACCGCAGCCTCCAAGCTGGGGGAG | 105 |
| CFPPP-2 | CTGCGCCAGGCCGCTGAAGACAAGACCTGGCGCATC CGCTACATGGTGGCTGACAAGTTCACAGAGGTAGATG AGCGACCGTTGACATTGTCCCACTGGT | 106 |
| CFPTEN-1 | TGCAGCAATTCACTGTAAAGCTGGAAAGGGACGAAC AGGTGTAATGACATGTGCATATTTATTACATCGGGGC AAATTTTTAAAGGCACAAGAGGCCCTAGATTTCTATG GGGAAG | 107 |
| CFPTEN-2 | AGGTGAAGATATATTCCTCCAATTCAGGACCCTCACG ACGGGTAGACAAGTTCATGTACTTTGAGTTCCCTCAG CCGTTACCTGTGTGTGGTGATATCAAAGTAGAGTTCT | 108 |

TABLE 7-continued

List of spiked-in quantitative standard oligonucleotides containing mutations at 2 distinct sites relative to wild-type.

| Name | DNA Sequence | SEQ ID NO: |
|---|---|---|
| CFKIT-1 | GAGACTTGGCAGCCAGAAATATCCTCCTTACTCATGG TCGGATCACAAAGATTTGTGATTTTGGTCTAGCCATA GACATCACGAATGATTCTAATTATGTGGTTAAAGGAA ACGTGAG | 109 |
| CFKIT-2 | TATTTTTCCCTTTCTCCCCACAGAAACCTATGTATGAA GTACAGTGGAAGGATGTTGAGGAGATAAATGGAAAC AATTATGTTTACATAGACCCAACACAACTTCCTTATG ATCACAAATGGGAGTTTC | 110 |
| CFKIT-3 | GTTTTCCTGTAGCAAAACCAGAAATCCTGACTTACGA CAGGCTAGTGAATGGCATGCTCCAATGTGTGGCAGCA GGATTCCCAGAGCCCACAATAGATTGGTATTTTT | 111 |
| CFEG-1 | AGAAGGTGAGAAAGTTAAAATTCCCGTCGCTATGAA GGAATTAAGAGAAGCAACATCTCCGTAAGCCAACAA GGAAATCCTCGATGTGAGTTTCTGCTTTGCTGTGTGG GGGTC | 112 |
| CFEG-2 | CCGCAGCATGTCAAGATCACAGATTTTGGGCTGGACA AACAGCTGGGTGCGGAAGAGAAAGAATACCATGCAG AAGGAGGCAAAGTAAGGAGGTGGCTTTAG | 113 |
| CFEG-3 | GCCTCACCTCCACCGTGCAGCTCATGACGTAGCTCAT GCCCTTCGGCTGCCTCCTGGACTATGTCCGGGAACAC AAAGACAATA | 114 |
| CFAKT1 | TCTCACCACCCGCACGTCTGTAGAGGACTACATCAAG ACCTGGCGGCCACGCTACTTCCTCCTCAAGAATGATG GCACCTTCATTGG | 115 |
| CFATM | TGTACTTCCATACTTGATTCATGATATTTTACTCCTAG ATACGAATGAATCATGGAGAAATCTGCTTTCTACACA TGTTCAGGGATTTTTCACCAGCTGTCTTCGACACTTCT CGC | 116 |
| CFAPC | CACCACCTCCTCAAACAGCTCAAACCATGCGATAAGT ACCTAAAAATAAAGCACCTACTGCTGAAAAGAGAGA GAGTGGACCTAAGCAAGCTGCAGT | 117 |
| CFFGFR-1 | GCTCTGGGAGATCTTCACGCTGGGGACTCCCCGTAT CCCGGCATCCCTGTGGAGGAGCTCTTCAAGCTGCTGA AGGAGGGCACCGCATGGACAAGCCCGCCA | 118 |
| CFFGFR-2 | TGGCCCCTGAGCGTCATCTGCCCCCACTGAGCGCTCC ACGCACCGGCCCATCCTGCAGGCGGGGCTGCCGGCC AACCAGACGGCGGTGCTGGGCAGCGACGTGGAGTTCC | 119 |
| CFFGFR-3 | AGGAGCTGGTGGAGGCTGACGAGGCGGGCAGTATGT ATACAGGCATCCTCAGCTACGGGGTGGGCTTCTTCCT GTTCATCCTGGTGGTGGCGGCTGTGAC | 120 |
| CFMET-1 | GCATTCCCTATCAAATATGTCAACGACTTCATCAACA AGATAGTCAACAAAAACAATGTGAGATGTCTCCAGC ATTTTTACGGACCCAATCATGAGCACTGCTTTAATAG GGTAA | 121 |
| CFMET-2 | GCTGATTTTGGTCTTGCCAGAGACATGTATCATAAAC AATACTATAGTGTACACAACAAAACAGGTGCAAAGC TGCCAGTGAAGTGGATGGCTTTGGAAAGTCTG | 122 |
| CFSTK-1 | CCGCATCGACTCCACCGAGGTCATCTACCAGCCGAGC CGCATGCGGGCCAAGCTCATCGGCAAGTACCTGATGG GGGACCTGCTGGGGAAGGCTCTTACGGCAAGGTGA AGGAGGTGCTGGACTCGGAG | 123 |
| CFSTK-2 | CCGTACTTGGAGGACCTGCACGGCGCGGATGAGGAC GAGGACCACTTCGACATCGAGGATGACATCATCTACA CTCAGGACTTCACGGTGCCCGGTGAGTCTGGCGGGGG | 124 |
| CFKRAS-1 | TATAGTCACATTTTCATTATTTTTATTATAAGGCCTGC TGAAAATGACTGAATATAAACTTGTGGTAGTTGCAGA TGGTGGCGTAGGCAAGAGTGCCTTGACGATAC | 125 |
| CFKRAS-2 | CTTGGATATTCTCGACACAGCAGGTCAAGACGAGTAC TGTGCAATGAGGGACCAGTACATGAGGACTGGGGAG GGCTTTCTTTGTGTATTTGCCATAAATAATACTAAA | 126 |
| CFNRAS-1 | TGTAGATGTGGCTCGCCAATTAACCCTGATTACTGGT TTCCAACAGGTTCTTGCTGGTGTGAAATGACTGAGTA CAAACTGGTCGTGGATGGAGCAGGTGGTGTTGGGAA AAGCGCACTGACAAT | 124 |
| CFNRAS-2 | GTTGGACATACTGGATACAGCTGGACAAGAAGAGCA CAGTGACATGAGAGACCAATACATGAGGACAGGCGA AGGCTTCCTCTGTGTATTTGCCATCAATAATAGCAAG TCAT | 128 |
| CFHRAS-1 | GGTGGGGCAGGAGACCCTGTAGGAGGACCCCGGGCC GCAGGCCCTGAGGAGCGATGACGGAATATAAGCTG GTGGTCGTGGACGCCGGCGGTGTGGGCAAGAGTGCG CTGACCATCC | 129 |
| CFHRAS-2 | TGGACATCCTGGATACCGCCGGCCAGGAGTACTACAG CGCCATGCGGGACCAGTACATGCGCACCGGGGAGGG CTTCCTGTGTGTGTTTGCCATCAACAACACCAAGTCTT TTGAGGA | 130 |
| CFK-Ctrl | TGTTCCTGTTTATAATATTGACAAAACACCTTAGCGG ATGACATTTAAGAATTCTAAAAGTCCTAATATATGTA ATATATATTCAGTTGCCTGAAGAGAAACATAAAGAAT CCTTTCTTAAT | 131 |
| CFB-Ctrl | ATGTCAGGACAAAGTCCGGATTGAATATAACTCTGCT TTATATTATAGGCCTATGAAGAATACACCAGCAAGCT AGATGCACTCCAACAAAGAGAACAACAGTTATTGGA ATCTCTGGG | 132 |

*All oligos synthesized at 40 nmole scale with cartridge purification.

Conditions were optimized so that on average, more than one copy of each original DNA template molecule would be present at the beginning of the next amplification step. Typically between 2 and 10 cycles of primer-extension were carried out. Primer extension was performed using Accuprime Taq polymerase (Invitrogen) as described below.

Primer-Extension Reaction Setup (30 μL Reaction):

| | |
|---|---|
| Purified template DNA (with co-eluted carrier RNA [cRNA]) | 20 μL (or less) |
| 100 copies of control mutant DNA in 10 mM Tris (with 300 ng per mL cRNA) | (as needed) |
| 10 mM Tris with cRNA (300 ng per mL) | (as needed for final 30 μL volume) |
| 10 x concentrated Accuprime Buffer #2 | 3 μL |
| Mix of 40 modular barcoded primers (50 μM total stock) (final ~200 nM each) | 4.8 μL |
| Accuprime Taq polymerase | 0.6 μL |
| Total | 30 μL |

Temperature Cycling Conditions (Carried Out on a BioRad iCycler®):
a. 94° C. for 120 sec
b. 94° C. for 20 sec c. 60° C. for 20 sec (this step provides more time for annealing)
d. 55° C. for 1 min (may decrease this temperature to improve primer annealing)
e. 72° C. for 20 sec
f. repeat steps b-e for 3 more cycles (total 4 cycles)
g. 4° C. for up to 20 minutes As quickly as possible once the reactions had reached 4° C., 1 μL of 300 mM EDTA was added (to make a final concentration of 10 mM) to terminate the activity of the polymerase. Each tube was agitated gently to ensure even mixing of the EDTA. Because the primer-extended molecules had sample-specific barcodes attached, the products of all reactions that were derived from different samples could be pooled together into a single tube.

Purification of Primer-Extended Products

The purification of primer-extended products was achieved via pull-down and elution steps using complementary biotinylated "capture" oligonucleotides and streptavidin-agarose beads (Thermo-Fisher). First, a mixture of complementary biotinylated oligonucleotides was added to the pooled primer-extension products. These oligonucleotides were designed to anneal to the specific sequences that should be produced if the primers were extended using the intended genomic DNA target region as their templates. A list of the 40 biotinylated oligos that were used in the present example is included in Table 8. By capturing with these biotinylated oligos, it was possible to ensure that only the specifically extended primers were isolated, and that any un-extended primers and any primers that were extended on non-specific DNA templates were not pulled down. For every 30 microliter reaction volume (plus 1 microliter of EDTA added), a final concentration of 200 nM of each biotinylated oligo was added (by addition of 3.5 μL of an 80 micromolar oligonucleotide mix for a final total concentration of 8 micromolar biotinylated oligos [all 40 oligos]). Annealing of the biotinlyated capture oligos with the primer-extended products was achieved by heating the mixture to 95° C. for 30 seconds, then to 70° C. for 20 seconds, then cooling by 2.5° C. every 20 seconds until the mixtures reached 25° C.

TABLE 8

List of biotinylated target-specific capture DNA oligonucleotides

| NAME | DNA OLIGO SEQUENCE | SEQ ID NO: |
|---|---|---|
| BNTP53-1 | 5'-BIO-CAAGATGTTTTGCCAACTGGCC | 133 |
| BNTP53-2 | 5'-BIO-CCTGTCGTCTCTCCAGCCCCAG | 134 |
| BNTP53-3 | 5'-BIO-GGCTGGTTGCCCAGGGTCCC | 135 |
| BNTP53-4 | 5'-BIO-GCCACTGACAACCACCCTTAACC | 136 |
| BNTP53-5 | 5'-BIO-CCTCATCTTGGGCCTGTGTTATCT | 137 |
| BNTP53-6 | 5'-BIO-GGGCAGCTCGTGGTGAGGC | 138 |
| BNPIK-1 | 5'-BIO-AAGAAACAGAGAATCTCCATTTTAGCAC | 139 |
| BNPIK-2 | 5'-BIO-TCAGTTCAATGCATGCTGTTTAATTGTG | 140 |
| BNBRAF | 5'-BIO-CTTACCATCCACAAAATGGATCCAGAC | 141 |

TABLE 8-continued

List of biotinylated target-specific capture DNA oligonucleotides

| NAME | DNA OLIGO SEQUENCE | SEQ ID NO: |
|---|---|---|
| BNFoxL2 | 5'-BIO-CGGAAGGGCCTCTTCATGCGGC | 142 |
| BNGNAS | 5'-BIO-GGCTTACTGGAAGTTGACTTTGTCCAC | 143 |
| BNCTNN | 5'-BIO-AGGACTTGGGAGGTATCCACATCC | 144 |
| BNPPP-1 | 5'-BIO-CTGCTGCCTCAGGATCCCCGTCC | 145 |
| BNPPP-2 | 5'-BIO-GTGGGACAATGTCAACGGTCGCT | 146 |
| BNPTEN-1 | 5'-BIO-CCCATAGAAATCTAGGGCCTCT | 147 |
| BNPTEN-2 | 5'-BIO-CTCTACTTTGATATCACCACACAGG | 148 |
| BNKIT-1 | 5'-BIO-CTTGGCAGCCAGAAATATCCTCCTTACTC | 149 |
| BNKIT-2 | 5'-BIO-CTCCCATTTGTGATCATAAGGAAGTTG | 150 |
| BNKIT-3 | 5'-BIO-ATACCAATCTATTGTGGGCTCTGG | 151 |
| BNEG-1 | 5'-BIO-CCCACACAGCAAAGCAGAAAC | 152 |
| BNEG-2 | 5'-BIO-AGCCACCTCCTTACTTTGCCTCC | 153 |
| BNEG-3 | 5'-BIO-GTCTTTGTGTTCCCGGACATAGTCC | 154 |
| BNAKT1 | 5'-BIO-TGAAGGTGCCATCATTCTTGAGGAG | 155 |
| BNATM | 5'-BIO-GAAGTGTCGAAGACAGCTGGTGAA | 156 |
| BNAPC | 5'-BIO-CAGCTTGCTTAGGTCCACTCTCTC | 157 |
| BNFGFR-1 | 5'-BIO-GGGCTTGTCCATGCGGTGGCC | 158 |
| BNFGFR-2 | 5'-BIO-CTCCACGTCGCTGCCCAGCACC | 159 |
| BNFGFR-3 | 5'-BIO-CAGCCGCCACCACCAGGATGAAC | 160 |
| BNMET-1 | 5'-BIO-CCTATTAAAGCAGTGCTCATGATTGG | 161 |
| BNMET-2 | 5'-BIO-CTTTCCAAAGCCATCCACTTCAC | 162 |
| BNSTK-1 | 5'-BIO-GAGTCCAGCACCTCCTTCACCTTG | 163 |
| BNSTK-2 | 5'-BIO-CGCCAGACTCACCGGGCACC | 164 |
| BNKRAS-1 | 5'-BIO-GTCACATTTTCATTATTTTTATTATAAGGCCTGC | 165 |
| BNKRAS-2 | 5'-BIO-GTATTATTTATGGCAAATACACAAAGAAAGC | 166 |
| BNNRAS-1 | 5'-BIO-GATGTGGCTCGCCAATTAACCCTGA | 167 |
| BNNRAS-2 | 5'-BIO-CTTGCTATTATTGATGGCAAATACACAG | 168 |
| BNHRAS-1 | 5'-BIO-GGGCAGGAGACCCTGTAGGAG | 169 |
| BNHRAS-2 | 5'-BIO-CAAAAGACTTGGTGTTGTTGATGGCA | 170 |
| BNK-Ctrl | 5'-BIO-AGAAAGGATTCTTTATGTTTCTCTTCAGG | 171 |
| BNB-Ctrl | 5'-BIO-GAGATTCCAATAACTGTTGTTCTCTTTGT | 172 |

5'-Bio = 5'-Biotin

Then, 7 μL of high capacity streptavidin-agarose bead slurry (Thermo-Fisher) was added (per 30 μL primer-extension reaction). Tubes were turned end-over-end constantly for at least 2 hours to promote binding of biotinylated oligos to the streptavidin beads. Beads were then centrifuged briefly, and any unbound supernatant was carefully removed, avoiding aspiration of any beads. The beads were then washed in about 200 μL of 10 mM Tris pH 7.6 and 50 mM NaCl (referred to hereafter as wash buffer). Beads were suspended in wash buffer by gentle agitation, then were briefly centrifuged, and the supernatant wash buffer was removed and discarded. A second wash was performed in the same way, except that once the beads were suspended, they were incubated at 45° C. for 30 minutes while the tube was turned end-over-end (this was to promote dissociation of any DNA molecules that may have annealed non-specifically to the biotinylated capture oligos). The beads were again centrifuged briefly, and the supernatant wash buffer was removed. The captured primer-extended products were eluted from the surface of the washed beads by heat-denaturation. Since the biotin-streptavidin interaction was not substantially disrupted by heating at 95° C., only the captured primer-extended products were eluted from the beads, whereas the biotinylated capture oligos remained bound to the beads. Elution was carried out directly into the pre-amplification PCR cocktail as described below.

Multiplexed Pre-Amplification PCR

The purified primer-extension products were eluted directly into a cocktail of buffer, nucleotides, and primers that was used to carry out the multiplexed pre-amplification reaction. The primer-extended DNA was eluted into the following cocktail:

| | |
|---|---|
| Molecular grade water | (enough to make 100 μL total reaction volume) |
| 10x Accuprime Taq PCR buffer #1 or pfx buffer (with dNTPs already added) | 10 μL |
| Forward primer mix for 40 amplicons (20 uM Fwd mix stock, 200 nM final each) | 40 μL |
| Universal reverse primer - ExtV2Rev (2 uM stock, 200 nM final) | 10 μL |
| Total | 100 μL |

The beads in the pre-amplification cocktail were heated at 95° C. for 30 seconds, were quickly and gently centrifuged, and the supernatant was transferred to a clean PCR tube. When the cocktail reached room temperature, 2 μL of Accuprime hotstart Taq polymerase (or 1 μL Accuprime Pfx) was added to the tube, and mixed by pipetting up and down. Then 30 μL of mineral oil was added to prevent evaporation during thermal cycling which was carried out as follows:
a. 94° C. for 2 minutes (95° C. if using Accuprime Pfx)
b. 94° C. for 20 seconds (95° C. if using Accuprime Pfx)
c. 63° C. for 30 seconds
d. 72° C. for 20 seconds
e. repeat (b) to (d) for a total of 15 cycles
f. 72° C. for 2 minutes Then, 11 μL of 100 mM EDTA was added (10 mM final concentration) to the completed reaction to chelate divalent cations and thus terminate polymerase activity.

The forward primers used in this pre-amplification reaction were designed to hybridize to regions on the target sequences that were nested relative to the binding sites of the biotinylated capture oligonucleotides that were used in the first primer extension reaction. This nested design provided an additional level of specificity so that the desired target DNAs would be preferentially amplified. The sequences of the universal pre-amplification reverse primer (ExtV2Rev), and the 40 different nested forward primers are listed in Table 9.

TABLE 9

List of 40 forward primers and the single universal reverse primer (ExtV2Rev) used for the pre-amplification reaction

| Name | DNA Sequence | SEQ ID NO: |
|---|---|---|
| ExtV2REV | CGAGACGGATCAAGCAGAAGACG | 173 |
| ExF-TP53-1 | GCCAACTGGCCAAGACCTGC | 174 |
| ExF-TP53-2 | CTCCAGCCCCAGCTGCTCAC | 175 |
| ExF-TP53-3 | GTCCCCAGGCCTCTGATTCCTC | 176 |
| ExF-TP53-4 | CCTCCCAGAGACCCCAGTTGC | 177 |
| ExF-TP53-5 | TGGGCCTGTGTTATCTCCTAGGTTG | 178 |
| ExF-TP53-6 | GCAGCTCGTGGTGAGGCTCC | 179 |
| ExF-PIK3CA-1 | AGAAACAGAGAATCTCCATTTTAGCACTTACC | 180 |
| ExF-PIK3CA-2 | TTCAATGCATGCTGTTTAATTGTGTGGAAG | 181 |
| ExF-BRAF | TCCACAAAATGGATCCAGACAACTGTTC | 182 |
| ExF-FoxL2 | GGCGCCGGTAGTTGCCCTTC | 183 |
| ExF-GNAS | GGAAGTTGACTTTGTCCACCTGGAAC | 184 |
| ExF-CTNNB1 | GGAGGTATCCACATCCTCTTCCTCAG | 185 |
| ExF-PPP2R1A-1 | CGACTCCCAGGTACTTCCGGAAC | 186 |
| ExF-PPP2R1A-2 | TGTCAACGGTCGCTCATCTACCTC | 187 |

TABLE 9-continued

List of 40 forward primers and the single universal reverse primer (ExtV2Rev) used for the pre-amplification reaction

| Name | DNA Sequence | SEQ ID NO: |
|---|---|---|
| ExF-PTEN-1 | CCATAGAAATCTAGGGCCTCTTGTGC | 188 |
| ExF-PTEN-2 | CACCACACACAGGTAACGGCTG | 189 |
| ExF-KIT-1 | GAAATATCCTCCTTACTCATGGTCGGATCA | 190 |
| ExF-KIT-2 | CCCATTTGTGATCATAAGGAAGTTGTGTTG | 191 |
| ExF-KIT-3 | GTGGGCTCTGGGAATCCTGCTG | 192 |
| ExF-EGFR-1 | CCACACAGCAAAGCAGAAACTCAC | 193 |
| ExF-EGFR-2 | ACCTCCTTACTTTGCCTCCTTCTGC | 194 |
| ExF-EGFR-3 | GTGTTCCCGGACATAGTCCAGGAG | 195 |
| ExF-AKT1 | GCCATCATTCTTGAGGAGGAAGTAGC | 196 |
| ExF-ATM | AGACAGCTGGTGAAAAATCCCTGAAC | 197 |
| ExF-APC | TGCTTAGGTCCACTCTCTCTTTTCAG | 198 |
| ExF-FGFR3-1 | GCGGTGGCCCTCCTTCAGCAG | 199 |
| ExF-FGFR3-2 | CCAGCACCGCCGTCTGGTTG | 200 |
| ExF-FGFR3-3 | CCACCAGGATGAACAGGAAGAAGC | 201 |
| ExF-MET-1 | CAGTGCTCATGATTGGGTCCGT | 202 |
| ExF-MET-2 | GCCATCCACTTCACTGGCAGC | 203 |
| ExF-STK11-1 | CTTCACCTTGCCGTAAGAGCCTTC | 204 |
| ExF-STK11-2 | CTCACCGGGCACCGTGAAGTC | 205 |
| ExF-KRAS-1 | CATTATTTTTATTATAAGGCCTGCTGAAAATGACTGA | 206 |
| ExF-KRAS-2 | TGGCAAATACACAAAGAAAGCCCTCC | 207 |
| ExF-NRAS-1 | CAATTAACCCTGATTACTGGTTTCCAACAG | 208 |
| ExF-NRAS-2 | GGCAAATACACAGAGGAAGCCTTCG | 209 |
| ExF-HRAS-1 | CAGGAGACCCTGTAGGAGGACC | 210 |
| ExF-HRAS-2 | TGATGGCAAACACACACAGGAAGC | 211 |
| ExF-KRAS-Cntrl | AGGATTCTTTATGTTTCTCTTCAGGCAACTG | 212 |
| ExF-BRAF-Cntrl | ACTGTTGTTCTCTTTGTTGGAGTGCATC | 213 |

Purification of the Products of the Pre-Amplification Reaction

The products of the pre-amplification reaction were purified using a QIAquick® PCR purification kit (Qiagen) according to the manufacturer's instructions. This removed the enzyme, dNTPs, and unincorporated primers from the double-stranded reaction products. Elution of the DNA from the column was carried out in 60 µL of EB buffer (composed of 10 mM Tris). This elution volume allowed 1 µL to be used in each of the 40 individual PCRs (see next section), with approximately 20 µL left over in case any failed reactions need to be repeated. The purified DNA can be stored at 4° C. for several days if necessary. Extra care was taken when handling any of the amplified products to avoid contamination of these products into the reagents used for reaction set-up (separate work-spaces were maintained for reagents and for amplification products).

Separate PCR Amplification of Individual Gene Targets (Mutation Hotspots)

After purification, products of the pre-amplification reaction were subjected to further amplification by PCR in separate tubes (one tube for each of the 40 target gene regions). These individual PCRs were performed in order to provide an additional layer of amplification specificity, since the multiplexed pre-amplification reaction was likely to have produced many spurious products in addition to the amplicons of interest. Using PCR primers that were nested relative to the primers used in the previous pre-amplification step allowed the desired target DNAs to be preferentially amplified. Also, by carrying out each individual PCR to saturation and using the same concentration of primers in each reaction, similar numbers of copies of each target region could be produced. Normalization of molecular counts in this way allowed a similar sequencing depth to be achieved for each target.

A different gene-specific forward primer was paired with a universal reverse primer in each of the 40 PCR tubes. Both primers were nested relative to the primers used in the pre-amplification reaction so that further amplification specificity could be achieved (a nested primer is designed so that its 3'-end hybridizes to a region within the desired target sequence that was flanked by the primers used in the earlier round of amplification). The forward primers contained extra sequences on their 5'-ends that were necessary for subsequent sequencing on an Illumina flow cell. The reverse primer was also designed to produce a product that was compatible with the Illumina sequencer without the need for attachment of additional adapter sequences. The sequences of the universal reverse PCR primer (called IntV2Rev) and the 40 different, target-specific forward PCR primers are listed in Table 10. A 4 nucleotide stretch of degenerate sequence was included in the forward primer to provide greater sequence diversity at the first few read positions, thereby improving cluster discrimination on the Illumina sequencer. Although these primers were designed to be compatible with the Illumina next-generation sequencing system, the method can relatively easily be adapted to other sequencing platforms. The PCR setup of each individual tube was as follows:

| | |
|---|---|
| Molecular grade water | 4.8 μL |
| 10x Accuprime Taq Buffer #1 | 1 μL |
| Forward gene-specific primer (1 uM stock, 200 nM final) | 2 μL |
| Universal reverse primer IntV2Rev (2 uM stock, 200 nM final) | 1 μL |
| Template DNA purified after pre-amplification reaction | 1 μL |
| Accuprime Taq DNA polymerase | 0.2 μL |
| Total | 10 μL |

TABLE 10

List of 40 nested forward primers and the single nested universal reverse primer (IntV2Rev)

| | | |
|---|---|---|
| IntV2 REV | CAAGCAGAAGACGGCATACGAGA | 217 |
| InF-TP53-1 | AATGATACGGCGACCACCGAGATCTACACTCTTTCCCTACACGACGCTCT TCCGATCTNNNNACTTGCAGCTGTGGGTTGATTCCAC | 218 |
| InF-TP53-2 | AATGATACGGCGACCACCGAGATCTACACTCTTTCCCTACACGACGCTCT TCCGATCTNNNNACTCCAGCTGCTCACCATCGCTATCT | 219 |
| InF-TP53-3 | AATGATACGGCGACCACCGAGATCTACACTCTTTCCCTACACGACGCTCT TCCGATCTNNNNACTTCCTCACTGATTGCTCTTAGGTCTGG | 220 |
| InF-TP53-4 | AATGATACGGCGACCACCGAGATCTACACTCTTTCCCTACACGACGCTCT TCCGATCTNNNNACTCAAACCAGACCTCAGGCGGCTC | 221 |
| InF-TP53-5 | AATGATACGGCGACCACCGAGATCTACACTCTTTCCCTACACGACGCTCT TCCGATCTNNNNACTGCTCTGACTGTACCACCATCCAC | 222 |
| InF-TP53-6 | AATGATACGGCGACCACCGAGATCTACACTCTTTCCCTACACGACGCTCT TCCGATCTNNNNACTTCCCCTTTCTTGCGGAGATTCTCT | 223 |
| InF-PIK3CA-1 | AATGATACGGCGACCACCGAGATCTACACTCTTTCCCTACACGACGCTCT TCCGATCTNNNNACTCACTTACCTGTGACTCCATAGAAAATCTTTC | 224 |
| InF-PIK3CA-2 | AATGATACGGCGACCACCGAGATCTACACTCTTTCCCTACACGACGCTCT TCCGATCTNNNNACTGAAGATCCAATCCATTTTTGTTGTCCAGC | 225 |
| InF-BRAF | AATGATACGGCGACCACCGAGATCTACACTCTTTCCCTACACGACGCTCT TCCGATCTNNNNACTCAAACTGATGGGACCCACTCCATC | 226 |
| InF-FoxL2 | AATGATACGGCGACCACCGAGATCTACACTCTTTCCCTACACGACGCTCT TCCGATCTNNNNACTCGGTAGTTGCCCTTCTCGAACATG | 227 |
| InF-GNAS | AATGATACGGCGACCACCGAGATCTACACTCTTTCCCTACACGACGCTCT TCCGATCTNNNNACTACTTGGTCTCAAAGATTCCAGAAGTCAG | 228 |
| InF-CTNNB1 | AATGATACGGCGACCACCGAGATCTACACTCTTTCCCTACACGACGCTCT TCCGATCTNNNNACTCCTCAGGATTGCCTTTACCACTCAG | 229 |
| InF-PPP2R1A-1 | AATGATACGGCGACCACCGAGATCTACACTCTTTCCCTACACGACGCTCT TCCGATCTNNNNACTCCGGAACCTGTGCTCAGATGACAC | 230 |
| InF-PPP2R1A-2 | AATGATACGGCGACCACCGAGATCTACACTCTTTCCCTACACGACGCTCT TCCGATCTNNNNACTCTGTGAACTTGTCAGCCACCATGTAG | 231 |
| InF-PTEN-1 | AATGATACGGCGACCACCGAGATCTACACTCTTTCCCTACACGACGCTCT TCCGATCTNNNNACTCCTTTAAAAATTTGCCCCGATGTAATAAATATGC | 232 |
| InF-PTEN-2 | AATGATACGGCGACCACCGAGATCTACACTCTTTCCCTACACGACGCTCT TCCGATCTNNNNACTGGCTGAGGGAACTCAAAGTACATGAAC | 233 |

TABLE 10-continued

List of 40 nested forward primers and the single nested
universal reverse primer (IntV2Rev)

| Name | Sequence | SEQ ID NO |
|---|---|---|
| InF-KIT-1 | AATGATACGGCGACCACCGAGATCTACACTCTTTCCCTACACGACGCTCT TCCGATCTNNNNACTGGATCACAAAGATTTGTGATTTTGGTCTAGC | 234 |
| InF-KIT-2 | AATGATACGGCGACCACCGAGATCTACACTCTTTCCCTACACGACGCTCT TCCGATCTNNNNACTGGTCTATGTAAACATAATTGTTTCCATTTATCT | 235 |
| InF-KIT-3 | AATGATACGGCGACCACCGAGATCTACACTCTTTCCCTACACGACGCTCT TCCGATCTNNNNACTGCCACACATTGGAGCATGCCA | 236 |
| InF-EGFR-1 | AATGATACGGCGACCACCGAGATCTACACTCTTTCCCTACACGACGCTCT TCCGATCTNNNNACTGAAACTCACATCGAGGATTTCCTTGTTG | 237 |
| InF-EGFR-2 | AATGATACGGCGACCACCGAGATCTACACTCTTTCCCTACACGACGCTCT TCCGATCTNNNNACTTGCATGGTATTCTTTCTCTTCCGCAC | 238 |
| InF-EGFR-3 | AATGATACGGCGACCACCGAGATCTACACTCTTTCCCTACACGACGCTCT TCCGATCTNNNNACTGAGGCAGCCGAAGGGCATGAG | 238 |
| InF-AKT1 | AATGATACGGCGACCACCGAGATCTACACTCTTTCCCTACACGACGCTCT TCCGATCTNNNNACTGTGGCCGCCAGGTCTTGATG | 240 |
| InF-ATM | AATGATACGGCGACCACCGAGATCTACACTCTTTCCCTACACGACGCTCT TCCGATCTNNNNACTCATGTGTAGAAAGCAGATTTCTCCATGATTC | 241 |
| InF-APC | AATGATACGGCGACCACCGAGATCTACACTCTTTCCCTACACGACGCTCT TCCGATCTNNNNACTTTCAGCAGTAGGTGCTTTATTTTTAGGTAC | 242 |
| InF-FGFR3-1 | AATGATACGGCGACCACCGAGATCTACACTCTTTCCCTACACGACGCTCT TCCGATCTNNNNACTCAGCTTGAAGAGCTCCTCCACAG | 243 |
| InF-FGFR3-2 | AATGATACGGCGACCACCGAGATCTACACTCTTTCCCTACACGACGCTCT TCCGATCTNNNNACTCCTGCAGGATGGGCCGGTG | 244 |
| InF-FGFR3-3 | AATGATACGGCGACCACCGAGATCTACACTCTTTCCCTACACGACGCTCT TCCGATCTNNNNACTCCACCCCGTAGCTGAGGATGC | 245 |
| InF-MET-1 | AATGATACGGCGACCACCGAGATCTACACTCTTTCCCTACACGACGCTCT TCCGATCTNNNNACTGCTGGAGACATCTCACATTGTTTTGTTG | 246 |
| InF-MET-2 | AATGATACGGCGACCACCGAGATCTACACTCTTTCCCTACACGACGCTCT TCCGATCTNNNNACTGCTTTGCACCTGTTTTGTTGTGTACAC | 247 |
| InF-STK11-1 | AATGATACGGCGACCACCGAGATCTACACTCTTTCCCTACACGACGCTCT TCCGATCTNNNNACTCCCATCAGGTACTTGCCGATGAG | 248 |
| InF-STK11-2 | AATGATACGGCGACCACCGAGATCTACACTCTTTCCCTACACGACGCTCT TCCGATCTNNNNACTCTGAGTGTAGATGATGTCATCCTCGATG | 249 |
| InF-KRAS-1 | AATGATACGGCGACCACCGAGATCTACACTCTTTCCCTACACGACGCTCT TCCGATCTNNNNACTGCTGAAAATGACTGAATATAAACTTGTGGTA | 250 |
| InF-KRAS-2 | AATGATACGGCGACCACCGAGATCTACACTCTTTCCCTACACGACGCTCT TCCGATCTNNNNACTCAGTCCTCATGTACTGGTCCCTCATT | 251 |
| InF-NRAS-1 | AATGATACGGCGACCACCGAGATCTACACTCTTTCCCTACACGACGCTCT TCCGATCTNNNNACTTCTTGCTGGTGTGAAATGACTGAGTAC | 252 |
| InF-NRAS-2 | AATGATACGGCGACCACCGAGATCTACACTCTTTCCCTACACGACGCTCT TCCGATCTNNNNACTTCGCCTGTCCTCATGTATTGGTCT | 253 |
| InF-HRAS-1 | AATGATACGGCGACCACCGAGATCTACACTCTTTCCCTACACGACGCTCT TCCGATCTNNNNACTCCTGAGGAGCGATGACGGAATATAAG | 254 |
| InF-HRAS-2 | AATGATACGGCGACCACCGAGATCTACACTCTTTCCCTACACGACGCTCT TCCGATCTNNNNACTATGTACTGGTCCCGCATGGCG | 255 |
| InF-KRAS-Cntrl | AATGATACGGCGACCACCGAGATCTACACTCTTTCCCTACACGACGCTCT TCCGATCTNNNNACTAGGACTTTTAGAATTCTTAAATGTCATCCGC | 256 |
| InF-BRAF-Cntrl | AATGATACGGCGACCACCGAGATCTACACTCTTTCCCTACACGACGCTCT TCCGATCTNNNNACTTCTAGCTTGCTGGTGTATTCTTCATAGG | 257 |

Mineral oil (20 µL) was added to each tube to prevent evaporation during PCR. Again, both Accuprime Taq polymerase as well as Accuprime Pfx were tested for PCR amplification, and both worked. The temperature cycling conditions used for PCR were as follows:
 a. 94° C. for 2 minutes (95° C. if using Accuprime Pfx)
 b. 94° C. for 20 seconds (95° C. if using Accuprime Pfx)
 c. 64° C. for 30 seconds
 d. 72° C. for 20 seconds
 e. repeat b to d for a total of 36 to 45 cycles (36 cycles for Taq and 45 cycles for Pfx).
 f. 72° C. for 2 minutes
 g. 4° C. until removed from thermal cycler While the PCR tubes were still at 4° C., 5 µL of 30 mM EDTA was added to inactivate the polymerase (10 mM EDTA final). This was added under the mineral oil layer, and was pipetted up and down to mix. Products from all 40 reactions were pooled into a single tube (equal volumes from each of the 40 reactions were added to the final mix).

Preparation of DNA for Next-Generation Sequencing

The pooled PCR reaction products were purified on a 2% agarose gel with ethidium bromide and 1×TBE buffer. Since all PCR products were of a similar final length, the pooled products appeared on the gel as a somewhat diffuse band. This diffuse band was excised from the gel using a fresh scalpel blade, ensuring that the gel was cut a few millimeters above and below the visible band to include any low-intensity bands that may have run faster or slower and were not well-visualized. Using a QIAquick® Gel Extraction kit (Qiagen) according to the manufacturer's instructions, the DNA was isolated from the gel slice. The DNA was eluted into 50 µL of elution buffer, EB.

Next-Generation Sequencing

To prepare the sample for loading onto an Illumina HiSeq flow cell, the concentration of the DNA was measured using an Agilent Bioanalyzer®, and the DNA was diluted to the concentration recommended by Illumina. In order to increase sequence diversity on the flow cell, Phi-X control DNA (Illumina) was added so that the total molar amount of Phi-X DNA was approximately 30% of the final sample that was loaded onto the flow cell.

Cluster formation was carried out on the flow cell according to Illumina's protocol. The sample was loaded onto a single lane of a flow cell. The sequencing was performed on a HiSeq® 2000 instrument in multiplexed paired-end mode, with a read length of 75 base pairs in each direction. An index read was also performed, and the length of the index read was increased from the standard 7 cycles up to 13 cycles so that our longer custom barcodes and MLT sequences could be appropriately read. A control lane was designated that contained either phi-X DNA or genomic DNA so that matrix generation for phasing/prephasing would be based on a sample having greater sequence diversity than was present in our sample. Demultiplexing of the sequences was performed using custom computer code.

Outline of Algorithm for Sequence Analysis

The sequences that survived the filtering process were comprised of the PCR amplicons of interest as well as sequences derived from control Phi-X DNA. Our algorithm effectively ignored Phi-X sequences because those sequences did not conform to the filtering requirements described below.

A computer algorithm was designed to sort, align, and count the millions of sequences that were generated by the high-throughput sequencer. The sequence elements used in the algorithm are identified in FIG. 14. The following steps provide an outline of the process and rationale used to analyze the sequence data:

1. Only clonal sequences that had passed Illumina's chastity filter were included in the analysis. Any sequences that had a "." at any position were eliminated (these were counted as dot rejects). If an unusually large number of dots were found at a particular sequence position (indicating sequencer failure at that cycle), the filter was modified in order to avoid filtering out an unreasonably large fraction of sequences.

2. The 8 nucleotide barcode from the index read (read #2) was used to assign each filtered clonal sequence to a sample-specific bin. The sequence in the region of the barcode was expected to be in the format, BBBBBBBBNNAT, where "B" was a barcode nucleotide and "N" was a nucleotide belonging to the molecular lineage tag (a position designated as N had an approximately equal probability of being A, C, G, or T in any given molecule. In order for the clonal sequence to be assigned to a sample-specific bin, the following conditions had to be satisfied:
 a. the sequence BBBBBBBB at positions 1-8 had to exactly match the reverse complement of one of the 96 barcodes listed in Table 6;
 And
 b. the nucleotides at position 11 and 12 of the index read had to be AT. If a clonal sequence failed to satisfy both above conditions, it was classified as a barcode reject. In case the lack of sequence diversity at these positions 11 and 12 caused the read quality to be greatly diminished, leading to a high rate of miscalls or "." calls, requirement (b) was optionally modified or eliminated.

3. Each clonal sequence that was assigned to a sample-specific bin was further sub-classified according to the targeted gene segment from which it arose. The primer sequences from both the forward and reverse reads were used to assign each clone to a particular gene segment. In the present example, 40 distinct gene segments were analyzed. In order to assign a clonal sequence to a gene target bin, the conditions (a), (b), and (c) had to be satisfied.
 a. In the forward read, the first 8 nucleotides of the primer sequence (designated by a "F" in FIG. 14) had to exactly match the first 8 nucleotides of one of the 40 forward gene-specific primer sequences.
 b. In the reverse read, the first 8 nucleotides of the primer sequence (designated by a "R" in FIG. 14) had to exactly match the first 8 nucleotides of one of the 40 reverse gene-specific primer sequences.
 c. The forward primer and reverse primer reads had to lead to assignment of each clone to the same gene segment. Assignment of a single clonal sequence to more than one gene segment bin was not permissible.
If a clonal sequence failed to satisfy these conditions, it was classified as a gene segment reject.

4. Each clonal sequence that was successfully assigned to a sample-specific barcode bin and to a gene segment bin then had its forward and reverse reads aligned to each other using a Smith-Waterman algorithm, as described in Example 1 (the reverse-complement of read #3 was derived to facilitate alignment). This enabled identification of the region of overlap between the forward and reverse reads. Different lengths of overlap were expected for different gene segments since the forward and reverse read-lengths were constant but the PCR amplicon length differed for different gene segments. The length of overlap could also vary because of the presence of insertion or deletion mutations. The forward and reverse reads were also aligned to the wild-type reference sequence for its assigned gene segment (the full-length wild-type reference sequences are listed in Table 11).

TABLE 11

List of wild-type reference sequences for all 40 targeted gene segments

| Gene Segment | Reference Sequence (FFFF....FFFF[xxxx......xxxx]RRRR.....RRRR) | |
|---|---|---|
| TP53-1 | TGCAGCTGTGGGTTGATTCCAC[accccccgcccggcacccgcgtccgcgccatggcca tcta]CAAGCAGTCACAGCACAG | 258 |
| TP53-2 | CCAGCTGCTCACCATCGCTATCT[gagcagcgctcatggtgggggcagcgcctcac] AACCTCCGTCATGTGCTA | 259 |
| TP53-3 | TCCTCACTGATTGCTCTTAGGTCTGG[cccctcctcagcatcttatccgagtggaagg a]AATTTGCGTGTGGAGTATTTGT | 260 |
| TP53-4 | CAAACCAGACCTCAGGCGGCTC[atagggcaccaccacactatgtcgaa]AAGTG TTTCTGTCATCCAAATAT | 261 |
| TP53-5 | GCTCTGACTGTACCACCATCCAC[tacaactacatgtgtaacagttcctgcatgggcggc atgaaccggaggc]CCATCCTCACCATCATCACAG | 262 |
| TP53-6 | TCCCCTTTCTTGCGGAGATTCTCT[tcctctgtgcgccggtctctcccaggacaggcac aaacacgcac]CTCAAAGCTGTTCCGTCCCAG | 263 |
| PIK3CA-1 | CACTTACCTGTGACTCCATAGAAAATCTTTC[tcctgctcagtgatttcagag]A GAGGATCTCGTGTAGAAATTGCA | 264 |
| PIK3CA-2 | GAAGATCCAATCCATTTTTGTTGTCCAGC[caccatgatgtgcatcat]TCATT TGTTTCATGAAATACTCCAAAGA | 265 |
| BRAF | CAAACTGATGGGACCCACTCCATC[gagatttcactgtagc]TAGACCAAAA TCACCTATTTTTACTGTT | 266 |
| FoxL2 | CGGTAGTTGCCCTTCTCGAACATG[tcttcgcaggccgg]GTCCAGCGTCC AGTAGTTGCA | 267 |
| GNAS | ACTTGGTCTCAAAGATTCCAGAAGTCAG[gacacggcagcga]AGCAGGT CCTGAAACAAAATTGAG | 268 |
| CTNNB1 | CCTCAGGATTGCCTTTACCACTCAG[agaaggagctgtggtagtggcaccagaatgg attccagagtcc]AGGTAAGACTGTTGCTGCCAG | 269 |
| PPP2R1A-1 | CCGGAACCTGTGCTCAGATGACAC[ccccatggtgcggcgggcc]GCAGCCT CCAAGCTGGGT | 270 |
| PPP2R1A-2 | CTGTGAACTTGTCAGCCACCATGTAG[cggacgcgccaggact]TGTCTTCA GCGGCCTGGCT | 271 |
| PTEN-1 | CCTTTAAAAATTTGCCCCGATGTAATAAATATGC[acatatcattacaccagtt cgtcc]CTTTCCAGCTTTACAGTGAATTGCC | 272 |
| PTEN-2 | GGCTGAGGGAACTCAAAGTACATGAAC[ttgtcttcccgtcgtgtgg]GTCCTG AATTGGAGGAATATATCTTCAT | 273 |
| KIT-1 | GGATCACAAAGATTTGTGATTTTGGTCTAGC[cagagacatcaagaat]GAT TCTAATTATGTGGTTAAAGGAAACGC | 274 |
| KIT-2 | GGTCTATGTAAACATAATTGTTTCCATTTATCT[cctcaacaaccttccactgta cttcatacatgggttt]CTGTGGGGAGAAAGGGAAAAC | 275 |
| KIT-3 | GCCACACATTGGAGCATGCCA[ttcacgagcctgtcgtaagtcag]GATTTCTGG TTTTGCTACAGGAAC | 276 |
| EGFR-1 | GAAACTCACATCGAGGATTTCCTTGTTG[gctttcggagatgttgcttctcttaattcc ttgatagc]GACGGGAATTTTAACTTTCTCACCG | 277 |
| EGFR-2 | TGCATGGTATTCTTTCTCTTCCGCAC[ccagcagtttggccagcc]CAAAATC TGTGATCTTGACATGCTT | 278 |
| EGFR-3 | GAGGCAGCCGAAGGGCATGAG[ctgcgtgatg]AGCTGCACGGTGGAGG TGAG | 279 |
| AKT1 | GTGGCCGCCAGGTCTTGATG[tactcccct]ACAGACGTGCGGGTGGTC | 280 |
| ATM | CATGTGTAGAAAAGCAGATTTCTCCATGATTC[atttgtatcttgg]AGTAAA ATATCATGAATCAAGTATGGAAGA | 281 |
| APC | TTCAGCAGTAGGTGCTTTATTTTTAGGTAC[ttctcgcttg]GTTTGAGCT GTTTGAGGAGGTC | 282 |

TABLE 11-continued

List of wild-type reference sequences for all 40 targeted gene segments

| Gene Segment | Reference Sequence (FFFF....FFFF[xxxx......xxxx]RRRR.....RRRR) | |
|---|---|---|
| FGFR3-1 | CAGCTTGAAGAGCTCCTCCACAG[ggatgccggggtacggggagcccc]CCAGCGTGAAGATCTCCCAT | 283 |
| FGFR3-2 | CCTGCAGGATGGGCCGGTG[cggggagcgctctgtggg]GGCAGATGACGCTCAGGGA | 284 |
| FGFR3-3 | CCACCCCGTAGCTGAGGATGC[ctgcatacacactgcccgcc]TCGTCAGCCTCCACCAGCG | 285 |
| MET-1 | GCTGGAGACATCTCACATTGTTTTGTTG[acgatcttgttgaaga]AGTCGTTGACATATTTGATAGGGAAC | 286 |
| MET-2 | GCTTTGCACCTGTTTTGTTGTGTACAC[tatagtattctttatcataca]TGTCTCTGGCAAGACCAAAATT | 287 |
| STK11-1 | CCCATCAGGTACTTGCCGATGAG[cttggcccgcttgcggcgcggctggtaga]TGACCTCGGTGGAGTCGATA | 288 |
| STK11-2 | CTGAGTGTAGATGATGTCATCCTCGATG[tcgaagaggtcctcgtcctcgtccgcgc]CGTGCAGGTCCTCCAAGTAT | 289 |
| KRAS-1 | GCTGAAAATGACTGAATATAAACTTGTGGTA[gttggagctggtggcgt]AGGCAAGAGTGCCTTGACGAC | 290 |
| KRAS-2 | CAGTCCTCATGTACTGGTCCCTCATT[gcactgtactcctcttg]ACCTGCTGTGTCGAGAATATCG | 291 |
| NRAS-1 | TCTTGCTGGTGTGAAATGACTGAGTAC[aaactggtggtggttggagcaggtggtgt]TGGGAAAAGCGCACTGAT | 292 |
| NRAS-2 | TCGCCTGTCCTCATGTATTGGTCT[ctcatggcactgtactcttcttg]TCCAGCTGTATCCAGTATGTCA | 293 |
| HRAS-1 | CCTGAGGAGCGATGACGGAATATAAG[ctggtggtggtgggcgccggcggtgt]GGGCAAGAGTGCGCTGACCAC | 294 |
| HRAS-2 | ATGTACTGGTCCCGCATGGCG[ctgtactcctcctg]GCCGGCGGTATCCAGGATGA | 295 |
| KRAS-Cntrl | AGGACTTTTAGAATTCTTAAATGTCATCCGC[at]AGGTGTTTTGTCAATATTATAAACAGGAT | 296 |
| BRAF-Cntrl | TCTAGCTTGCTGGTGTATTCTTCATAGG[cctataaaataaagcagacttatat]TCAATCCGGACTTTGTCCTGAT | 297 |

Note:
Forward and reverse primer sequences are in capital letters, to the left and right of the square brackets, respectively. The actual reverse primer sequence would be the reverse-complement of that shown above. The genomic wild-type amplicon target sequence is in lower case letters within the square brackets.

5. Next, any variants or mutations that existed within the amplicon target region for each gene segment were identified and quantified (nucleotides in this region were designated by a "X" in FIG. 14). Wild-type sequences of the amplicon target regions (region between flanking primers) for all 40 gene segments are listed in lower case letters within square brackets in Table 11. All clones belonging to a particular sample-specific bin and a particular gene segment bin were compared to the wild-type sequence in the amplicon target region. If a clonal sequence had perfect agreement between its two overlapping reads in the amplicon target region, but deviated from the wild-type sequence, then that clone was identified and counted as a "consistent variant". If a clonal sequence had perfect agreement between its two overlapping reads in the amplicon target region, and was perfectly consistent with the wild-type sequence, then it was identified and counted as an "exact match to wild type". If a clonal sequence had deviations from the amplicon target reference sequence seen in either or both of the forward and reverse reads, but the two reads were not perfectly consistent with each other, then that clone was identified and counted as an "inconsistent variant". Any mismatches, insertions, or deletions relative to the reference sequence (whether found in both reads or in a single read) were counted and tabulated for each position within the amplicon target region for all sequences in a given bin (For purposes of illustration, results of a hypothetical experiment are shown in FIG. 15).

6. In order to distinguish mutant sequences that were present in the original template DNA molecules from those arising due to sequencing errors or errors introduced during PCR amplification or sample processing, sequences called "molecular lineage tags" (MLTs) were used. As shown in FIG. 14, the sequence for MLT-1 was comprised of a total of 8 degenerate nucleotide positions (derived by concatenating 6 positions of MLT-1a and 2 positions of MLT-1b). Each of the eight N positions had an approximately equal likelihood of having an A, C, G, or T nucleotide, so that 4^8=65,536 possible MLT sequences could be generated. Thus, a particular primer molecule would be expected to have any one of the 65,536 possible MLT sequences. Prior to amplification by PCR, the DNA template molecules were copied by primer-extension, and a MLT-1 sequence became attached to each primer-extended copy. Thus, each template copy was tagged with one of 65,536 possible MLT-1 sequences.

To identify variants arising from mutant template DNA molecules, first a list of all "consistent variants" was generated. If a "consistent variant" sequence was seen in more than one clone within a bin of sequences, then the number of copies of such variants was counted. These variants were listed along with the number of clonal copies (in descending order of frequency) as shown in FIG. 15. Then, for all clones belonging to a particular "consistent variant" sequence, a list of MLT-1 sequences associated with the clones was generated (the actual list of MLT-1 sequences was not displayed). Within each list, any MLT sequence that was found to be associated with more than one clone was classified as a "multiply occurring MLT". A histogram of such multiply occurring MLTs was generated for each variant (as shown in FIG. 15). The count of different MLT-1 sequences occurring "N" times for a given variant was listed in a numerical table (where N was the number of copies of the same MLT). An alternate way to present the MLT-1 counts was to list the "N" value and the number of different MLTs having that number of copies (e.g. N×Z, where Z is the number of different MLT sequences having N copies). For variant sequences arising from one or more mutant DNA template molecules, there was a high probability of finding multiply occurring MLTs with a high "N" value (because the number of clonal sequences sampled post-amplification was several-fold greater than the number of template DNA molecules that were copied and tagged in the primer-extension reaction). In contrast, for variant sequences arising from errors introduced during amplification of wild-type template molecules, it was unlikely to find MLT-1 sequences with "N" values as high as those associated with true mutant templates. Since known mutant template oligonucleotides had been spiked into each sample prior to amplification, these internal standards were used to determine the range of "N" values that should be expected for variant sequences derived from unknown mutant templates. Values falling below that range were presumed to be associated with variants arising from errors of amplification or sequencing.

7. A "mutation authenticity score" (MAS) can be used to facilitate the identification of variant sequences arising from mutant template DNA molecules. The MLT copy numbers, "N", that are associated with the spiked-in mutant internal control oligos (having mutations at two distinct positions) can be evaluated (Table 7). The variant sequences that arise from these authentic mutant templates are associated with MLT-1 sequences having relatively high "N" values. The value "$N_{auth}$" is in one embodiment the mean "N" value for these known authentic mutant templates. The "$N_{auth}$" value can be weighted or unweighted. If a mutation were introduced during the first cycle of PCR, the "N" value of such a variant sequence would be approximately $(1/1.7) \times N_{auth}$ (if each cycle of PCR yields approximately 1.7-fold amplification). Similarly, a variant sequence would have "N" values of approximately $(1/1.7^y) \times N_{auth}$ (if a mutation were introduced during the $y^{th}$ cycle of PCR). Thus, a mutation authenticity score is calculated for each "consistent variant" sequence based on how close the "N" values of its MLTs are to the "$N_{auth}$" values of the authentic mutants that are spiked into the reaction. A variant would be likely to be authentic if its "N" values were distributed within a defined range of the $N_{auth}$ values.

Results

A set of control plasma-derived DNA samples was tested. These samples contained various ratios of normal plasma DNA spiked with known amounts of mutant oligonucleotides (listed in Table 7). It was consistently observed that the PCR products were formed in a highly specific manner for all 40 gene segments included in the panel. The methods were extensively tested using a real-time quantitative thermal cycler, and comparisons to negative controls having no plasma DNA or having mouse DNA confirmed that the intended targets were being amplified. The products of all 40 PCRs were run on an agarose gel, and the production of appropriate-sized amplicons was confirmed.

Sequencing of the 40 pooled amplicons from multiple barcoded samples on the Illumina HiSeq® 2000 platform further confirmed that all intended gene segments were amplified. The total number of raw clonal sequences yielded was 282,965,036. After filtering, the rejected sequences were as follows:

| | |
|---|---|
| Failed Illumina's chastity filter: | 79,320,290 |
| Positions 5-7 in forward read were not "ACT": | 23,751,168 |
| Rejected because of the presence of an N in position 8 or beyond: | 27,477,576 |
| Failed to recognize forward primer: | 6,304,833 |
| Barcode did not exactly match one in our set of 96: | 15,921,744 |
| Positions 11-12 of index read were not "AT": | 2,903,342 |
| Failed to recognize reverse primer: | 17,064,651 |
| Remaining filtered reads: | 110,221,432 |

The total number of filtered counts assigned to each of the 40 gene segments is listed in Table 12. These data revealed a relatively even distribution of counts across the various amplicons.

TABLE 12

Number of filtered sequence counts associated with each targeted gene segment.

| | |
|---|---|
| AKT1 | 1927236 |
| APC | 3263261 |
| ATM | 2988621 |
| BRAF | 2644671 |
| BRAF-Cntrl | 2827920 |
| CTNNB1 | 3387874 |
| EGFR-1 | 2582553 |
| EGFR-2 | 2670482 |
| EGFR-3 | 1908549 |
| FGFR3-1 | 2441848 |
| FGFR3-2 | 1907661 |
| FGFR3-3 | 2154173 |
| FoxL2 | 2782971 |
| GNAS | 2481154 |
| HRAS-1 | 2173717 |
| HRAS-2 | 2456244 |
| KIT-1 | 1960170 |
| KIT-2 | 4202032 |
| KIT-3 | 2739896 |
| KRAS-1 | 5647782 |
| KRAS-2 | 3421539 |
| KRAS-Cntrl | 3076757 |
| MET-1 | 2923088 |
| MET-2 | 2956664 |
| NRAS-1 | 4037334 |
| NRAS-2 | 2462906 |

TABLE 12-continued

Number of filtered sequence counts associated with each targeted gene segment.

| | |
|---|---|
| PIK3CA-1 | 2124016 |
| PIK3CA-2 | 2807504 |
| PPP2R1A-1 | 2087213 |
| PPP2R1A-2 | 1966662 |
| PTEN-1 | 3125952 |
| PTEN-2 | 2562118 |
| STK11-1 | 2969119 |
| STK11-2 | 2613351 |
| TP53-1 | 2494793 |
| TP53-2 | 2248788 |
| TP53-3 | 3074251 |
| TP53-4 | 2964973 |
| TP53-5 | 2632869 |
| TP53-6 | 2522720 |
| Total | 110221432 |

Figure 16:
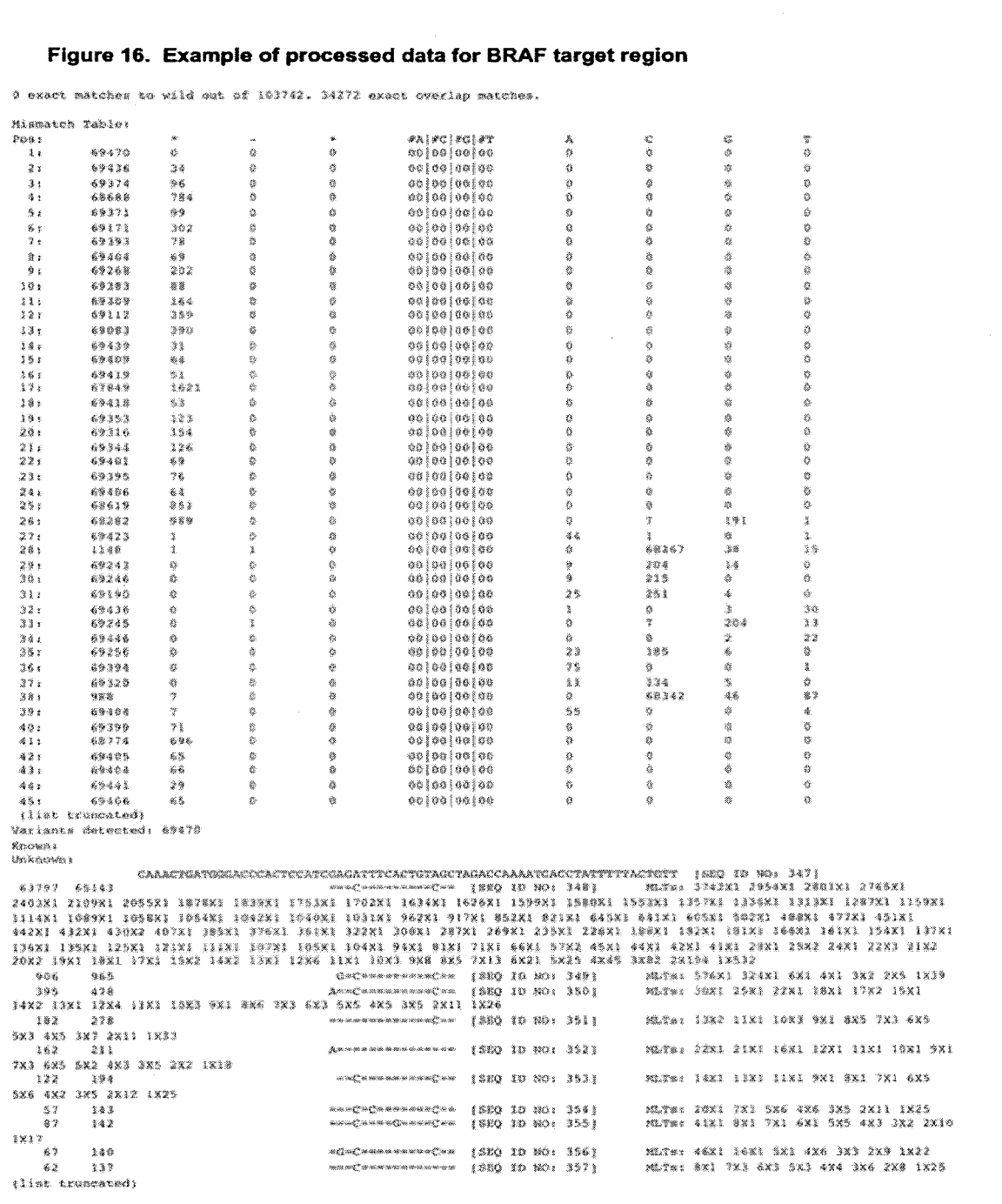

The sequence data were processed using a modified version of the computer code that was used in Example 1. The results demonstrated that control double-mutant oligonucleotides that were spiked into plasma DNA could be reliably detected and quantified. Requiring consistency of overlapping paired-end reads appeared to eliminate the vast majority sequencer errors. Also, analysis of the MLT sequences associated with "consistent variants" made it possible to distinguish sequences arising from authentic mutant templates from those introduced during amplification or sequencing. An example of processed data for the BRAF gene target region for a sample in which approximately equal numbers of copies of normal plasma DNA and double-mutant control oligos were mixed is shown in FIG. 16. This output represented the analysis of data from a single bin (single gene segment, single barcode). In this example, a total count of 103,742 clonal sequences were assigned to the bin, and 65,143 of these counts arose from amplification of the double-mutant oligonucleotide that was spiked in. The double-mutant sequences comprised approximately half of the total sequences in this bin. The MLT counts associated with each consistent variant were listed in the format N×y where y was the number of unique MLT sequences that had N copies associated with that particular consistent variant. It was observed that the variant sequence arising from spiked-in control mutant templates was associated with several MLT-1 sequences having high copy numbers (N). The highest value of N for this variant was 3742, and there were many distinct MLTs that had copy numbers in the thousands. In contrast, the next most abundant variant had only 965 total counts and was associated with only a few distinct MLTs. The highest value of N for this variant was 576, and only one other MLT had a count in the hundreds range. All other consistent variants in the list were associated with very low MLT copy numbers. Based on these observations, it could be confirmed that only the spiked-in control oligonucleotides produced variant sequences that had high MLT counts. MLT counts associated with variant sequences that likely arose from errors of PCR or sequencing were much lower, as predicted.

Example 3

This example demonstrates the application of methods that incorporated methods of Example 2, and included modifications thereof. A modification included elimination of separate PCRs for each target DNA in the final step. Instead, the final amplification was performed in a single tube using universal PCR primers. This also eliminated the requirement for a pre-amplification step. Pooled amplification was made possible by copying, tagging, and purifying the targeted DNA regions in a highly selective manner; spurious templates that could be amplified by universal primers in the final PCR would be minimized (FIG. 1). In this example, the same 40 genomic target regions were analyzed as in Example 2.

Methods

Preparation of Mixtures of Primers Having Combinations of Modular Oligonucleotide Segments Mixtures of primers having combinations of modular barcode segments and gene-specific segments were prepared as described in Example 2. The preferred approach, called "modular automated synthesis and purification", is schematized in FIG. 3, and is described in detail in Example 2.

Collection and Processing of Patient Plasma Samples

Blood was collected and processed as described in Example 2.

Extraction and Purification of DNA from Plasma

DNA was extracted from plasma as described in Example 2.

Round 1 PCR

In order to make a limited number of tagged copies (fewer than 20) of the plasma-derived template DNA molecules, a few cycles of PCR were performed (in contrast to primer extension that was performed in Example 2). The reverse primers used in the first round of PCR were the modular barcoded mixtures of gene-specific primers as described above (same as the primers used in the primer extension reaction in Example 2). For forward primers, the same oligonucleotides were used as the biotinylated capture oligonucleotides that had been used in Example 2 to purify the primer-extension products. The sequences of the forward primers are listed in Table 8.

Forty different gene regions were targeted, and therefore a combination of 40 different biotinylated forward primers and 40 different modular barcoded gene-specific reverse primers were used in the Round 1 PCR for each sample. For a given sample, the mixture of gene-specific reverse primers all had the same, sample-specific barcode in the 5' segment. The primer mixes were produced so that an approximately equimolar concentration of 40 different forward and 40 different reverse primers would be present in the reaction (final concentration of approximately 100 nM each primer). In addition to sample-specific barcodes, the reverse primers also contained degenerate sequence regions known as molecular lineage tags (MLTs) as well as common sequences at the 5'-end that allowed for hybridization of "universal" PCR primers in subsequent steps. The MLT assigned to each copy in Round 1 PCR was referred to as MLT-1.

Control DNA molecules containing known mutations were spiked into each Round 1 PCR to serve as internal quantitative standards. As described in Example 2, these DNA molecules were cartridge-purified oligonucleotides that were synthesized to contain variations from the wild-type sequence at two distinct positions. These variations allowed the control sequences to be readily distinguished from other variants within DNA purified from a clinical sample. The sequences of the top strands of these control DNA oligonucleotides are listed in Table 7. Bottom strands were also synthesized corresponding to the reverse complements of these 40 sequences. In order to make the control DNA as similar as possible to the clinically-derived DNA, both strands were annealed to make them double-stranded before adding them to the primer-extension reaction. The double-stranded DNA was quantified by UV spectrometry and then diluted to the desired concentration. To each PCR, approximately 200 copies of the double-stranded control DNA fragments corresponding to each of the 40 gene target sites were added.

The Round 1 PCR amplification consisted of the following components: (1) template DNA purified from plasma and eluted in 20 microliters of Qiagen elution buffer AVE, (2) 1× Phusion® buffer HF, (3) 200 mM of each dNTP (dATP, dCTP, dGTP, and dTTP), (4) mixture of 40 reverse barcoded primers, 100 nM each, (5) mixture of 40 forward biotinylated primers, 100 nM each, (6) 200 copies of double-stranded control DNA, (7) molecular grade water as needed to make the desired total volume, and (8) Phusion® Hot Start Flex DNA polymerase, (0.04 U/μL). The total volume of each reaction was 40 microliters (for each 20μ eluted plasma DNA sample). A separate reaction was set up for each sample.

Thermal cycling was carried out on a BioRad iCycler® using the following protocol: (1) 98° C. for 45 seconds, (2) 98° C. for 10 seconds, (3) 70° C. for 30 seconds, (4) slowly cooling by 1° C. every 30 seconds down to 56° C., (5) 55° C. for 2 minutes, (6) 72° C. for 1 minute, (7) repeat steps 2 to 6 for 3 cycles total, and (8) hold temperature at 72° C. indefinitely.

As quickly as possible, while the reaction was still at 72° C., EDTA (10 mM final concentration) was added to terminate the polymerase activity. Each tube was agitated gently to ensure even mixing of the EDTA. Since the PCR products now had sample-specific barcodes attached, the products of all reactions could be pooled together into a single tube.

Purification of Round 1 PCR Products

Since the forward primers used in the Round 1 PCR contained biotin tags at their 5'-ends, these tags were incorporated into the PCR products and were used to purify the products. To capture the biotin-tagged PCR products, 10 μL of high capacity streptavidin-agarose bead slurry (Thermo-Fisher) was added (per 40 μL PCR). Thus, for example, if fifty Round 1 PCRs were performed in a volume of 40 μL each, then the volume after combining all samples would be 2 mL, and 500 μL of bead slurry would be used. Tubes were turned end-over-end constantly for at least 2 hours at room temperature to promote binding of biotinylated DNA to the streptavidin beads. Beads were then gently and briefly centrifuged at low speed, and any unbound supernatant was carefully removed, avoiding aspiration of any beads. The beads were then washed in 200 μL of buffer containing 10 mM Tris pH 7.6, 50 mM NaCl, and 1 mg/mL salmon sperm DNA ("wash buffer"). Beads were suspended in wash buffer by gentle agitation, were gently centrifuged, and then the supernatant wash buffer was discarded. A second wash was performed in the same way, except that the suspended beads were incubated at 50° C. for 25 minutes followed by 60° C. for 5 minutes while the tube was turned end-over-end to promote dissociation of any DNA molecules that may have annealed non-specifically to the biotinylated oligonucleotides. The beads were again centrifuged gently, and the supernatant wash buffer was removed.

Optionally, between the first and second washes, the beads were treated with Exonuclease I (New England Biolabs) in order to digest any single stranded DNA (including un-extended biotinylated primer) that was bound to the beads. For the tested samples, it was found that this nuclease treatment was not necessary following the first Round of PCR. For digestion, the beads were suspended in 1× Exonuclease I buffer (2 μL for every 1 μL of beads), and then Exonuclease I enzyme was added to a final concentration of 0.5 μL. The reaction was incubated at 37° C. for 30 minutes. The beads were then centrifuged, the supernatant was discarded, and the beads then were subjected to the second wash.

The captured PCR products were then eluted from the surface of the washed beads by heat-denaturation. Elution was carried out by heating the beads to 95° C. for 30 seconds directly in Round 2 PCR cocktail (as described below), gently centrifuging the beads, and harvesting the eluted DNA within the supernatant cocktail. Note that only one strand of the PCR product was eluted because the biotin-streptavidin interaction was not substantially disrupted by heating at 95° C., and thus the biotinylated strand would remain bound to the beads. Likewise, any un-extended biotinylated oligonucleotides would also remain bound to the beads.

Round 2 PCR

The second round of PCR was also performed for only a few cycles (between 2 and 4). This PCR provided additional selectivity by using a mixture of 40 nested forward primers that would specifically hybridize to the desired genomic target sequences. This step also provided a second molecular lineage tag on the other side of the mutation-prone target sequence (opposite to the barcode and MLT-1). The forward primers contained a stretch of degenerate positions, called "molecular lineage tag-2" (MLT-2), which was useful in determining which sequences had become labeled with the wrong barcode due to sequence crossover during pooled amplification. The forward primers also contained a common sequence at their 5'-ends which served as a universal primer binding site in the third and final round of PCR. This common sequence also provided some of the adapter sequences required for sequencing on the Illumina platform. The reverse primer used in Round 2 PCR had a biotin tag at its 5'-end which was used for purification of the Round 2 PCR products.

The purified Round 1 PCR products were eluted directly into a cocktail that was used for Round 2 PCR. For every 10 μL of bead slurry that was used, 40 μL of PCR cocktail was used for elution. The Round 2 PCR cocktail consisted of the following components: (1) 1× Phusion® buffer HF, (2) 200 mM of each dNTP (dATP, dCTP, dGTP, and dTTP), (3) a mixture of 40 nested forward primers, 100 nM each, (4) 10 ng/μL salmon sperm DNA, and (5) molecular grade water as needed to make the desired total volume.

After elution of the single-stranded PCR product from the beads into the above cocktail (and removal of the beads), a biotinylated universal reverse primer was added to achieve a final concentration of 200 nM. This biotinylated primer had to be added to the cocktail after removal of the streptavidin-agarose beads to prevent the biotin from binding to the beads. Finally, Phusion® Hot Start Flex DNA polymerase was added to the cocktail to a final concentration of 0.04 units per microliter, and was mixed by gently pipetting the cocktail up and down. If the total volume was greater than recommended for a single PCR tube, then the cocktail was split into the appropriate number of identical reaction volumes.

Thermal cycling was carried out on a BioRad iCycler® using the following protocol: (1) 98° C. for 45 seconds, (2) 98° C. for 10 seconds, (3) 70° C. for 30 seconds, (4) slowly cooling by 1° C. every 30 seconds down to 61° C., (5) 60° C. for 2 minutes, (6) 72° C. for 1 minute, (7) repeat steps 2 to 6 for 3 cycles total and, (8) hold temperature at 72° C. indefinitely.

As quickly as possible, while the reaction was still at 72° C., EDTA (10 mM final concentration) was added to terminate the polymerase activity. The tube was agitated gently to ensure even mixing of the EDTA.

The sequences of the 40 nested forward primers were the same as those provided in Table 10, except that the sequence "NNNNACT" in each primer was replaced by "NNNNNN". The common "ACT" sequence was removed because it led to poor sequence diversity which produced low-quality base-calls on the Illumina sequencer. Instead, the stretch of degenerate positions was increased from 4 to 6 bases to provide a greater number of sequence combinations at MLT-2. The sequence of the biotinylated reverse primer used in Round 2 PCR (called BioV2rev) was as follows: 5'-Biotin-CGAGACGGATCAAGCA GAAGACG-3' (SEQ ID NO:214).

Purification of Round 2 PCR Products

The biotin tag at the 5'-end of the reverse primer used in Round 2 PCR was used to capture and purify the products of Round 2 PCR. This step removed any un-extended forward primers, as well as many spurious products that might have been produced during the amplification, which prevented inappropriate incorporation of new MLTs during the next round of amplification.

The capture, washing, digestion, and elution of the Round 2 PCR products was performed in a manner that was essentially identical to the process described above for the purification of Round 1 PCR products. In Round 2 PCR purification, the Exonuclease I step was not optional. Thus, the beads were washed once in wash buffer at room temperature, then were treated with Exonuclease I, and then were washed a second time at elevated temperature (50° C. for 25 minutes followed by 60° C. for 5 minutes) to remove non-specific DNA. Fewer beads were used for a given volume of Round 2 PCR reaction. Five microliters of bead slurry was used for every 40 µL of PCR reaction volume.

Elution of the captured PCR products was also performed in a manner that was essentially the same as that used for purification of the Round 1 PCR products. The streptavidin-agarose beads were heated to 95° C. for 30 seconds to elute the product directly into a cocktail that was used for Round 3 PCR (described below). The biotinylated strand of the PCR product remained bound to the beads, while the opposite strand was eluted into the Round 3 PCR cocktail.

Round 3 PCR

The third and final round of PCR amplified the DNA molecules that were specifically tagged, copied, and purified in the first 2 rounds of PCR. To provide sufficient DNA for visualization by ethidium bromide staining on an agarose gel, the amount of PCR product from Round 3 had to be substantial (at least 0.5 microgram). Thus, the final PCR amplification was carried to saturation or beyond (typically 15 to 35 cycles, depending on the amount of template DNA in each sample and the total number of samples that were pooled).

In contrast to the final PCRs in Example 2 which were performed separately for each genomic target site, the final PCR in the present Example was performed in a combined reaction volume for all genomic targets and for all samples. This extremely high level of multiplexing was only possible because of the highly selective methods used for amplification and purification in the prior two rounds of PCR.

As described above, the round 2 PCR products were eluted directly into Round 3 PCR cocktail. The volume of this cocktail depended on the volume of beads used. For every 5 µL of bead slurry, 20 µL of PCR cocktail was used. The Round 3 PCR cocktail consisted of the following components: (1) 1× Phusion® buffer HF, (2) 200 mM of each dNTP (dATP, dCTP, dGTP, and dTTP), (3) Universal forward and reverse primers, 200 nM each, (4) 10 ng/µL salmon sperm DNA, and (5) molecular grade water as needed to make the desired total volume.

After elution of the single-stranded PCR product from the beads into the above cocktail, Phusion® Hot Start Flex DNA polymerase was added to the cocktail to a final concentration of 0.04 U/µL, and was mixed by gently pipetting the cocktail up and down. If the total volume was greater than recommended for a single PCR tube, then the cocktail was split into the appropriate number of identical reaction volumes. Mineral oil (20 µL) was added to the tube(s) to prevent evaporation during PCR.

Thermal cycling was carried out on a BioRad® iCycler using the following protocol: (1) 98° C. for 45 seconds, (2) 98° C. for 10 seconds, (3) 62° C. for 30 seconds, (4) 72° C. for 20 seconds, (5) repeat steps 2 to 4 for 35 cycles total, and (8) hold temperature at 4° C. indefinitely.

Soon after the reaction had reached 4° C., EDTA (10 mM final concentration) was added to terminate the polymerase activity. Since the PCR product was under mineral oil, a pipette with a filtered tip was used to evenly mix the EDTA. Special care was taken to avoid contamination of other reagents and workspaces with PCR products.

Preparation of DNA for Next-Generation Sequencing

The product of the Round 3 PCR was purified on a 2% agarose gel, as described in Example 2. Since the products were not of a homogeneous length, a somewhat diffuse band was seen on the gel. The band was cut with a few mm margin above and below to ensure inclusion of any low-intensity bands that may have been difficult to visualize. A QIAquick® Gel Extraction kit (Qiagen) was used to isolate the DNA from the gel slice. The DNA was eluted into 50 µL of EB buffer (supplied in the kit).

Next-Generation Sequencing

Next generation sequencing was performed as described in Example 2, using the Illumina HiSeq® 2000 platform. In the present example, the Illumina MiSeq® instrument was also used with similar success for samples requiring less sequence depth. In contrast to Example 2, addition of Phi-X DNA to improve sequence diversity was not necessary in the present Example because modification of the Round 2 PCR forward primers to remove the common "ACT" sequence and to lengthen MLT-2 resulted in adequate sequence diversity.

Outline of Algorithm for Sequence Analysis

Essentially the same algorithm that was described in Example 2 was applied to the data generated in Example 3. Although many of the processing steps used in Example 3 differ from those used in Example 2, the structure of the final double stranded DNA products are virtually identical. Thus, a very similar algorithm can be applied for sorting, aligning, and counting the resulting sequences. As noted above, the region of MLT-2 which was "NNNNACT" in Example 2 was replaced with "NNNNNN" in Example 3, and this change was accounted for in the modified algorithm.

To minimize the probability of mis-classifying a variant sequence as belonging to the wrong sample, MLT-1 and MLT-2 sequences were used to distinguish sequences in which barcode "cross-over" may have occurred during pooled amplification. Since a portion of MLT-1 is adjacent to the barcode sequence, and MLT-2 is on the other side of the target region (FIG. 14), molecules that undergo such cross-over between the barcode and the mutation-prone region would also undergo cross-over between MLT-1 and MLT-2 (or between the two separate regions of MLT-1). Such "crossed-over" sequences would be expected to have a low number of copies having a given combination of MLT-1 and MLT-2 sequences. In contrast, sequences arising from an authentic mutant template that remained attached to its originally assigned barcode would be expected to have greater copies of a given MLT-1 and MLT-2 combination.

The algorithm in Example 3 was modified to facilitate evaluation of the relationship between MLT-1 and MLT-2 sequence counts for each "consistent variant" and also for the wild-type sequences. In order to report these counts in a reasonably succinct format, it was necessary to bin MLT counts by powers of two. For example, an MLT-1 count of 13 would be placed into bin 4 (because 2^4 is the smallest power of 2 that is greater than or equal to 13). Thus, a report of 4×5 meant that there were five instances of counts in the range of 9 to 16. Similarly, a report of 3×6 meant that there were six instances of counts in the range of 5 to 8. For a given collection of MLT-1 counts, the associated MLT-2 counts were reported in a similar format, to the right of the MLT-1 counts and separated by colons. For example, 4×5: 2×3:1×7 meant that among 5 sets of MLT-1 sequences occurring between 9 and 16 times, there were 3 instances of MLT-2 sequences that occurred between 3 and 4 times, and 7 instances of MLT-2 sequences that occurred twice. Different MLT-1 bins were separated by a space.

Results

Figure 17:
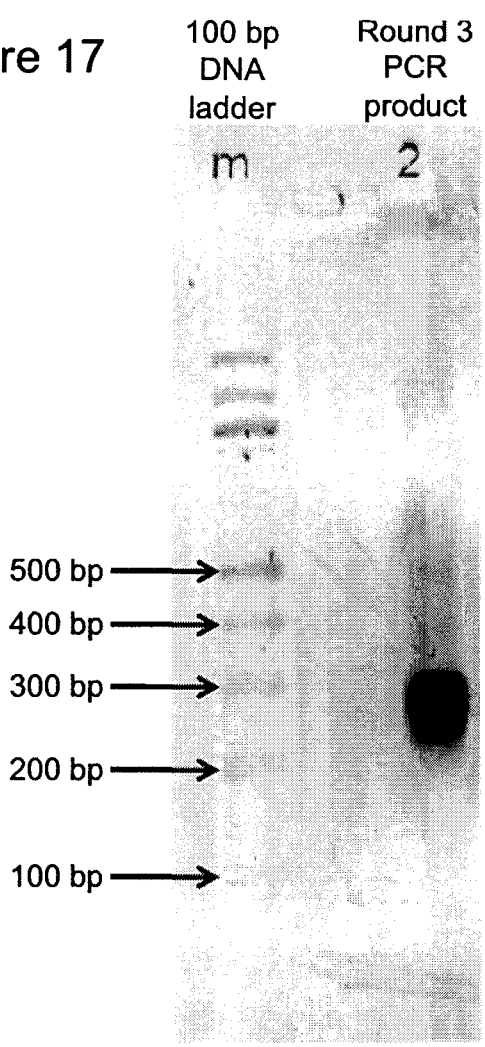
FIG. 17 shows an ethidium bromide-stained 2% agarose gel containing products of Round 3 PCR. A marker lane contained a 100 base-pair ladder for size comparison. The gel shows a diffuse band containing amplified products within the expected size range, and very little spurious product migrating at a different size.

Purified DNA that was obtained from 0.5 mL of plasma of healthy volunteers was mixed with various amounts of the control mutant oligonucleotides listed in Table 7. Between 200 and 5,000 copies of each of the 40 control oligonucleotides were added to each purified plasma DNA sample. These mixtures were subjected to 3 rounds of PCR and purification as described in the methods. The highly multiplexed Round 3 PCR in which multiple gene targets from multiple samples were amplified in a single tube, resulted in the specific production of amplicons of the expected size. As shown in FIG. 17, a relatively broad band was seen migrating at a size corresponding to between 200 and 300 base pairs on a 2% non-denaturing agarose gel (approximately centered at 250 base pairs). The primers and target regions were of variable length, and the amplification products spanned a range of sizes. Extensive testing of negative controls confirmed that these products were specific and were absent when mouse DNA or no template DNA was substituted for human plasma DNA in Round 1 PCR.

The gel-extracted PCR products were subjected to next-generation sequencing using an Illumina MiSeq® instrument. The total number of raw clonal paired-end sequences was 20,511,389. After application of the various filters described above, the remaining sequences numbered 11,184, 975. The 40 different gene target regions were fairly evenly represented among the filtered sequences. The median sequence count for the 40 gene-specific regions (all barcodes) was 166,867.

After processing of the sequence data using the computer algorithm described above, control mutant oligonucleotides that were spiked into the plasma DNA were identified and quantified. Importantly, they were readily distinguished from the vast majority of errors introduced during amplification, processing, or sequencing. As observed previously in Example 1 and Example 2, the sequence redundancy provided by the clonal overlapped paired-end reads was able to virtually eliminate sequencer-generated errors in the mutation-prone sequence regions. The "consistent variants" were then analyzed for the distribution of their associated MLT sequences. As an example, the summary output for analysis of sequences belonging to a single barcode and target gene region KRAS-2 (region surrounding codon 61 of the KRAS gene) is shown in FIG. 18. In this sample, approximately 200 copies of the mutant oligonucleotides were spiked in (each having two distinct mutations relative to the wild-type sequence). The mismatches of the "consistent variants" relative to the reference wild-type sequence are displayed in the lower portion of FIG. 18. This single data bin contained 13,315 total sequences, of which 10,815 were exact matches to the wild-type sequence and 1,767 were exact matches to the spiked-in mutant sequence (an exact match requires that the overlapping portions of the paired-reads agree with each other). The spiked-in mutant sequences comprised approximately 10% to 15% of the total DNA in the sample, which is in the expected range (there should be approximately 1,000 to 2,000 genome copies of fragmented DNA in 0.5 mL of plasma). The counts of MLT-1 and MLT-2 are reported for each "consistent variant" according to the scheme described above. The MLT-1 counts associated with sequences arising from the spiked-in control mutant oligonucleotides were generally higher than those associated with other variant sequences, as expected. This made it possible to distinguish many of the "consistent variants" arising from polymerase misincorporations that might have otherwise been mistaken for sequences arising from true mutant template molecules. Analysis of MLT-2 counts associated each group of MLT-1 counts provided insight into the efficiency of molecular tagging and copying at PCR Rounds 1 and 2. It also helped to distinguishing variants assigned to the wrong sample due to barcode cross-over during pooled amplification.

Example 4: Splint-Mediated Enzymatic Ligation of Modular Oligonucleotide Segments In this example, an alternative approach is described for the production of mixtures of primers in which each mixture had a common 5' barcode segment and a variety of gene-specific 3' segments. Enzymatic ligation was used to concentrate modular oligonucleotide segments. More specifically, in each ligation, a uniquely barcoded 5' oligonucleotide segment was ligated to a uniform mixture of different gene-specific 3' segments. A DNA splint was used to faciliate the ligation.

Gene-specific oligonucleotides with a common sequence at the 5'-end (and a 5'-phosphate group added during oligonucleotide synthesis) were mixed in equimolar ratios. The uniform mixture was divided into separate tubes and was ligated to a uniquely barcoded oligonucleotide in each tube using a biotin-tagged DNA splint as illustrated in FIG. 13. The sequences of the 5'-phosphorylated gene-specific oligonucleotides are listed in Table 13.

TABLE 13

List of chemically 5'-phosphorylated gene-specific oligonucleotides used for splint-mediated modular ligation.

| Name | DNA Sequence | |
|---|---|---|
| Ph-TP53-1 | X-AGACGTGTGCTCTTCCGATCTGTGCTGTGACTGCTTG | 298 |
| Ph-TP53-2 | X-AGACGTGTGCTCTTCCGATCTAGCACATGACGGAGGTT | 299 |
| Ph-TP53-3 | X-AGACGTGTGCTCTTCCGATCTCAAATACTCCACACGCAAATT | 300 |

TABLE 13-continued

List of chemically 5'-phosphorylated gene-specific oligonucleotides used for splint-mediated modular ligation.

| Name | DNA Sequence | |
|---|---|---|
| Ph-TP53-4 | X-AGACGTGTGCTCTTCCGATCTATTTGGATGACAGAAACACTT | 301 |
| Ph-TP53-5 | X-AGACGTGTGCTCTTCCGATCTTGTGATGATGGTGAGGATGG | 302 |
| Ph-TP53-6 | X-AGACGTGTGCTCTTCCGATCTGGGACGGAACAGCTTTGAG | 303 |
| Ph-PIK3CA-1 | X-AGACGTGTGCTCTTCCGATCTGCAATTTCTACACGAGATCCTCT | 304 |
| Ph-PIK3CA-2 | X-AGACGTGTGCTCTTCCGATCTCTTTGGAGTATTTCATGAAACAAATGA | 305 |
| Ph-BRAF | X-AGACGTGTGCTCTTCCGATCTACAGTAAAAATAGGTGATTTTGGTCTA | 306 |
| Ph-FoxL2 | X-AGACGTGTGCTCTTCCGATCTGCAACTACTGGACGCTGGAC | 307 |
| Ph-GNAS | X-AGACGTGTGCTCTTCCGATCTCAATTTTGTTTCAGGACCTGCT | 308 |
| Ph-CTNNB1 | X-AGACGTGTGCTCTTCCGATCTGGCAGCAACAGTCTTACCT | 309 |
| Ph-PPP2R1A-1 | X-AGACGTGTGCTCTTCCGATCTCCC AGC TTG GAG GCT GC | 310 |
| Ph-PPP2R1A-2 | X-AGACGTGTGCTCTTCCGATCTGCCAGGCCGCTGAAGACA | 311 |
| Ph-PTEN-1 | X-AGACGTGTGCTCTTCCGATCTGCAATTCACTGTAAAGCTGGAAAG | 312 |
| Ph-PTEN-2 | X-AGACGTGTGCTCTTCCGATCTGAAGATATATTCCTCCAATTCAGGAC | 313 |
| Ph-KIT-1 | X-AGACGTGTGCTCTTCCGATCTCGTTTCCTTTAACCACATAATTAGAATC | 314 |
| Ph-KIT-2 | X-AGACGTGTGCTCTTCCGATCTTTTCCCTTTCTCCCCACAG | 315 |
| Ph-KIT-3 | X-AGACGTGTGCTCTTCCGATCTTCCTGTAGCAAAACCAGAAATC | 316 |
| Ph-EGFR-1 | X-AGACGTGTGCTCTTCCGATCTGGTGAGAAAGTTAAAATTCCCGTC | 317 |
| Ph-EGFR-2 | X-AGACGTGTGCTCTTCCGATCTAGCATGTCAAGATCACAGATTTTG | 318 |
| Ph-EGFR-3 | X-AGACGTGTGCTCTTCCGATCTCACCTCCACCGTGCAGCT | 319 |
| Ph-AKT1 | X-AGACGTGTGCTCTTCCGATCTACCACCCGCACGTCTGT | 320 |
| Ph-ATM | X-AGACGTGTGCTCTTCCGATCTCTTCCATACTTGATTCATGATATTTTACT | 321 |
| Ph-APC | X-AGACGTGTGCTCTTCCGATCTACCTCCTCAAACAGCTCAAAC | 322 |
| Ph-FGFR3-1 | X-AGACGTGTGCTCTTCCGATCTTGGGAGATCTTCACGCTGG | 323 |
| Ph-FGFR3-2 | X-AGACGTGTGCTCTTCCGATCTCCCTGAGCGTCATCTGCC | 324 |
| Ph-FGFR3-3 | X-AGACGTGTGCTCTTCCGATCTGCTGGTGGAGGCTGACGA | 325 |
| Ph-MET-1 | X-AGACGTGTGCTCTTCCGATCTTCCCTATCAAATATGTCAACGACT | 326 |
| Ph-MET-2 | X-AGACGTGTGCTCTTCCGATCTATTTTGGTCTTGCCAGAGACA | 327 |

TABLE 13-continued

List of chemically 5'-phosphorylated gene-specific
oligonucleotides used for splint-mediated
modular ligation.

| Name | DNA Sequence | |
|---|---|---|
| Ph-STK11-1 | X-AGACGTGTGCTCTTCCGATCTATCGACTCCACCGAGGTCA | 328 |
| Ph-STK11-2 | X-AGACGTGTGCTCTTCCGATCTACTTGGAGGACCTGCACG | 329 |
| Ph-KRAS-1 | X-AGACGTGTGCTCTTCCGATCTCGTCAAGGCACTCTTGCCT | 330 |
| Ph-KRAS-2 | X-AGACGTGTGCTCTTCCGATCTGATATTCTCGACACAGCAGGT | 331 |
| Ph-NRAS-1 | X-AGACGTGTGCTCTTCCGATCTTCAGTGCGCTTTTCCCA | 332 |
| Ph-NRAS-2 | X-AGACGTGTGCTCTTCCGATCTGACATACTGGATACAGCTGGA | 333 |
| Ph-HRAS-1 | X-AGACGTGTGCTCTTCCGATCTGGTCAGCGCACTCTTGCCC | 334 |
| Ph-HRAS-2 | X-AGACGTGTGCTCTTCCGATCTCATCCTGGATACCGCCGGC | 335 |
| Ph-KRAS-C | X-AGACGTGTGCTCTTCCGATCTCCTGTTTATAATATTGACAAAACACCT | 336 |
| Ph-BRAF-C | X-AGACGTGTGCTCTTCCGATCTCAGGACAAAGTCCGGATTGA | 337 |

X = 5'-posphate added chemically during oligonucleotide synthesis.

The sequences of the 96 different barcoded oligonucleotides contained the following common sequence, with each oligonucleotide containing a different 8-nucleotide barcode from the list in Table 6 inserted into the position marked [BC1-96]:

(SEQ ID NO: 215)
5'-CGAGACGGATCAAGCAGAAGACGGCATACGAGAT[BC1-

96]NNNNNNNGTGACTGGAGTTC-3'

The sequence of the 3'-biotin tagged splint oligonucleotide was:

(SEQ ID NO: 216)
5'-ATCGGAAGAGCACACGTCTGAACTCCAGTCACAAAAAAAAAAAAAT

CTCGTATGCCGTCTTCTGCTTGATCCG TCTCG-3'-Biotin-TEG

The barcoded oligonucleotides were cartridge purified to ensure that they were mostly full-length. They were synthesized at the 40 nmole scale, with an expected full-length yield of approximately 50 to 60%. The phosphorylated gene-specific oligonucleotides and splint oligonucleotide were purified on a polyacrylamide gel (as described in Sambrook J J, et al., *Molecular Cloning: A Laboratory Manual*, Cold Spring Harbor Press, 2001).

The ligation reactions were carried out using the following conditions:

| | |
|---|---|
| Molecular grade water | 38.15 μL |
| Dithiothreitol (100 mM stock) | 2.5 μL |
| NEB Ligase buffer (10x) | 10 μL |
| 5'-Phosphorylated oligo mix (263 uM stock) (7 uM final) | 2.7 μL |
| splint oligo (248 uM stock) (14 uM final) | 5.65 μL |
| Barcoded oligo (50 uM stock) (20 uM final) | 40 μL |
| Total | 100 μL |

The 5'-phosphorylated oligonucleotide mix consisted of an equimolar mixture of 40 different gene-specific oligos. 96 different reactions were set up in separate tubes, each one with a different barcoded oligonucleotide. To anneal the oligonucleotides to the splint, the reaction mixes were heated on a thermal cycler as follows: 95° C. for 30 sec, 70° C. for 20 sec, then the temperature was decreased by 2.5° C. every 20 sec until the samples reached 25° C.

Then 2 μL of T4 DNA Ligase (400,000 U/mL, New England Biolabs) was added to each reaction, and after mixing, the reactions were incubated at 25° C. for at least 2 hours.

Then 20 μL of streptavidin-agarose high-capacity bead slurry (Thermo Scientific, Pierce) was added, and the samples were incubated at room temperature while being turned end-over-end on a rotisserie for at least 2 hrs.

The streptavidin-agarose beads were then washed three times with 200 microliters of Tris 10 mM pH 7.6, NaCl 50 mM. The ligated (and unligated) DNA molecules were then eluted from the beads by heat-denaturation of the DNA duplex. The majority of the biotinylated splint oligo remained attached to the beads because the biotin-steptavidin interaction was not significantly disrupted by heating at 95° C. The elution was carried out in 2 steps. In the first step, the beads were heated to 95° C. in 40 microliters of the Tris/NaCl buffer for 30 seconds. The beads were quickly spun down by brief centrifugation, and then the supernatant containing was removed and stored. In the second step, the same elution process was carried out, but with heating to 95° C. for 45 seconds in order to remove any remaining ligated DNA from the beads. The supernatants containing the ligated (and unligated) DNA from the first and second elution steps were combined into a total volume of 80 microliters. This process yielded approximately 600 to 700 picomoles of ligated oligonucleotides in 80 microliters of buffer, for a final concentration of approximately 7-8 micromolar.

The invention claimed is:

1. An assay method of measuring low-abundance nucleic acid variants comprising:
   a) generating synthetic oligonucleotides comprising a plurality of molecular lineage tags (MLTs);
   b) attaching the plurality of MLTs to copies of a plurality of template nucleic acids that are derived from a single patient sample;
      i) wherein each copy of the template nucleic acids is attached to one molecular lineage tag (MLT), enabling different copies of the template nucleic acids to be distinguished from each other based on the MLT that is attached, and
      ii) wherein the template nucleic acids comprise a plurality of mutation-prone genomic regions;
   c) amplifying the copies of the template nucleic acids comprising the MLTs using a multiplexed polymerase chain reaction (PCR), wherein the plurality of mutation-prone genomic regions are simultaneously amplified;
   d) sequencing all or a subset of the amplified template nucleic acids comprising the attached MLTs to obtain a plurality of read sequences, wherein each read sequence comprises a template-derived read sequence attached to a MLT read sequence;
   e) mapping the template-derived read sequences to known genomic reference sequences;
   f) identifying a template-derived sequence as a putative variant sequence if the template-derived read sequence does not exactly match the genomic reference sequence to which it is mapped; and
   g) quantifying the putative variant sequences that have a high-probability of being true low-abundance nucleic acid variants in the patient sample based on analysis of the diversity and copy number of the MLT read sequences attached to the template-derived read sequences.

2. An assay method of reducing errors in differentiating true low-abundance nucleic acid variants from nucleotide misincorporations that occur during amplification or from nucleotide misreads that occur during sequencing, the method comprising:
   a) labeling template nucleic acids derived from patient samples with synthetic oligonucleotides comprising molecular lineage tags (MLTs), wherein the template nucleic acid is capable of being labeled with any one of a plurality of MLT sequences and an MLT sequence is capable of being attached to more than one template nucleic acid;
   b) amplifying the labeled template nucleic acids derived from patient samples;
   c) sequencing at least some of the amplified nucleic acids derived from patient samples, wherein the number of copies of template-derived read sequences and attached MLT read sequences that is generated is several-fold greater than the number of copies of labeled template nucleic acids derived from patient samples;
   d) identifying a putative variant sequence from among the template-derived read sequences when the template-derived read sequence does not perfectly match a genomic reference sequence to which it is mapped; and
   e) reducing the errors in differentiating which putative variant sequences are derived from true low-abundance nucleic acid variants in the patient sample based on analysis of the diversity and copy number of the MLT read sequences attached to the template-derived read sequences.

3. The method of claim 1 or claim 2, wherein the MLT is 2 to 10 nucleotides.

4. The method of claim 3, wherein the MLT is 6 to 8 nucleotides.

5. The assay method of claim 1 or claim 2, further comprising a second round of multiplexed PCR, wherein the second round of multiplex PCR comprises nested gene-specific oligonucleotide primers.

6. The assay method of claim 1 or claim 2, wherein the template nucleic acid is circulating tumor DNA (ctDNA) or is derived from tumor tissue.

7. The assay method of claim 1 or claim 2, further comprising clonal overlapping paired-end sequencing, wherein sequencing base-calls are verified by comparing overlapping template-derived read sequences obtained from opposite strands of a clonal sequence.

8. The assay method of claim 1 or claim 2, wherein the low-abundance nucleic acid variant is measured before and after a treatment.

9. An assay method for early barcoding of a plurality of genomic target sequences from a plurality of patient samples using synthetic oligonucleotides, the method comprising:
   a) producing a plurality of modular primer mixes, wherein each modular primer mix is produced by attaching a 5' oligonucleotide segment comprising a unique sample-specific barcode and a plurality of MLTs to a pool of 3' oligonucleotide segments comprising a plurality of target-specific primer sequences; and
   b) copying the plurality of genomic target sequences from the plurality of patient samples by a first round of primer-extension, wherein the genomic targets within each patient sample are copied using the modular primer mix that comprises the synthetic oligonucleotides,
   wherein the synthetic oligonucleotides comprise the unique sample-specific barcode and the MLTs.

10. The assay method of claim 1 or claim 2, wherein the plurality of mutation-prone genomic regions comprise at least 40 mutation-prone genomic regions that are simultaneously amplified.

11. The assay method of claim 1, further comprising analyzing the plurality of samples simultaneously.

12. The assay method of claim 11, wherein simultaneously analyzing the plurality of patient samples is enabled by attaching unique sample-specific barcodes to copies of the plurality of mutation-prone genomic targets within each sample.

13. The assay method of claim 9, wherein the MLT is 6 to 8 nucleotides.

14. The assay method of claim 9, wherein each unique sample-specific barcode in the set differs from every other unique sample-specific barcode in the set at a minimum of 2 distinct positions.

* * * * *

SEQUENCE LISTING

<160> NUMBER OF SEQ ID NOS: 370

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
ggcctgctga aaatgactga atataaac                                          28

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
ttcgtccaca aaatgattct gaattagc                                          28

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
tcatgaagac ctcacagtaa aaataggtg                                         29

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
cacaaaatgg atccagacaa ctgttc                                            26

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gtactggtga aaacaccgca gcat                                              24

<210> SEQ ID NO 6
<211> LENGTH: 28
<212> TYPE: DNA
<213> ORGANISM: Artificial Sequence
<220> FEATURE:
<223> OTHER INFORMATION: primer

<400> SEQUENCE: 6
cttactttgc ctccttctgc atggtatt                                          28

<210> SEQ ID NO 7
<211> LENGTH: 43
<212> TYPE: DNA
<213> ORGANISM: Artificial Sequence

```
<220> FEATURE:
<223> OTHER INFORMATION: primer
<220> FEATURE:
<221> NAME/KEY: misc_feature
<222> LOCATION: (3)..(8)
<223> OTHER INFORMATION: the stretch nnnnnn represents any one of the 16
      forward barcodes defined in Table 2

<400> SEQUENCE: 7
ggnnnnnncg aacagtctcc gaatataaac ttgtggtagt tgg            43

<210> SEQ ID NO 8
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(8)
<223> OTHER INFORMATION: the stretch nnnnnn represents any one of the 16
      reverse barcodes defined in Table 2

<400> SEQUENCE: 8
gcnnnnnngg atgagtgcag tgaattagct gtatcgtcaa g              41

<210> SEQ ID NO 9
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(8)
<223> OTHER INFORMATION: the stretch nnnnnn represents any one of the 16
      forward barcodes defined in Table 2

<400> SEQUENCE: 9
ggnnnnnncg aacagtctcc aaataggtga ttttggtcta gc             42

<210> SEQ ID NO 10
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(8)
<223> OTHER INFORMATION: the stretch nnnnnn represents any one of the 16
      reverse barcodes defined in Table 2

<400> SEQUENCE: 10
gcnnnnnngg atgagtgcag ccagacaact gttcaaactg a              41

<210> SEQ ID NO 11
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(8)
<223> OTHER INFORMATION: the stretch nnnnnn represents any one of the 16
      forward barcodes defined in Table 2

<400> SEQUENCE: 11
ggnnnnnncg aacagtctcc cagcatgtca agatcacaga tt             42
```

<210> SEQ ID NO 12
<211> LENGTH: 41
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(8)
<223> OTHER INFORMATION: the stretch nnnnnn represents any one of the 16
      reverse barcodes defined in Table 2

<400> SEQUENCE: 12
gcnnnnnngg atgagtgcag gcatggtatt ctttctcttc c                    41

<210> SEQ ID NO 13
<211> LENGTH: 35
<212> TYPE: DNA
<213> ORGANISM: Artificial Sequence
<220> FEATURE:
<223> OTHER INFORMATION: synthetic construct

<400> SEQUENCE: 13
ccaactacca caagtttata ttcggagact gttcg                           35

<210> SEQ ID NO 14
<211> LENGTH: 34
<212> TYPE: DNA
<213> ORGANISM: Artificial Sequence
<220> FEATURE:
<223> OTHER INFORMATION: synthetic construct

<400> SEQUENCE: 14
aatctgtgat cttgacatgc tgggagactg ttcg                            34

<210> SEQ ID NO 15
<211> LENGTH: 34
<212> TYPE: DNA
<213> ORGANISM: Artificial Sequence
<220> FEATURE:
<223> OTHER INFORMATION: synthetic construct

<400> SEQUENCE: 15
gctagaccaa aatcacctat ttggagactg ttcg                            34

<210> SEQ ID NO 16
<211> LENGTH: 20
<212> TYPE: DNA
<213> ORGANISM: Artificial Sequence
<220> FEATURE:
<223> OTHER INFORMATION: synthetic construct

<400> SEQUENCE: 16
ggaaccttcg aacagtctcc                                            20

<210> SEQ ID NO 17
<211> LENGTH: 20
<212> TYPE: DNA
<213> ORGANISM: Artificial Sequence
<220> FEATURE:
<223> OTHER INFORMATION: synthetic construct

<400> SEQUENCE: 17
ggaacgtacg aacagtctcc                                            20

```
<210> SEQ ID NO 18
<211> LENGTH: 20
<212> TYPE: DNA
<213> ORGANISM: Artificial Sequence
<220> FEATURE:
<223> OTHER INFORMATION: synthetic construct

<400> SEQUENCE: 18
ggaagcatcg aacagtctcc                                                    20

<210> SEQ ID NO 19
<211> LENGTH: 20
<212> TYPE: DNA
<213> ORGANISM: Artificial Sequence
<220> FEATURE:
<223> OTHER INFORMATION: synthetic construct

<400> SEQUENCE: 19
ggaaggaacg aacagtctcc                                                    20

<210> SEQ ID NO 20
<211> LENGTH: 20
<212> TYPE: DNA
<213> ORGANISM: Artificial Sequence
<220> FEATURE:
<223> OTHER INFORMATION: synthetic construct

<400> SEQUENCE: 20
ggatccatcg aacagtctcc                                                    20

<210> SEQ ID NO 21
<211> LENGTH: 20
<212> TYPE: DNA
<213> ORGANISM: Artificial Sequence
<220> FEATURE:
<223> OTHER INFORMATION: synthetic construct

<400> SEQUENCE: 21
ggatcgaacg aacagtctcc                                                    20

<210> SEQ ID NO 22
<211> LENGTH: 20
<212> TYPE: DNA
<213> ORGANISM: Artificial Sequence
<220> FEATURE:
<223> OTHER INFORMATION: synthetic construct

<400> SEQUENCE: 22
ggatgcaacg aacagtctcc                                                    20

<210> SEQ ID NO 23
<211> LENGTH: 20
<212> TYPE: DNA
<213> ORGANISM: Artificial Sequence
<220> FEATURE:
<223> OTHER INFORMATION: synthetic construct

<400> SEQUENCE: 23
ggatggtacg aacagtctcc                                                    20

<210> SEQ ID NO 24
<211> LENGTH: 20
<212> TYPE: DNA
<213> ORGANISM: Artificial Sequence
<220> FEATURE:
<223> OTHER INFORMATION: synthetic construct
```

```
<400> SEQUENCE: 24
ggtacctacg aacagtctcc                                                    20

<210> SEQ ID NO 25
<211> LENGTH: 20
<212> TYPE: DNA
<213> ORGANISM: Artificial Sequence
<220> FEATURE:
<223> OTHER INFORMATION: synthetic construct

<400> SEQUENCE: 25
ggtacgaacg aacagtctcc                                                    20

<210> SEQ ID NO 26
<211> LENGTH: 20
<212> TYPE: DNA
<213> ORGANISM: Artificial Sequence
<220> FEATURE:
<223> OTHER INFORMATION: synthetic construct

<400> SEQUENCE: 26
ggtacgttcg aacagtctcc                                                    20

<210> SEQ ID NO 27
<211> LENGTH: 20
<212> TYPE: DNA
<213> ORGANISM: Artificial Sequence
<220> FEATURE:
<223> OTHER INFORMATION: synthetic construct

<400> SEQUENCE: 27
ggtagcttcg aacagtctcc                                                    20

<210> SEQ ID NO 28
<211> LENGTH: 20
<212> TYPE: DNA
<213> ORGANISM: Artificial Sequence
<220> FEATURE:
<223> OTHER INFORMATION: synthetic construct

<400> SEQUENCE: 28
ggtaggatcg aacagtctcc                                                    20

<210> SEQ ID NO 29
<211> LENGTH: 20
<212> TYPE: DNA
<213> ORGANISM: Artificial Sequence
<220> FEATURE:
<223> OTHER INFORMATION: synthetic construct

<400> SEQUENCE: 29
ggttcgatcg aacagtctcc                                                    20

<210> SEQ ID NO 30
<211> LENGTH: 20
<212> TYPE: DNA
<213> ORGANISM: Artificial Sequence
<220> FEATURE:
<223> OTHER INFORMATION: synthetic construct

<400> SEQUENCE: 30
ggttgcatcg aacagtctcc                                                    20

<210> SEQ ID NO 31
<211> LENGTH: 20
```

<212> TYPE: DNA
<213> ORGANISM: Artificial Sequence
<220> FEATURE:
<223> OTHER INFORMATION: synthetic construct

<400> SEQUENCE: 31
ggttgctacg aacagtctcc                                          20

<210> SEQ ID NO 32
<211> LENGTH: 33
<212> TYPE: DNA
<213> ORGANISM: Artificial Sequence
<220> FEATURE:
<223> OTHER INFORMATION: synthetic construct

<400> SEQUENCE: 32
cttgacgata cagctaattc actgcactca tcc                           33

<210> SEQ ID NO 33
<211> LENGTH: 33
<212> TYPE: DNA
<213> ORGANISM: Artificial Sequence
<220> FEATURE:
<223> OTHER INFORMATION: synthetic construct

<400> SEQUENCE: 33
ggaagagaaa gaataccatg cctgcactca tcc                           33

<210> SEQ ID NO 34
<211> LENGTH: 33
<212> TYPE: DNA
<213> ORGANISM: Artificial Sequence
<220> FEATURE:
<223> OTHER INFORMATION: synthetic construct

<400> SEQUENCE: 34
tcagtttgaa cagttgtctg gctgcactca tcc                           33

<210> SEQ ID NO 35
<211> LENGTH: 20
<212> TYPE: DNA
<213> ORGANISM: Artificial Sequence
<220> FEATURE:
<223> OTHER INFORMATION: synthetic construct

<400> SEQUENCE: 35
gcaatcaagg atgagtgcag                                          20

<210> SEQ ID NO 36
<211> LENGTH: 20
<212> TYPE: DNA
<213> ORGANISM: Artificial Sequence
<220> FEATURE:
<223> OTHER INFORMATION: synthetic construct

<400> SEQUENCE: 36
gcaatgatgg atgagtgcag                                          20

<210> SEQ ID NO 37
<211> LENGTH: 20
<212> TYPE: DNA
<213> ORGANISM: Artificial Sequence
<220> FEATURE:
<223> OTHER INFORMATION: synthetic construct

<400> SEQUENCE: 37
gcaagatagg atgagtgcag                                                      20

<210> SEQ ID NO 38
<211> LENGTH: 20
<212> TYPE: DNA
<213> ORGANISM: Artificial Sequence
<220> FEATURE:
<223> OTHER INFORMATION: synthetic construct

<400> SEQUENCE: 38
gcaacattgg atgagtgcag                                                      20

<210> SEQ ID NO 39
<211> LENGTH: 20
<212> TYPE: DNA
<213> ORGANISM: Artificial Sequence
<220> FEATURE:
<223> OTHER INFORMATION: synthetic construct

<400> SEQUENCE: 39
gcatcatagg atgagtgcag                                                      20

<210> SEQ ID NO 40
<211> LENGTH: 20
<212> TYPE: DNA
<213> ORGANISM: Artificial Sequence
<220> FEATURE:
<223> OTHER INFORMATION: synthetic construct

<400> SEQUENCE: 40
gcatagttgg atgagtgcag                                                      20

<210> SEQ ID NO 41
<211> LENGTH: 20
<212> TYPE: DNA
<213> ORGANISM: Artificial Sequence
<220> FEATURE:
<223> OTHER INFORMATION: synthetic construct

<400> SEQUENCE: 41
gcatcaatgg atgagtgcag                                                      20

<210> SEQ ID NO 42
<211> LENGTH: 20
<212> TYPE: DNA
<213> ORGANISM: Artificial Sequence
<220> FEATURE:
<223> OTHER INFORMATION: synthetic construct

<400> SEQUENCE: 42
gcatgtatgg atgagtgcag                                                      20

<210> SEQ ID NO 43
<211> LENGTH: 20
<212> TYPE: DNA
<213> ORGANISM: Artificial Sequence
<220> FEATURE:
<223> OTHER INFORMATION: synthetic construct

<400> SEQUENCE: 43
gctaacatgg atgagtgcag                                                      20

<210> SEQ ID NO 44
<211> LENGTH: 20
<212> TYPE: DNA
<213> ORGANISM: Artificial Sequence

```
<220> FEATURE:
<223> OTHER INFORMATION: synthetic construct

<400> SEQUENCE: 44
gctagtaagg atgagtgcag                                              20

<210> SEQ ID NO 45
<211> LENGTH: 20
<212> TYPE: DNA
<213> ORGANISM: Artificial Sequence
<220> FEATURE:
<223> OTHER INFORMATION: synthetic construct

<400> SEQUENCE: 45
gctatgtagg atgagtgcag                                              20

<210> SEQ ID NO 46
<211> LENGTH: 20
<212> TYPE: DNA
<213> ORGANISM: Artificial Sequence
<220> FEATURE:
<223> OTHER INFORMATION: synthetic construct

<400> SEQUENCE: 46
gcttacaagg atgagtgcag                                              20

<210> SEQ ID NO 47
<211> LENGTH: 20
<212> TYPE: DNA
<213> ORGANISM: Artificial Sequence
<220> FEATURE:
<223> OTHER INFORMATION: synthetic construct

<400> SEQUENCE: 47
gcttcattgg atgagtgcag                                              20

<210> SEQ ID NO 48
<211> LENGTH: 20
<212> TYPE: DNA
<213> ORGANISM: Artificial Sequence
<220> FEATURE:
<223> OTHER INFORMATION: synthetic construct

<400> SEQUENCE: 48
gcttagtagg atgagtgcag                                              20

<210> SEQ ID NO 49
<211> LENGTH: 20
<212> TYPE: DNA
<213> ORGANISM: Artificial Sequence
<220> FEATURE:
<223> OTHER INFORMATION: synthetic construct

<400> SEQUENCE: 49
gcttctaagg atgagtgcag                                              20

<210> SEQ ID NO 50
<211> LENGTH: 20
<212> TYPE: DNA
<213> ORGANISM: Artificial Sequence
<220> FEATURE:
<223> OTHER INFORMATION: synthetic construct

<400> SEQUENCE: 50
gctacaatgg atgagtgcag                                              20
```

```
<210> SEQ ID NO 51
<211> LENGTH: 109
<212> TYPE: DNA
<213> ORGANISM: Artificial Sequence
<220> FEATURE:
<223> OTHER INFORMATION: synthetic construct

<400> SEQUENCE: 51
aaggcctgct gaaaatgact gaatataaac ttgtggtaga tggagctggt ggcgtaagca      60
agagtgcctt gacgatacag ctaattcaga atcattttgt ggacgaata               109

<210> SEQ ID NO 52
<211> LENGTH: 45
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 52
agacgtgtgc tcttccgatc tnnnnnnctg tgctgtgact gcttg                    45

<210> SEQ ID NO 53
<211> LENGTH: 45
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, t, or g

<400> SEQUENCE: 53
agacgtgtgc tcttccgatc tnnnnnntag cacatgacgg aggtt                    45

<210> SEQ ID NO 54
<211> LENGTH: 49
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 54
agacgtgtgc tcttccgatc tnnnnnnaca aatactccac acgcaaatt                49

<210> SEQ ID NO 55
<211> LENGTH: 50
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 55
agacgtgtgc tcttccgatc tnnnnnnata tttggatgac agaaacactt               50
```

```
<210> SEQ ID NO 56
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 56
agacgtgtgc tcttccgatc tnnnnnnctg tgatgatggt gaggatgg                   48

<210> SEQ ID NO 57
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 57
agacgtgtgc tcttccgatc tnnnnnnctg ggacggaaca gctttgag                   48

<210> SEQ ID NO 58
<211> LENGTH: 51
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 58
agacgtgtgc tcttccgatc tnnnnnntgc aatttctaca cgagatcctc t               51

<210> SEQ ID NO 59
<211> LENGTH: 55
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 59
agacgtgtgc tcttccgatc tnnnnnntct ttggagtatt tcatgaaaca aatga           55

<210> SEQ ID NO 60
<211> LENGTH: 55
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 60
agacgtgtgc tcttccgatc tnnnnnnaac agtaaaaata ggtgattttg gtcta           55
```

```
<210> SEQ ID NO 61
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 61
agacgtgtgc tcttccgatc tnnnnnntgc aactactgga cgctggac                48

<210> SEQ ID NO 62
<211> LENGTH: 51
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 62
agacgtgtgc tcttccgatc tnnnnnnctc aatttgttt caggacctgc t             51

<210> SEQ ID NO 63
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 63
agacgtgtgc tcttccgatc tnnnnnnctg gcagcaacag tcttacct                48

<210> SEQ ID NO 64
<211> LENGTH: 45
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 64
agacgtgtgc tcttccgatc tnnnnnnacc cagcttggag gctgc                   45

<210> SEQ ID NO 65
<211> LENGTH: 46
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 65
agacgtgtgc tcttccgatc tnnnnnnagc caggccgctg aagaca                  46
```

```
<210> SEQ ID NO 66
<211> LENGTH: 52
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 66
agacgtgtgc tcttccgatc tnnnnnnggc aattcactgt aaagctggaa ag          52

<210> SEQ ID NO 67
<211> LENGTH: 55
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 67
agacgtgtgc tcttccgatc tnnnnnnatg aagatatatt cctccaattc aggac       55

<210> SEQ ID NO 68
<211> LENGTH: 56
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 68
agacgtgtgc tcttccgatc tnnnnnngcg tttcctttaa ccacataatt agaatc      56

<210> SEQ ID NO 69
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 69
agacgtgtgc tcttccgatc tnnnnnngtt ttccctttct ccccacag              48

<210> SEQ ID NO 70
<211> LENGTH: 51
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 70
```
agacgtgtgc tcttccgatc tnnnnnngtt cctgtagcaa aaccagaaat c    51

<210> SEQ ID NO 71
<211> LENGTH: 52
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 71
agacgtgtgc tcttccgatc tnnnnnncgg tgagaaagtt aaaattcccg tc    52

<210> SEQ ID NO 72
<211> LENGTH: 52
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 72
agacgtgtgc tcttccgatc tnnnnnnaag catgtcaaga tcacagattt tg    52

<210> SEQ ID NO 73
<211> LENGTH: 47
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 73
agacgtgtgc tcttccgatc tnnnnnnctc acctccaccg tgcagct    47

<210> SEQ ID NO 74
<211> LENGTH: 45
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 74
agacgtgtgc tcttccgatc tnnnnnngac cacccgcacg tctgt    45

<210> SEQ ID NO 75
<211> LENGTH: 57
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 75

```
agacgtgtgc tcttccgatc tnnnnnntct tccatacttg attcatgata ttttact        57

<210> SEQ ID NO 76
<211> LENGTH: 49
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 76
agacgtgtgc tcttccgatc tnnnnnngac ctcctcaaac agctcaaac              49

<210> SEQ ID NO 77
<211> LENGTH: 47
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 77
agacgtgtgc tcttccgatc tnnnnnnatg ggagatcttc acgctgg                47

<210> SEQ ID NO 78
<211> LENGTH: 46
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 78
agacgtgtgc tcttccgatc tnnnnnntcc ctgagcgtca tctgcc                 46

<210> SEQ ID NO 79
<211> LENGTH: 46
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 79
agacgtgtgc tcttccgatc tnnnnnncgc tggtggaggc tgacga                 46

<210> SEQ ID NO 80
<211> LENGTH: 53
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t
```

-continued

<400> SEQUENCE: 80
agacgtgtgc tcttccgatc tnnnnnngtt ccctatcaaa tatgtcaacg act    53

<210> SEQ ID NO 81
<211> LENGTH: 49
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 81
agacgtgtgc tcttccgatc tnnnnnnaat tttggtcttg ccagagaca    49

<210> SEQ ID NO 82
<211> LENGTH: 47
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 82
agacgtgtgc tcttccgatc tnnnnnntat cgactccacc gaggtca    47

<210> SEQ ID NO 83
<211> LENGTH: 47
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 83
agacgtgtgc tcttccgatc tnnnnnnata cttggaggac ctgcacg    47

<210> SEQ ID NO 84
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 84
agacgtgtgc tcttccgatc tnnnnnngtc gtcaaggcac tcttgcct    48

<210> SEQ ID NO 85
<211> LENGTH: 49
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

```
<400> SEQUENCE: 85
agacgtgtgc tcttccgatc tnnnnnncga tattctcgac acagcaggt          49

<210> SEQ ID NO 86
<211> LENGTH: 45
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 86
agacgtgtgc tcttccgatc tnnnnnnatc agtgcgcttt tccca              45

<210> SEQ ID NO 87
<211> LENGTH: 49
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 87
agacgtgtgc tcttccgatc tnnnnnntga catactggat acagctgga          49

<210> SEQ ID NO 88
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 88
agacgtgtgc tcttccgatc tnnnnnngtg gtcagcgcac tcttgccc           48

<210> SEQ ID NO 89
<211> LENGTH: 47
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 89
agacgtgtgc tcttccgatc tnnnnnntca tcctggatac cgccggc            47

<210> SEQ ID NO 90
<211> LENGTH: 56
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
```

<223> OTHER INFORMATION: n is a, c, g, or t

<400> SEQUENCE: 90
agacgtgtgc tcttccgatc tnnnnnnatc ctgtttataa tattgacaaa acacct     56

<210> SEQ ID NO 91
<211> LENGTH: 49
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(27)
<223> OTHER INFORMATION: n is a, c, g, or t

<400> SEQUENCE: 91
agacgtgtgc tcttccgatc tnnnnnnatc aggacaaagt ccggattga     49

<210> SEQ ID NO 92
<211> LENGTH: 57
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(44)
<223> OTHER INFORMATION: this stretch nnnnnnnn represents any one of the
      96 barcode sequences defined in Table 6

<400> SEQUENCE: 92
cgagacggat caagcagaag acggcatacg agatnnnnnn nnnngtgact ggagttc     57

<210> SEQ ID NO 93
<211> LENGTH: 120
<212> TYPE: DNA
<213> ORGANISM: Artificial Sequence
<220> FEATURE:
<223> OTHER INFORMATION: synthetic construct

<400> SEQUENCE: 93
tcaacaagat gttttgccaa ctggccaaga cctgccctgt gcagctgtgg gttgattcca     60
cacccccgcc cggcacccgc gtccgcgtca tgaccatcta caagcagtca cagcacatga    120

<210> SEQ ID NO 94
<211> LENGTH: 98
<212> TYPE: DNA
<213> ORGANISM: Artificial Sequence
<220> FEATURE:
<223> OTHER INFORMATION: synthetic construct

<400> SEQUENCE: 94
tcacagcaca tgacggaggt tgtgaggcgc tgccaccacc atgtgcgctg ctcagatagc     60
gatggtgagc agctggggct ggagagacga cagggctg                             98

<210> SEQ ID NO 95
<211> LENGTH: 119
<212> TYPE: DNA
<213> ORGANISM: Artificial Sequence
<220> FEATURE:
<223> OTHER INFORMATION: synthetic construct

<400> SEQUENCE: 95
acagggctgg ttgcccaggg tccccaggcc tctgattcct cactgattgc tcttaggtct     60
ggcccctcct cagcatcata tccgagtcga aggaaatttg cgtgtggagt atttggatg     119

<210> SEQ ID NO 96
<211> LENGTH: 123
<212> TYPE: DNA
<213> ORGANISM: Artificial Sequence
<220> FEATURE:
<223> OTHER INFORMATION: synthetic construct

<400> SEQUENCE: 96
gagtatttgg atgacagaaa cacttttcga cacagtgtgg tgatgcccta tgagccgcct     60
gaggtctggt ttgcaactgg ggtctctggg aggaggggtt aagggtggtt gtcagtggcc    120
ctc                                                                  123

<210> SEQ ID NO 97
<211> LENGTH: 133
<212> TYPE: DNA
<213> ORGANISM: Artificial Sequence
<220> FEATURE:
<223> OTHER INFORMATION: synthetic construct

<400> SEQUENCE: 97
ctggcctcat cttgggcctg tgttatctcc taggttggct ctgactgtac caccatccac     60
tacaacgaca tgtgtaactg ttcctgcatg ggcggcatga accggaggcc catcctcacc    120
atcatcacac tgg                                                       133

<210> SEQ ID NO 98
<211> LENGTH: 114
<212> TYPE: DNA
<213> ORGANISM: Artificial Sequence
<220> FEATURE:
<223> OTHER INFORMATION: synthetic construct

<400> SEQUENCE: 98
tactgggacg gaacagcttt gaggtgcgtg tttgtgcatg tcctgggaca gaccggcgca     60
cagaggaaga gaatctccgc aagaaagggg agcctcacca cgagctgccc ccag          114

<210> SEQ ID NO 99
<211> LENGTH: 108
<212> TYPE: DNA
<213> ORGANISM: Artificial Sequence
<220> FEATURE:
<223> OTHER INFORMATION: synthetic construct

<400> SEQUENCE: 99
caaagcaatt tctacacgag atcctctctc tgaagtcagt gagcaggaga aagattttct     60
atggagtcac aggtaagtgc taaaatggag attctctgtt tcttttttc                108

<210> SEQ ID NO 100
<211> LENGTH: 112
<212> TYPE: DNA
<213> ORGANISM: Artificial Sequence
<220> FEATURE:
<223> OTHER INFORMATION: synthetic construct

<400> SEQUENCE: 100
gaggctttgg agtatttcat gaaacaaatg aatcatacac atcatggtgg ctggacaaca     60
aaaatggatt ggatcttcca cacaattaaa cagcatgcat tgaactgaaa ag            112

```
<210> SEQ ID NO 101
<211> LENGTH: 109
<212> TYPE: DNA
<213> ORGANISM: Artificial Sequence
<220> FEATURE:
<223> OTHER INFORMATION: synthetic construct

<400> SEQUENCE: 101
cctcacagta aaataggtg attttggtct agcgacagtg aaagctcgat ggagtgggtc      60
ccatcagttt gaacagttgt ctggatccat tttgtggatg gtaagaatt               109

<210> SEQ ID NO 102
<211> LENGTH: 96
<212> TYPE: DNA
<213> ORGANISM: Artificial Sequence
<220> FEATURE:
<223> OTHER INFORMATION: synthetic construct

<400> SEQUENCE: 102
aagggcaact actggacgct ggacccgacc tgcgcagaca tgttcgagaa gggcaactac      60
cggcgccgcc gccgcatgaa gaggcccttc cggccg                                96

<210> SEQ ID NO 103
<211> LENGTH: 103
<212> TYPE: DNA
<213> ORGANISM: Artificial Sequence
<220> FEATURE:
<223> OTHER INFORMATION: synthetic construct

<400> SEQUENCE: 103
acctcaattt tgtttcagga cctgcttcac tgccgtatcc tgacttctgg aatctttgag      60
accaagttcc aggtggacaa agtcaacttc cagtaagcca act                       103

<210> SEQ ID NO 104
<211> LENGTH: 123
<212> TYPE: DNA
<213> ORGANISM: Artificial Sequence
<220> FEATURE:
<223> OTHER INFORMATION: synthetic construct

<400> SEQUENCE: 104
cactggcagc aacagtctta cctggactct ggaatccatt ctgatgccac taccacagat      60
ccttctctga gtggtaaagg caatcctgag gaagaggatg tggatacctc ccaagtcctg     120
tat                                                                   123

<210> SEQ ID NO 105
<211> LENGTH: 108
<212> TYPE: DNA
<213> ORGANISM: Artificial Sequence
<220> FEATURE:
<223> OTHER INFORMATION: synthetic construct

<400> SEQUENCE: 105
ctgcctgctg cctcaggatc cccgtccccg actcccaggt acttccggaa cctgtgctca      60
gatgacaccc ccacggtgcg gcggaccgca gcctccaagc tggggag                  108

<210> SEQ ID NO 106
<211> LENGTH: 100
<212> TYPE: DNA
<213> ORGANISM: Artificial Sequence
<220> FEATURE:
```

<223> OTHER INFORMATION: synthetic construct

<400> SEQUENCE: 106
ctgcgccagg ccgctgaaga caagacctgg cgcatccgct acatggtggc tgacaagttc    60
acagaggtag atgagcgacc gttgacattg tcccactggt    100

<210> SEQ ID NO 107
<211> LENGTH: 116
<212> TYPE: DNA
<213> ORGANISM: Artificial Sequence
<220> FEATURE:
<223> OTHER INFORMATION: synthetic construct

<400> SEQUENCE: 107
tgcagcaatt cactgtaaag ctggaaaggg acgaacaggt gtaatgacat gtgcatattt    60
attacatcgg ggcaaatttt taaaggcaca agaggcccta gatttctatg gggaag    116

<210> SEQ ID NO 108
<211> LENGTH: 111
<212> TYPE: DNA
<213> ORGANISM: Artificial Sequence
<220> FEATURE:
<223> OTHER INFORMATION: synthetic construct

<400> SEQUENCE: 108
aggtgaagat atattcctcc aattcaggac cctcacgacg ggtagacaag ttcatgtact    60
ttgagttccc tcagccgtta cctgtgtgtg gtgatatcaa agtagagttc t    111

<210> SEQ ID NO 109
<211> LENGTH: 118
<212> TYPE: DNA
<213> ORGANISM: Artificial Sequence
<220> FEATURE:
<223> OTHER INFORMATION: synthetic construct

<400> SEQUENCE: 109
gagacttggc agccagaaat atcctcctta ctcatggtcg gatcacaaag atttgtgatt    60
ttggtctagc catagacatc acgaatgatt ctaattatgt ggttaaagga aacgtgag    118

<210> SEQ ID NO 110
<211> LENGTH: 129
<212> TYPE: DNA
<213> ORGANISM: Artificial Sequence
<220> FEATURE:
<223> OTHER INFORMATION: synthetic construct

<400> SEQUENCE: 110 tattttccc tttctcccca cagaaaccta tgtatgaagt acagtggaag gatgttgagg    60
agataaatgg aaacaattat gtttacatag acccaacaca acttccttat gatcacaaat    120
gggagtttc    129

<210> SEQ ID NO 111
<211> LENGTH: 108
<212> TYPE: DNA
<213> ORGANISM: Artificial Sequence
<220> FEATURE:
<223> OTHER INFORMATION: synthetic construct

<400> SEQUENCE: 111
gttttcctgt agcaaaacca gaaatcctga cttacgacag gctagtgaat ggcatgctcc    60
aatgtgtggc agcaggattc ccagagccca caatagattg gtatttttt    108

<210> SEQ ID NO 112
<211> LENGTH: 114
<212> TYPE: DNA
<213> ORGANISM: Artificial Sequence
<220> FEATURE:
<223> OTHER INFORMATION: synthetic construct

<400> SEQUENCE: 112
agaaggtgag aaagttaaaa ttcccgtcgc tatgaaggaa ttaagagaag caacatctcc    60
gtaagccaac aaggaaatcc tcgatgtgag tttctgcttt gctgtgtggg ggtc          114

<210> SEQ ID NO 113
<211> LENGTH: 102
<212> TYPE: DNA
<213> ORGANISM: Artificial Sequence
<220> FEATURE:
<223> OTHER INFORMATION: synthetic construct

<400> SEQUENCE: 113
ccgcagcatg tcaagatcac agattttggg ctggacaaac agctgggtgc ggaagagaaa    60
gaataccatg cagaaggagg caaagtaagg aggtggcttt ag                       102

<210> SEQ ID NO 114
<211> LENGTH: 84
<212> TYPE: DNA
<213> ORGANISM: Artificial Sequence
<220> FEATURE:
<223> OTHER INFORMATION: synthetic construct

<400> SEQUENCE: 114
gcctcacctc caccgtgcag ctcatgacgt agctcatgcc cttcggctgc ctcctggact    60
atgtccggga acacaaagac aata                                           84

<210> SEQ ID NO 115
<211> LENGTH: 87
<212> TYPE: DNA
<213> ORGANISM: Artificial Sequence
<220> FEATURE:
<223> OTHER INFORMATION: synthetic construct

<400> SEQUENCE: 115
tctcaccacc cgcacgtctg tagaggacta catcaagacc tggcggccac gctacttcct    60
cctcaagaat gatggcacct tcattgg                                        87

<210> SEQ ID NO 116
<211> LENGTH: 116
<212> TYPE: DNA
<213> ORGANISM: Artificial Sequence
<220> FEATURE:
<223> OTHER INFORMATION: synthetic construct

<400> SEQUENCE: 116
tgtacttcca tacttgattc atgatatttt actcctagat acgaatgaat catggagaaa    60
tctgctttct acacatgttc agggattttt caccagctgt cttcgacact tctcgc        116

<210> SEQ ID NO 117
<211> LENGTH: 97
<212> TYPE: DNA
<213> ORGANISM: Artificial Sequence
<220> FEATURE:
<223> OTHER INFORMATION: synthetic construct

```
<400> SEQUENCE: 117
caccacctcc tcaaacagct caaaccatgc gataagtacc taaaaataaa gcacctactg    60
ctgaaaagag agagagtgga cctaagcaag ctgcagt                             97

<210> SEQ ID NO 118
<211> LENGTH: 104
<212> TYPE: DNA
<213> ORGANISM: Artificial Sequence
<220> FEATURE:
<223> OTHER INFORMATION: synthetic construct

<400> SEQUENCE: 118
gctctgggag atcttcacgc tgggggactc cccgtatccc ggcatccctg tggaggagct    60
cttcaagctg ctgaaggagg gccaccgcat ggacaagccc gcca                   104

<210> SEQ ID NO 119
<211> LENGTH: 110
<212> TYPE: DNA
<213> ORGANISM: Artificial Sequence
<220> FEATURE:
<223> OTHER INFORMATION: synthetic construct

<400> SEQUENCE: 119
tggccCctga gcgtcatctg cccccactga gcgctccacg caccggccca tcctgcaggc    60
ggggctgccg gccaaccaga cggcggtgct gggcagcgac gtggagttcc              110

<210> SEQ ID NO 120
<211> LENGTH: 100
<212> TYPE: DNA
<213> ORGANISM: Artificial Sequence
<220> FEATURE:
<223> OTHER INFORMATION: synthetic construct

<400> SEQUENCE: 120
aggagctggt ggaggctgac gaggcgggca gtatgtatac aggcatcctc agctacgggg    60
tgggcttctt cctgttcatc ctggtggtgg cggctgtgac                        100

<210> SEQ ID NO 121
<211> LENGTH: 115
<212> TYPE: DNA
<213> ORGANISM: Artificial Sequence
<220> FEATURE:
<223> OTHER INFORMATION: synthetic construct

<400> SEQUENCE: 121
gcattcccta tcaaatatgt caacgacttc atcaacaaga tagtcaacaa aaacaatgtg    60
agatgtctcc agcatttttta cggacccaat catgagcact gctttaatag ggtaa       115

<210> SEQ ID NO 122
<211> LENGTH: 105
<212> TYPE: DNA
<213> ORGANISM: Artificial Sequence
<220> FEATURE:
<223> OTHER INFORMATION: synthetic construct

<400> SEQUENCE: 122
gctgattttg gtcttgccag agacatgtat cataaacaat actatagtgt acacaacaaa    60
acaggtgcaa agctgccagt gaagtggatg gctttggaaa gtctg                   105

<210> SEQ ID NO 123
<211> LENGTH: 130
```

-continued

```
<212> TYPE: DNA
<213> ORGANISM: Artificial Sequence
<220> FEATURE:
<223> OTHER INFORMATION: synthetic construct

<400> SEQUENCE: 123
ccgcatcgac tccaccgagg tcatctacca gccgagccgc atgcgggcca agctcatcgg     60
caagtacctg atgggggacc tgctggggga aggctcttac ggcaaggtga aggaggtgct    120
ggactcggag                                                            130

<210> SEQ ID NO 124
<211> LENGTH: 110
<212> TYPE: DNA
<213> ORGANISM: Artificial Sequence
<220> FEATURE:
<223> OTHER INFORMATION: synthetic construct

<400> SEQUENCE: 124
ccgtacttgg aggacctgca cggcgcggat gaggacgagg accacttcga catcgaggat     60
gacatcatct acactcagga cttcacggtg cccggtgagt ctggcggggg              110

<210> SEQ ID NO 125
<211> LENGTH: 107
<212> TYPE: DNA
<213> ORGANISM: Artificial Sequence
<220> FEATURE:
<223> OTHER INFORMATION: synthetic construct

<400> SEQUENCE: 125
tatagtcaca ttttcattat ttttattata aggcctgctg aaaatgactg aatataaact     60
tgtggtagtt gcagatggtg gcgtaggcaa gagtgccttg acgatac                  107

<210> SEQ ID NO 126
<211> LENGTH: 109
<212> TYPE: DNA
<213> ORGANISM: Artificial Sequence
<220> FEATURE:
<223> OTHER INFORMATION: synthetic construct

<400> SEQUENCE: 126
cttggatatt ctcgacacag caggtcaaga cgagtactgt gcaatgaggg accagtacat     60
gaggactggg gagggctttc tttgtgtatt tgccataaat aatactaaa               109

<210> SEQ ID NO 127
<211> LENGTH: 125
<212> TYPE: DNA
<213> ORGANISM: Artificial Sequence
<220> FEATURE:
<223> OTHER INFORMATION: synthetic construct

<400> SEQUENCE: 127
tgtagatgtg gctcgccaat taaccctgat tactggtttc caacaggttc ttgctggtgt     60
gaaatgactg agtacaaact ggtcgtggat ggagcaggtg gtgttgggaa aagcgcactg    120
acaat                                                                125

<210> SEQ ID NO 128
<211> LENGTH: 113
<212> TYPE: DNA
<213> ORGANISM: Artificial Sequence
<220> FEATURE:
<223> OTHER INFORMATION: synthetic construct
```

<400> SEQUENCE: 128
gttggacata ctggatacag ctggacaaga agagcacagt gacatgagag accaatacat    60
gaggacaggc gaaggcttcc tctgtgtatt tgccatcaat aatagcaagt cat           113

<210> SEQ ID NO 129
<211> LENGTH: 118
<212> TYPE: DNA
<213> ORGANISM: Artificial Sequence
<220> FEATURE:
<223> OTHER INFORMATION: synthetic construct

<400> SEQUENCE: 129
ggtggggcag agaccctgt aggaggaccc cgggccgcag gcccctgagg agcgatgacg     60
gaatataagc tggtggtcgt ggacgccggc ggtgtgggca agagtgcgct gaccatcc      118

<210> SEQ ID NO 130
<211> LENGTH: 118
<212> TYPE: DNA
<213> ORGANISM: Artificial Sequence
<220> FEATURE:
<223> OTHER INFORMATION: synthetic construct

<400> SEQUENCE: 130
tggacatcct ggataccgcc ggccaggagt actacagcgc catgcgggac cagtacatgc    60
gcaccgggga gggcttcctg tgtgtgtttg ccatcaacaa caccaagtct tttgagga      118

<210> SEQ ID NO 131
<211> LENGTH: 122
<212> TYPE: DNA
<213> ORGANISM: Artificial Sequence
<220> FEATURE:
<223> OTHER INFORMATION: synthetic construct

<400> SEQUENCE: 131
tgttcctgtt tataatattg acaaaacacc ttagcggatg acatttaaga attctaaaag    60
tcctaatata tgtaatatat attcagttgc ctgaagagaa acataaagaa tccttttctta  120 at                                                                  122

<210> SEQ ID NO 132
<211> LENGTH: 119
<212> TYPE: DNA
<213> ORGANISM: Artificial Sequence
<220> FEATURE:
<223> OTHER INFORMATION: synthetic construct

<400> SEQUENCE: 132
atgtcaggac aaagtccgga ttgaatataa ctctgcttta tattataggc ctatgaagaa    60
tacaccagca agctagatgc actccaacaa agagaacaac agttattgga atctctggg     119

<210> SEQ ID NO 133
<211> LENGTH: 22
<212> TYPE: DNA
<213> ORGANISM: Artificial Sequence
<220> FEATURE:
<223> OTHER INFORMATION: synthetic construct

<400> SEQUENCE: 133
caagatgttt tgccaactgg cc                                             22

<210> SEQ ID NO 134
<211> LENGTH: 22

```
<212> TYPE: DNA
<213> ORGANISM: Artificial Sequence
<220> FEATURE:
<223> OTHER INFORMATION: synthetic construct

<400> SEQUENCE: 134
cctgtcgtct ctccagcccc ag                                        22

<210> SEQ ID NO 135
<211> LENGTH: 20
<212> TYPE: DNA
<213> ORGANISM: Artificial Sequence
<220> FEATURE:
<223> OTHER INFORMATION: synthetic construct

<400> SEQUENCE: 135
ggctggttgc ccagggtccc                                           20

<210> SEQ ID NO 136
<211> LENGTH: 23
<212> TYPE: DNA
<213> ORGANISM: Artificial Sequence
<220> FEATURE:
<223> OTHER INFORMATION: synthetic construct

<400> SEQUENCE: 136
gccactgaca accaccctta acc                                       23

<210> SEQ ID NO 137
<211> LENGTH: 24
<212> TYPE: DNA
<213> ORGANISM: Artificial Sequence
<220> FEATURE:
<223> OTHER INFORMATION: synthetic construct

<400> SEQUENCE: 137
cctcatcttg ggcctgtgtt atct                                      24

<210> SEQ ID NO 138
<211> LENGTH: 19
<212> TYPE: DNA
<213> ORGANISM: Artificial Sequence
<220> FEATURE:
<223> OTHER INFORMATION: synthetic construct

<400> SEQUENCE: 138
gggcagctcg tggtgaggc                                            19

<210> SEQ ID NO 139
<211> LENGTH: 28
<212> TYPE: DNA
<213> ORGANISM: Artificial Sequence
<220> FEATURE:
<223> OTHER INFORMATION: synthetic construct

<400> SEQUENCE: 139
aagaaacaga gaatctccat tttagcac                                  28

<210> SEQ ID NO 140
<211> LENGTH: 28
<212> TYPE: DNA
<213> ORGANISM: Artificial Sequence
<220> FEATURE:
<223> OTHER INFORMATION: synthetic construct

<400> SEQUENCE: 140
```
tcagttcaat gcatgctgtt taattgtg                                              28

<210> SEQ ID NO 141
<211> LENGTH: 27
<212> TYPE: DNA
<213> ORGANISM: Artificial Sequence
<220> FEATURE:
<223> OTHER INFORMATION: synthetic construct

<400> SEQUENCE: 141
cttaccatcc acaaaatgga tccagac                                               27

<210> SEQ ID NO 142
<211> LENGTH: 22
<212> TYPE: DNA
<213> ORGANISM: Artificial Sequence
<220> FEATURE:
<223> OTHER INFORMATION: synthetic construct

<400> SEQUENCE: 142
cggaagggcc tcttcatgcg gc                                                    22

<210> SEQ ID NO 143
<211> LENGTH: 27
<212> TYPE: DNA
<213> ORGANISM: Artificial Sequence
<220> FEATURE:
<223> OTHER INFORMATION: synthetic construct

<400> SEQUENCE: 143
ggcttactgg aagttgactt tgtccac                                               27

<210> SEQ ID NO 144
<211> LENGTH: 24
<212> TYPE: DNA
<213> ORGANISM: Artificial Sequence
<220> FEATURE:
<223> OTHER INFORMATION: synthetic construct

<400> SEQUENCE: 144
aggacttggg aggtatccac atcc                                                  24

<210> SEQ ID NO 145
<211> LENGTH: 23
<212> TYPE: DNA
<213> ORGANISM: Artificial Sequence
<220> FEATURE:
<223> OTHER INFORMATION: synthetic construct

<400> SEQUENCE: 145
ctgctgcctc aggatccccg tcc                                                   23

<210> SEQ ID NO 146
<211> LENGTH: 23
<212> TYPE: DNA
<213> ORGANISM: Artificial Sequence
<220> FEATURE:
<223> OTHER INFORMATION: synthetic construct

<400> SEQUENCE: 146
gtgggacaat gtcaacggtc gct                                                   23

<210> SEQ ID NO 147
<211> LENGTH: 22
<212> TYPE: DNA
<213> ORGANISM: Artificial Sequence

```
<220> FEATURE:
<223> OTHER INFORMATION: synthetic construct

<400> SEQUENCE: 147
cccatagaaa tctagggcct ct                                              22

<210> SEQ ID NO 148
<211> LENGTH: 27
<212> TYPE: DNA
<213> ORGANISM: Artificial Sequence
<220> FEATURE:
<223> OTHER INFORMATION: synthetic construct

<400> SEQUENCE: 148
ctctactttg atatcaccac acacagg                                         27

<210> SEQ ID NO 149
<211> LENGTH: 29
<212> TYPE: DNA
<213> ORGANISM: Artificial Sequence
<220> FEATURE:
<223> OTHER INFORMATION: synthetic construct

<400> SEQUENCE: 149
cttggcagcc agaaatatcc tccttactc                                       29

<210> SEQ ID NO 150
<211> LENGTH: 27
<212> TYPE: DNA
<213> ORGANISM: Artificial Sequence
<220> FEATURE:
<223> OTHER INFORMATION: synthetic construct

<400> SEQUENCE: 150
ctcccatttg tgatcataag gaagttg                                         27

<210> SEQ ID NO 151
<211> LENGTH: 24
<212> TYPE: DNA
<213> ORGANISM: Artificial Sequence
<220> FEATURE:
<223> OTHER INFORMATION: synthetic construct

<400> SEQUENCE: 151
ataccaatct attgtgggct ctgg                                            24

<210> SEQ ID NO 152
<211> LENGTH: 21
<212> TYPE: DNA
<213> ORGANISM: Artificial Sequence
<220> FEATURE:
<223> OTHER INFORMATION: synthetic construct

<400> SEQUENCE: 152
cccacacagc aaagcagaaa c                                               21

<210> SEQ ID NO 153
<211> LENGTH: 23
<212> TYPE: DNA
<213> ORGANISM: Artificial Sequence
<220> FEATURE:
<223> OTHER INFORMATION: synthetic construct

<400> SEQUENCE: 153
agccacctcc ttactttgcc tcc                                             23
```

<210> SEQ ID NO 154
<211> LENGTH: 25
<212> TYPE: DNA
<213> ORGANISM: Artificial Sequence
<220> FEATURE:
<223> OTHER INFORMATION: synthetic construct

<400> SEQUENCE: 154
gtctttgtgt tcccggacat agtcc                                              25

<210> SEQ ID NO 155
<211> LENGTH: 25
<212> TYPE: DNA
<213> ORGANISM: Artificial Sequence
<220> FEATURE:
<223> OTHER INFORMATION: synthetic construct

<400> SEQUENCE: 155
tgaaggtgcc atcattcttg aggag                                              25

<210> SEQ ID NO 156
<211> LENGTH: 24
<212> TYPE: DNA
<213> ORGANISM: Artificial Sequence
<220> FEATURE:
<223> OTHER INFORMATION: synthetic construct

<400> SEQUENCE: 156
gaagtgtcga agacagctgg tgaa                                               24

<210> SEQ ID NO 157
<211> LENGTH: 24
<212> TYPE: DNA
<213> ORGANISM: Artificial Sequence
<220> FEATURE:
<223> OTHER INFORMATION: synthetic construct

<400> SEQUENCE: 157
cagcttgctt aggtccactc tctc                                               24

<210> SEQ ID NO 158
<211> LENGTH: 21
<212> TYPE: DNA
<213> ORGANISM: Artificial Sequence
<220> FEATURE:
<223> OTHER INFORMATION: synthetic construct

<400> SEQUENCE: 158
gggcttgtcc atgcggtggc c                                                  21

<210> SEQ ID NO 159
<211> LENGTH: 22
<212> TYPE: DNA
<213> ORGANISM: Artificial Sequence
<220> FEATURE:
<223> OTHER INFORMATION: synthetic construct

<400> SEQUENCE: 159
ctccacgtcg ctgcccagca cc                                                 22

<210> SEQ ID NO 160
<211> LENGTH: 23
<212> TYPE: DNA
<213> ORGANISM: Artificial Sequence
<220> FEATURE:
<223> OTHER INFORMATION: synthetic construct

<400> SEQUENCE: 160
cagccgccac caccaggatg aac                                    23

<210> SEQ ID NO 161
<211> LENGTH: 26
<212> TYPE: DNA
<213> ORGANISM: Artificial Sequence
<220> FEATURE:
<223> OTHER INFORMATION: synthetic construct

<400> SEQUENCE: 161
cctattaaag cagtgctcat gattgg                                 26

<210> SEQ ID NO 162
<211> LENGTH: 23
<212> TYPE: DNA
<213> ORGANISM: Artificial Sequence
<220> FEATURE:
<223> OTHER INFORMATION: synthetic construct

<400> SEQUENCE: 162
ctttccaaag ccatccactt cac                                    23

<210> SEQ ID NO 163
<211> LENGTH: 24
<212> TYPE: DNA
<213> ORGANISM: Artificial Sequence
<220> FEATURE:
<223> OTHER INFORMATION: synthetic construct

<400> SEQUENCE: 163
gagtccagca cctccttcac cttg                                   24

<210> SEQ ID NO 164
<211> LENGTH: 20
<212> TYPE: DNA
<213> ORGANISM: Artificial Sequence
<220> FEATURE:
<223> OTHER INFORMATION: synthetic construct

<400> SEQUENCE: 164
cgccagactc accgggcacc                                        20

<210> SEQ ID NO 165
<211> LENGTH: 34
<212> TYPE: DNA
<213> ORGANISM: Artificial Sequence
<220> FEATURE:
<223> OTHER INFORMATION: synthetic construct

<400> SEQUENCE: 165
gtcacatttt cattattttt attataaggc ctgc                        34

<210> SEQ ID NO 166
<211> LENGTH: 31
<212> TYPE: DNA
<213> ORGANISM: Artificial Sequence
<220> FEATURE:
<223> OTHER INFORMATION: synthetic construct

<400> SEQUENCE: 166
gtattattta tggcaaatac acaaagaaag c                           31

<210> SEQ ID NO 167

```
<210> SEQ ID NO 167
<211> LENGTH: 25
<212> TYPE: DNA
<213> ORGANISM: Artificial Sequence
<220> FEATURE:
<223> OTHER INFORMATION: synthetic construct

<400> SEQUENCE: 167
gatgtggctc gccaattaac cctga                                    25

<210> SEQ ID NO 168
<211> LENGTH: 28
<212> TYPE: DNA
<213> ORGANISM: Artificial Sequence
<220> FEATURE:
<223> OTHER INFORMATION: synthetic construct

<400> SEQUENCE: 168
cttgctatta ttgatggcaa atacacag                                 28

<210> SEQ ID NO 169
<211> LENGTH: 21
<212> TYPE: DNA
<213> ORGANISM: Artificial Sequence
<220> FEATURE:
<223> OTHER INFORMATION: synthetic construct

<400> SEQUENCE: 169
gggcaggaga ccctgtagga g                                        21

<210> SEQ ID NO 170
<211> LENGTH: 26
<212> TYPE: DNA
<213> ORGANISM: Artificial Sequence
<220> FEATURE:
<223> OTHER INFORMATION: synthetic construct

<400> SEQUENCE: 170
caaaagactt ggtgttgttg atggca                                   26

<210> SEQ ID NO 171
<211> LENGTH: 29
<212> TYPE: DNA
<213> ORGANISM: Artificial Sequence
<220> FEATURE:
<223> OTHER INFORMATION: synthetic construct

<400> SEQUENCE: 171
agaaaggatt ctttatgttt ctcttcagg                                29

<210> SEQ ID NO 172
<211> LENGTH: 29
<212> TYPE: DNA
<213> ORGANISM: Artificial Sequence
<220> FEATURE:
<223> OTHER INFORMATION: synthetic construct

<400> SEQUENCE: 172
gagattccaa taactgttgt tctctttgt                                29

<210> SEQ ID NO 173
<211> LENGTH: 23
<212> TYPE: DNA
<213> ORGANISM: Artificial Sequence
<220> FEATURE:
<223> OTHER INFORMATION: primer

<400> SEQUENCE: 173
```
cgagacggat caagcagaag acg                                          23

<210> SEQ ID NO 174
<211> LENGTH: 20
<212> TYPE: DNA
<213> ORGANISM: Artificial Sequence
<220> FEATURE:
<223> OTHER INFORMATION: primer

<400> SEQUENCE: 174
gccaactggc caagacctgc                                              20

<210> SEQ ID NO 175
<211> LENGTH: 20
<212> TYPE: DNA
<213> ORGANISM: Artificial Sequence
<220> FEATURE:
<223> OTHER INFORMATION: primer

<400> SEQUENCE: 175
ctccagcccc agctgctcac                                              20

<210> SEQ ID NO 176
<211> LENGTH: 22
<212> TYPE: DNA
<213> ORGANISM: Artificial Sequence
<220> FEATURE:
<223> OTHER INFORMATION: primer

<400> SEQUENCE: 176
gtccccaggc ctctgattcc tc                                           22

<210> SEQ ID NO 177
<211> LENGTH: 21
<212> TYPE: DNA
<213> ORGANISM: Artificial Sequence
<220> FEATURE:
<223> OTHER INFORMATION: primer

<400> SEQUENCE: 177
cctcccagag accccagttg c                                            21

<210> SEQ ID NO 178
<211> LENGTH: 25
<212> TYPE: DNA
<213> ORGANISM: Artificial Sequence
<220> FEATURE:
<223> OTHER INFORMATION: primer

<400> SEQUENCE: 178
tgggcctgtg ttatctccta ggttg                                        25

<210> SEQ ID NO 179
<211> LENGTH: 20
<212> TYPE: DNA
<213> ORGANISM: Artificial Sequence
<220> FEATURE:
<223> OTHER INFORMATION: primer

<400> SEQUENCE: 179
gcagctcgtg gtgaggctcc                                              20

<210> SEQ ID NO 180
<211> LENGTH: 32
<212> TYPE: DNA

```
<213> ORGANISM: Artificial Sequence
<220> FEATURE:
<223> OTHER INFORMATION: primer

<400> SEQUENCE: 180
agaaacagag aatctccatt ttagcactta cc                                    32

<210> SEQ ID NO 181
<211> LENGTH: 30
<212> TYPE: DNA
<213> ORGANISM: Artificial Sequence
<220> FEATURE:
<223> OTHER INFORMATION: primer

<400> SEQUENCE: 181
ttcaatgcat gctgtttaat tgtgtggaag                                       30

<210> SEQ ID NO 182
<211> LENGTH: 28
<212> TYPE: DNA
<213> ORGANISM: Artificial Sequence
<220> FEATURE:
<223> OTHER INFORMATION: primer

<400> SEQUENCE: 182
tccacaaaat ggatccagac aactgttc                                         28

<210> SEQ ID NO 183
<211> LENGTH: 20
<212> TYPE: DNA
<213> ORGANISM: Artificial Sequence
<220> FEATURE:
<223> OTHER INFORMATION: primer

<400> SEQUENCE: 183
ggcgccggta gttgcccttc                                                  20

<210> SEQ ID NO 184
<211> LENGTH: 26
<212> TYPE: DNA
<213> ORGANISM: Artificial Sequence
<220> FEATURE:
<223> OTHER INFORMATION: primer

<400> SEQUENCE: 184
ggaagttgac tttgtccacc tggaac                                           26

<210> SEQ ID NO 185
<211> LENGTH: 26
<212> TYPE: DNA
<213> ORGANISM: Artificial Sequence
<220> FEATURE:
<223> OTHER INFORMATION: primer

<400> SEQUENCE: 185
ggaggtatcc acatcctctt cctcag                                           26

<210> SEQ ID NO 186
<211> LENGTH: 23
<212> TYPE: DNA
<213> ORGANISM: Artificial Sequence
<220> FEATURE:
<223> OTHER INFORMATION: primer

<400> SEQUENCE: 186
cgactcccag gtacttccgg aac                                              23
```

<210> SEQ ID NO 187
<211> LENGTH: 24
<212> TYPE: DNA
<213> ORGANISM: Artificial Sequence
<220> FEATURE:
<223> OTHER INFORMATION: primer

<400> SEQUENCE: 187
tgtcaacggt cgctcatcta cctc                                              24

<210> SEQ ID NO 188
<211> LENGTH: 26
<212> TYPE: DNA
<213> ORGANISM: Artificial Sequence
<220> FEATURE:
<223> OTHER INFORMATION: primer

<400> SEQUENCE: 188
ccatagaaat ctagggcctc ttgtgc                                            26

<210> SEQ ID NO 189
<211> LENGTH: 22
<212> TYPE: DNA
<213> ORGANISM: Artificial Sequence
<220> FEATURE:
<223> OTHER INFORMATION: primer

<400> SEQUENCE: 189
caccacacac aggtaacggc tg                                                22

<210> SEQ ID NO 190
<211> LENGTH: 30
<212> TYPE: DNA
<213> ORGANISM: Artificial Sequence
<220> FEATURE:
<223> OTHER INFORMATION: primer

<400> SEQUENCE: 190
gaaatatcct ccttactcat ggtcggatca                                        30

<210> SEQ ID NO 191
<211> LENGTH: 30
<212> TYPE: DNA
<213> ORGANISM: Artificial Sequence
<220> FEATURE:
<223> OTHER INFORMATION: primer

<400> SEQUENCE: 191
cccatttgtg atcataagga agttgtgttg                                        30

<210> SEQ ID NO 192
<211> LENGTH: 22
<212> TYPE: DNA
<213> ORGANISM: Artificial Sequence
<220> FEATURE:
<223> OTHER INFORMATION: primer

<400> SEQUENCE: 192
gtgggctctg ggaatcctgc tg                                                22

<210> SEQ ID NO 193
<211> LENGTH: 24
<212> TYPE: DNA
<213> ORGANISM: Artificial Sequence
<220> FEATURE:

<223> OTHER INFORMATION: primer

<400> SEQUENCE: 193
ccacacagca aagcagaaac tcac                                          24

<210> SEQ ID NO 194
<211> LENGTH: 25
<212> TYPE: DNA
<213> ORGANISM: Artificial Sequence
<220> FEATURE:
<223> OTHER INFORMATION: primer

<400> SEQUENCE: 194
acctccttac tttgcctcct tctgc                                         25

<210> SEQ ID NO 195
<211> LENGTH: 24
<212> TYPE: DNA
<213> ORGANISM: Artificial Sequence
<220> FEATURE:
<223> OTHER INFORMATION: primer

<400> SEQUENCE: 195
gtgttcccgg acatagtcca ggag                                          24

<210> SEQ ID NO 196
<211> LENGTH: 26
<212> TYPE: DNA
<213> ORGANISM: Artificial Sequence
<220> FEATURE:
<223> OTHER INFORMATION: primer

<400> SEQUENCE: 196
gccatcattc ttgaggagga agtagc                                        26

<210> SEQ ID NO 197
<211> LENGTH: 26
<212> TYPE: DNA
<213> ORGANISM: Artificial Sequence
<220> FEATURE:
<223> OTHER INFORMATION: primer

<400> SEQUENCE: 197
agacagctgg tgaaaaatcc ctgaac                                        26

<210> SEQ ID NO 198
<211> LENGTH: 28
<212> TYPE: DNA
<213> ORGANISM: Artificial Sequence
<220> FEATURE:
<223> OTHER INFORMATION: primer

<400> SEQUENCE: 198
tgcttaggtc cactctctct cttttcag                                      28

<210> SEQ ID NO 199
<211> LENGTH: 21
<212> TYPE: DNA
<213> ORGANISM: Artificial Sequence
<220> FEATURE:
<223> OTHER INFORMATION: primer

<400> SEQUENCE: 199
gcggtggccc tccttcagca g                                             21

```
<210> SEQ ID NO 200
<211> LENGTH: 20
<212> TYPE: DNA
<213> ORGANISM: Artificial Sequence
<220> FEATURE:
<223> OTHER INFORMATION: primer

<400> SEQUENCE: 200
ccagcaccgc cgtctggttg                                                 20

<210> SEQ ID NO 201
<211> LENGTH: 24
<212> TYPE: DNA
<213> ORGANISM: Artificial Sequence
<220> FEATURE:
<223> OTHER INFORMATION: primer

<400> SEQUENCE: 201
ccaccaggat gaacaggaag aagc                                            24

<210> SEQ ID NO 202
<211> LENGTH: 22
<212> TYPE: DNA
<213> ORGANISM: Artificial Sequence
<220> FEATURE:
<223> OTHER INFORMATION: primer

<400> SEQUENCE: 202
cagtgctcat gattgggtcc gt                                              22

<210> SEQ ID NO 203
<211> LENGTH: 21
<212> TYPE: DNA
<213> ORGANISM: Artificial Sequence
<220> FEATURE:
<223> OTHER INFORMATION: primer

<400> SEQUENCE: 203
gccatccact tcactggcag c                                               21

<210> SEQ ID NO 204
<211> LENGTH: 24
<212> TYPE: DNA
<213> ORGANISM: Artificial Sequence
<220> FEATURE:
<223> OTHER INFORMATION: primer

<400> SEQUENCE: 204
cttcaccttg ccgtaagagc cttc                                            24

<210> SEQ ID NO 205
<211> LENGTH: 21
<212> TYPE: DNA
<213> ORGANISM: Artificial Sequence
<220> FEATURE:
<223> OTHER INFORMATION: primer

<400> SEQUENCE: 205
ctcaccgggc accgtgaagt c                                               21

<210> SEQ ID NO 206
<211> LENGTH: 37
<212> TYPE: DNA
<213> ORGANISM: Artificial Sequence
<220> FEATURE:
<223> OTHER INFORMATION: primer
```

```
<400> SEQUENCE: 206
cattattttt attataaggc ctgctgaaaa tgactga                       37

<210> SEQ ID NO 207
<211> LENGTH: 26
<212> TYPE: DNA
<213> ORGANISM: Artificial Sequence
<220> FEATURE:
<223> OTHER INFORMATION: primer

<400> SEQUENCE: 207
tggcaaatac acaaagaaag ccctcc                                   26

<210> SEQ ID NO 208
<211> LENGTH: 30
<212> TYPE: DNA
<213> ORGANISM: Artificial Sequence
<220> FEATURE:
<223> OTHER INFORMATION: primer

<400> SEQUENCE: 208
caattaaccc tgattactgg tttccaacag                               30

<210> SEQ ID NO 209
<211> LENGTH: 25
<212> TYPE: DNA
<213> ORGANISM: Artificial Sequence
<220> FEATURE:
<223> OTHER INFORMATION: primer

<400> SEQUENCE: 209
ggcaaataca cagaggaagc cttcg                                    25

<210> SEQ ID NO 210
<211> LENGTH: 22
<212> TYPE: DNA
<213> ORGANISM: Artificial Sequence
<220> FEATURE:
<223> OTHER INFORMATION: primer

<400> SEQUENCE: 210
caggagaccc tgtaggagga cc                                       22

<210> SEQ ID NO 211
<211> LENGTH: 24
<212> TYPE: DNA
<213> ORGANISM: Artificial Sequence
<220> FEATURE:
<223> OTHER INFORMATION: primer

<400> SEQUENCE: 211
tgatggcaaa cacacacagg aagc                                     24

<210> SEQ ID NO 212
<211> LENGTH: 31
<212> TYPE: DNA
<213> ORGANISM: Artificial Sequence
<220> FEATURE:
<223> OTHER INFORMATION: primer

<400> SEQUENCE: 212
aggattcttt atgtttctct tcaggcaact g                             31

<210> SEQ ID NO 213
<211> LENGTH: 28
```

```
<212> TYPE: DNA
<213> ORGANISM: Artificial Sequence
<220> FEATURE:
<223> OTHER INFORMATION: primer

<400> SEQUENCE: 213
actgttgttc tctttgttgg agtgcatc                                              28

<210> SEQ ID NO 214
<211> LENGTH: 23
<212> TYPE: DNA
<213> ORGANISM: Artificial Sequence
<220> FEATURE:
<223> OTHER INFORMATION: synthetic construct

<400> SEQUENCE: 214
cgagacggat caagcagaag acg                                                   23

<210> SEQ ID NO 215
<211> LENGTH: 61
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (35)..(42)
<223> OTHER INFORMATION: this stretch nnnnnnnn represents any one of the
      96 barcode sequences defined in Table 6
<220> FEATURE:
<221> NAME/KEY: misc_feature
<222> LOCATION: (43)..(48)
<223> OTHER INFORMATION: n is a, c, g, or t

<400> SEQUENCE: 215
cgagacggat caagcagaag acggcatacg agatnnnnnn nnnnnnnngt gactggagtt           60
c                                                                           61

<210> SEQ ID NO 216
<211> LENGTH: 78
<212> TYPE: DNA
<213> ORGANISM: Artificial Sequence
<220> FEATURE:
<223> OTHER INFORMATION: synthetic construct

<400> SEQUENCE: 216
atcggaagag cacacgtctg aactccagtc acaaaaaaaa aaaaatctcg tatgccgtct           60
tctgcttgat ccgtctcg                                                         78

<210> SEQ ID NO 217
<211> LENGTH: 23
<212> TYPE: DNA
<213> ORGANISM: Artificial Sequence
<220> FEATURE:
<223> OTHER INFORMATION: primer

<400> SEQUENCE: 217
caagcagaag acggcatacg aga                                                   23

<210> SEQ ID NO 218
<211> LENGTH: 87
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
```

<222> LOCATION: (59)..(62)
<223> OTHER INFORMATION: n is a, c, g, or t

<400> SEQUENCE: 218
aatgatacgg cgaccaccga gatctacact ctttccctac acgacgctct tccgatctnn    60
nnacttgcag ctgtgggttg attccac                                        87

<210> SEQ ID NO 219
<211> LENGTH: 88
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 219
aatgatacgg cgaccaccga gatctacact ctttccctac acgacgctct tccgatctnn    60
nnactccagc tgctcaccat cgctatct                                       88

<210> SEQ ID NO 220
<211> LENGTH: 91
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 220
aatgatacgg cgaccaccga gatctacact ctttccctac acgacgctct tccgatctnn    60
nnacttcctc actgattgct cttaggtctg g                                   91

<210> SEQ ID NO 221
<211> LENGTH: 87
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 221
aatgatacgg cgaccaccga gatctacact ctttccctac acgacgctct tccgatctnn    60
nnactcaaac cagacctcag gcggctc                                        87

<210> SEQ ID NO 222
<211> LENGTH: 88
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 222
aatgatacgg cgaccaccga gatctacact ctttccctac acgacgctct tccgatctnn    60
nnactgctct gactgtacca ccatccac 88

<210> SEQ ID NO 223
<211> LENGTH: 89
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 223
aatgatacgg cgaccaccga gatctacact ctttccctac acgacgctct tccgatctnn 60
nnacttcccc tttcttgcgg agattctct 89

<210> SEQ ID NO 224
<211> LENGTH: 96
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 224
aatgatacgg cgaccaccga gatctacact ctttccctac acgacgctct tccgatctnn 60
nnactcactt acctgtgact ccatagaaaa tctttc 96

<210> SEQ ID NO 225
<211> LENGTH: 94
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 225
aatgatacgg cgaccaccga gatctacact ctttccctac acgacgctct tccgatctnn 60
nnactgaaga tccaatccat ttttgttgtc cagc 94

<210> SEQ ID NO 226
<211> LENGTH: 89
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 226
aatgatacgg cgaccaccga gatctacact ctttccctac acgacgctct tccgatctnn 60
nnactcaaac tgatgggacc cactccatc 89

<210> SEQ ID NO 227
<211> LENGTH: 89
<212> TYPE: DNA
<213> ORGANISM: Artificial Sequence

```
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 227
aatgatacgg cgaccaccga gatctacact ctttccctac acgacgctct tccgatctnn    60
nnactcggta gttgcccttc tcgaacatg                                      89

<210> SEQ ID NO 228
<211> LENGTH: 93
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 228
aatgatacgg cgaccaccga gatctacact ctttccctac acgacgctct tccgatctnn    60
nnactacttg gtctcaaaga ttccagaagt cag                                 93

<210> SEQ ID NO 229
<211> LENGTH: 90
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 229
aatgatacgg cgaccaccga gatctacact ctttccctac acgacgctct tccgatctnn    60
nnactcctca ggattgcctt taccactcag                                     90

<210> SEQ ID NO 230
<211> LENGTH: 89
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 230
aatgatacgg cgaccaccga gatctacact ctttccctac acgacgctct tccgatctnn    60
nnactccgga acctgtgctc agatgacac                                      89

<210> SEQ ID NO 231
<211> LENGTH: 91
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t
```

<400> SEQUENCE: 231
aatgatacgg cgaccaccga gatctacact ctttccctac acgacgctct tccgatctnn    60
nnactctgtg aacttgtcag ccaccatgta g                                    91

<210> SEQ ID NO 232
<211> LENGTH: 99
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 232
aatgatacgg cgaccaccga gatctacact ctttccctac acgacgctct tccgatctnn    60
nnactccttt aaaaatttgc cccgatgtaa taaatatgc                            99

<210> SEQ ID NO 233
<211> LENGTH: 92
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 233
aatgatacgg cgaccaccga gatctacact ctttccctac acgacgctct tccgatctnn    60
nnactggctg agggaactca aagtacatga ac                                   92

<210> SEQ ID NO 234
<211> LENGTH: 96
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 234
aatgatacgg cgaccaccga gatctacact ctttccctac acgacgctct tccgatctnn    60
nnactggatc acaaagattt gtgattttgg tctagc                               96

<210> SEQ ID NO 235
<211> LENGTH: 98
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 235
aatgatacgg cgaccaccga gatctacact ctttccctac acgacgctct tccgatctnn    60
nnactggtct atgtaaacat aattgtttcc atttatct                             98

```
<210> SEQ ID NO 236
<211> LENGTH: 86
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 236
aatgatacgg cgaccaccga gatctacact ctttccctac acgacgctct tccgatctnn    60
nnactgccac acattggagc atgcca                                         86

<210> SEQ ID NO 237
<211> LENGTH: 93
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 237
aatgatacgg cgaccaccga gatctacact ctttccctac acgacgctct tccgatctnn    60
nnactgaaac tcacatcgag gatttccttg ttg                                 93

<210> SEQ ID NO 238
<211> LENGTH: 91
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 238
aatgatacgg cgaccaccga gatctacact ctttccctac acgacgctct tccgatctnn    60
nnacttgcat ggtattcttt ctcttccgca c                                   91

<210> SEQ ID NO 239
<211> LENGTH: 86
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 239
aatgatacgg cgaccaccga gatctacact ctttccctac acgacgctct tccgatctnn    60
nnactgaggc agccgaaggg catgag                                         86

<210> SEQ ID NO 240
<211> LENGTH: 85
<212> TYPE: DNA
<213> ORGANISM: Artificial Sequence
<220> FEATURE:
<223> OTHER INFORMATION: synthetic construct
<220> FEATURE:
```

<221> NAME/KEY: misc_feature
<222> LOCATION: (59)..(62)
<223> OTHER INFORMATION: n is a, c, g, or t

<400> SEQUENCE: 240
aatgatacgg cgaccaccga gatctacact ctttccctac acgacgctct tccgatctnn    60
nnactgtggc cgccaggtct tgatg                                          85

<210> SEQ ID NO 241
<211> LENGTH: 96
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 241
aatgatacgg cgaccaccga gatctacact ctttccctac acgacgctct tccgatctnn    60
nnactcatgt gtagaaagca gatttctcca tgattc                              96

<210> SEQ ID NO 242
<211> LENGTH: 95
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 242
aatgatacgg cgaccaccga gatctacact ctttccctac acgacgctct tccgatctnn    60
nnactttcag cagtaggtgc tttattttta ggtac                               95

<210> SEQ ID NO 243
<211> LENGTH: 88
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 243
aatgatacgg cgaccaccga gatctacact ctttccctac acgacgctct tccgatctnn    60
nnactcagct tgaagagctc ctccacag                                       88

<210> SEQ ID NO 244
<211> LENGTH: 84
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 244
aatgatacgg cgaccaccga gatctacact ctttccctac acgacgctct tccgatctnn    60

-continued nnactcctgc aggatgggcc ggtg                                              84

<210> SEQ ID NO 245
<211> LENGTH: 86
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 245
aatgatacgg cgaccaccga gatctacact ctttccctac acgacgctct tccgatctnn      60
nnactccacc ccgtagctga ggatgc                                            86

<210> SEQ ID NO 246
<211> LENGTH: 94
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 246
aatgatacgg cgaccaccga gatctacact ctttccctac acgacgctct tccgatctnn      60
nnactgctgg agacatctca cattgttttt gttg                                   94

<210> SEQ ID NO 247
<211> LENGTH: 92
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 247
aatgatacgg cgaccaccga gatctacact ctttccctac acgacgctct tccgatctnn      60
nnactgcttt gcacctgttt tgttgtgtac ac                                     92

<210> SEQ ID NO 248
<211> LENGTH: 88
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 248
aatgatacgg cgaccaccga gatctacact ctttccctac acgacgctct tccgatctnn      60
nnactcccat caggtacttg ccgatgag                                          88

<210> SEQ ID NO 249
<211> LENGTH: 93
<212> TYPE: DNA

```
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 249
aatgatacgg cgaccaccga gatctacact ctttccctac acgacgctct tccgatctnn    60
nnactctgag tgtagatgat gtcatcctcg atg                                 93

<210> SEQ ID NO 250
<211> LENGTH: 96
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 250
aatgatacgg cgaccaccga gatctacact ctttccctac acgacgctct tccgatctnn    60
nnactgctga aaatgactga atataaactt gtggta                              96

<210> SEQ ID NO 251
<211> LENGTH: 91
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 251
aatgatacgg cgaccaccga gatctacact ctttccctac acgacgctct tccgatctnn    60
nnactcagtc ctcatgtact ggtccctcat t                                   91

<210> SEQ ID NO 252
<211> LENGTH: 92
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 252
aatgatacgg cgaccaccga gatctacact ctttccctac acgacgctct tccgatctnn    60
nnacttcttg ctggtgtgaa atgactgagt ac                                  92

<210> SEQ ID NO 253
<211> LENGTH: 89
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t
```

<400> SEQUENCE: 253
aatgatacgg cgaccaccga gatctacact ctttccctac acgacgctct tccgatctnn    60
nnacttcgcc tgtcctcatg tattggtct                                      89

<210> SEQ ID NO 254
<211> LENGTH: 91
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 254
aatgatacgg cgaccaccga gatctacact ctttccctac acgacgctct tccgatctnn    60
nnactcctga ggagcgatga cggaatataa g                                   91

<210> SEQ ID NO 255
<211> LENGTH: 86
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 255
aatgatacgg cgaccaccga gatctacact ctttccctac acgacgctct tccgatctnn    60
nnactatgta ctggtcccgc atggcg                                         86

<210> SEQ ID NO 256
<211> LENGTH: 96
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 256
aatgatacgg cgaccaccga gatctacact ctttccctac acgacgctct tccgatctnn    60
nnactaggac ttttagaatt cttaaatgtc atccgc                              96

<210> SEQ ID NO 257
<211> LENGTH: 93
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (59)..(62)
<223> OTHER INFORMATION: n is a, c, g, or t

<400> SEQUENCE: 257
aatgatacgg cgaccaccga gatctacact ctttccctac acgacgctct tccgatctnn    60
nnacttctag cttgctggtg tattcttcat agg                                 93

<210> SEQ ID NO 258
<211> LENGTH: 79
<212> TYPE: DNA
<213> ORGANISM: Homo sapiens

<400> SEQUENCE: 258
tgcagctgtg ggttgattcc acaccccgc ccggcacccg cgtccgcgcc atggccatct    60
acaagcagtc acagcacag                                                79

<210> SEQ ID NO 259
<211> LENGTH: 73
<212> TYPE: DNA
<213> ORGANISM: Homo sapiens

<400> SEQUENCE: 259
ccagctgctc accatcgcta tctgagcagc gctcatggtg ggggcagcgc ctcacaacct    60
ccgtcatgtg cta                                                      73

<210> SEQ ID NO 260
<211> LENGTH: 80
<212> TYPE: DNA
<213> ORGANISM: Homo sapiens

<400> SEQUENCE: 260
tcctcactga ttgctcttag gtctggcccc tcctcagcat cttatccgag tggaaggaaa    60
tttgcgtgtg gagtatttgt                                               80

<210> SEQ ID NO 261
<211> LENGTH: 71
<212> TYPE: DNA
<213> ORGANISM: Homo sapiens

<400> SEQUENCE: 261
caaaccagac ctcaggcggc tcatagggca ccaccacact atgtcgaaaa gtgtttctgt    60
catccaaata t                                                        71

<210> SEQ ID NO 262
<211> LENGTH: 93
<212> TYPE: DNA
<213> ORGANISM: Homo sapiens

<400> SEQUENCE: 262
gctctgactg taccaccatc cactacaact acatgtgtaa cagttcctgc atgggcggca    60
tgaaccggag gcccatcctc accatcatca cag                                93

<210> SEQ ID NO 263
<211> LENGTH: 89
<212> TYPE: DNA
<213> ORGANISM: Homo sapiens

<400> SEQUENCE: 263
tcccctttct tgcggagatt ctcttcctct gtgcgccggt ctctcccagg acaggcacaa    60
acacgcacct caaagctgtt ccgtcccag                                     89

<210> SEQ ID NO 264
<211> LENGTH: 76
<212> TYPE: DNA
<213> ORGANISM: Homo sapiens

<400> SEQUENCE: 264

```
cacttacctg tgactccata gaaaatcttt ctcctgctca gtgatttcag agagaggatc    60
tcgtgtagaa attgca                                                   76

<210> SEQ ID NO 265
<211> LENGTH: 75
<212> TYPE: DNA
<213> ORGANISM: Homo sapiens

<400> SEQUENCE: 265
gaagatccaa tccattttg ttgtccagcc accatgatgt gcatcattca tttgtttcat    60
gaaatactcc aaaga                                                   75

<210> SEQ ID NO 266
<211> LENGTH: 68
<212> TYPE: DNA
<213> ORGANISM: Homo sapiens

<400> SEQUENCE: 266
caaactgatg ggacccactc catcgagatt tcactgtagc tagaccaaaa tcacctattt    60
ttactgtt                                                           68

<210> SEQ ID NO 267
<211> LENGTH: 59
<212> TYPE: DNA
<213> ORGANISM: Homo sapiens

<400> SEQUENCE: 267
cggtagttgc ccttctcgaa catgtcttcg caggccgggt ccagcgtcca gtagttgca    59

<210> SEQ ID NO 268
<211> LENGTH: 65
<212> TYPE: DNA
<213> ORGANISM: Homo sapiens

<400> SEQUENCE: 268
acttggtctc aaagattcca gaagtcagga cacggcagcg aagcaggtcc tgaaacaaaa    60
ttgag                                                              65

<210> SEQ ID NO 269
<211> LENGTH: 89
<212> TYPE: DNA
<213> ORGANISM: Homo sapiens

<400> SEQUENCE: 269
cctcaggatt gcctttacca ctcagagaag gagctgtggt agtggcacca gaatggattc    60
cagagtccag gtaagactgt tgctgccag                                    89

<210> SEQ ID NO 270
<211> LENGTH: 61
<212> TYPE: DNA
<213> ORGANISM: Homo sapiens

<400> SEQUENCE: 270
ccggaacctg tgctcagatg acacccccat ggtgcggcgg gccgcagcct ccaagctggg    60
t                                                                  61

<210> SEQ ID NO 271
<211> LENGTH: 61
<212> TYPE: DNA
```

<213> ORGANISM: Homo sapiens

<400> SEQUENCE: 271
ctgtgaactt gtcagccacc atgtagcgga cgcgccagga cttgtcttca gcggcctggc   60
t                                                                  61

<210> SEQ ID NO 272
<211> LENGTH: 83
<212> TYPE: DNA
<213> ORGANISM: Homo sapiens

<400> SEQUENCE: 272
cctttaaaaa tttgccccga tgtaataaat atgcacatat cattacacca gttcgtccct   60
ttccagcttt acagtgaatt gcc                                          83

<210> SEQ ID NO 273
<211> LENGTH: 74
<212> TYPE: DNA
<213> ORGANISM: Homo sapiens

<400> SEQUENCE: 273
ggctgaggga actcaaagta catgaacttg tcttcccgtc gtgtgggtcc tgaattggag   60
gaatatatct tcat                                                    74

<210> SEQ ID NO 274
<211> LENGTH: 76
<212> TYPE: DNA
<213> ORGANISM: Homo sapiens

<400> SEQUENCE: 274
ggatcacaaa gatttgtgat tttggtctag ccagagacat caagaatgat tctaattatg   60
tggttaaagg aaacgc                                                  76

<210> SEQ ID NO 275
<211> LENGTH: 91
<212> TYPE: DNA
<213> ORGANISM: Homo sapiens

<400> SEQUENCE: 275
ggtctatgta aacataattg tttccattta tctcctcaac aaccttccac tgtacttcat   60
acatgggttt ctgtggggag aaagggaaaa c                                 91

<210> SEQ ID NO 276
<211> LENGTH: 68
<212> TYPE: DNA
<213> ORGANISM: Homo sapiens

<400> SEQUENCE: 276
gccacacatt ggagcatgcc attcacgagc ctgtcgtaag tcaggatttc tggttttgct   60
acaggaac                                                           68

<210> SEQ ID NO 277
<211> LENGTH: 91
<212> TYPE: DNA
<213> ORGANISM: Homo sapiens

<400> SEQUENCE: 277
gaaactcaca tcgaggattt ccttgttggc tttcggagat gttgcttctc ttaattcctt   60
gatagcgacg ggaattttaa ctttctcacc g                                 91

<210> SEQ ID NO 278
<211> LENGTH: 69
<212> TYPE: DNA
<213> ORGANISM: Homo sapiens

<400> SEQUENCE: 278
tgcatggtat tctttctctt ccgcacccag cagtttggcc agcccaaaat ctgtgatctt     60
gacatgctt                                                             69

<210> SEQ ID NO 279
<211> LENGTH: 51
<212> TYPE: DNA
<213> ORGANISM: Homo sapiens

<400> SEQUENCE: 279
gaggcagccg aagggcatga gctgcgtgat gagctgcacg gtggaggtga g              51

<210> SEQ ID NO 280
<211> LENGTH: 47
<212> TYPE: DNA
<213> ORGANISM: Homo sapiens

<400> SEQUENCE: 280
gtggccgcca ggtcttgatg tactccccta cagacgtgcg ggtggtc                   47

<210> SEQ ID NO 281
<211> LENGTH: 74
<212> TYPE: DNA
<213> ORGANISM: Homo sapiens

<400> SEQUENCE: 281
catgtgtaga aagcagattt ctccatgatt catttgtatc ttggagtaaa atatcatgaa     60
tcaagtatgg aaga                                                       74

<210> SEQ ID NO 282
<211> LENGTH: 62
<212> TYPE: DNA
<213> ORGANISM: Homo sapiens

<400> SEQUENCE: 282
ttcagcagta ggtgctttat ttttaggtac ttctcgcttg gtttgagctg tttgaggagg     60
tc                                                                    62

<210> SEQ ID NO 283
<211> LENGTH: 67
<212> TYPE: DNA
<213> ORGANISM: Homo sapiens

<400> SEQUENCE: 283
cagcttgaag agctcctcca cagggatgcc ggggtacggg gagcccccca gcgtgaagat     60
ctcccat                                                               67

<210> SEQ ID NO 284
<211> LENGTH: 56
<212> TYPE: DNA
<213> ORGANISM: Homo sapiens

<400> SEQUENCE: 284
cctgcaggat gggccggtgc ggggagcgct ctgtggggc agatgacgct caggga          56

```
<210> SEQ ID NO 285
<211> LENGTH: 60
<212> TYPE: DNA
<213> ORGANISM: Homo sapiens

<400> SEQUENCE: 285
ccaccccgta gctgaggatg cctgcataca cactgcccgc ctcgtcagcc tccaccagcg     60

<210> SEQ ID NO 286
<211> LENGTH: 71
<212> TYPE: DNA
<213> ORGANISM: Homo sapiens

<400> SEQUENCE: 286
gctggagaca tctcacattg tttttgttga cgatcttgtt gaagaagtcg ttgacatatt     60
tgatagggaa c                                                         71

<210> SEQ ID NO 287
<211> LENGTH: 70
<212> TYPE: DNA
<213> ORGANISM: Homo sapiens

<400> SEQUENCE: 287
gctttgcacc tgttttgttg tgtacactat agtattcttt atcatacatg tctctggcaa     60
gaccaaaatt                                                           70

<210> SEQ ID NO 288
<211> LENGTH: 72
<212> TYPE: DNA
<213> ORGANISM: Homo sapiens

<400> SEQUENCE: 288
cccatcaggt acttgccgat gagcttggcc cgcttgcggc gcggctggta gatgacctcg     60
gtggagtcga ta                                                        72

<210> SEQ ID NO 289
<211> LENGTH: 76
<212> TYPE: DNA
<213> ORGANISM: Homo sapiens

<400> SEQUENCE: 289
ctgagtgtag atgatgtcat cctcgatgtc gaagaggtcc tcgtcctcgt ccgcgccgtg     60
caggtcctcc aagtat                                                    76

<210> SEQ ID NO 290
<211> LENGTH: 69
<212> TYPE: DNA
<213> ORGANISM: Homo sapiens

<400> SEQUENCE: 290
gctgaaaatg actgaatata aacttgtggt agttggagct ggtggcgtag gcaagagtgc     60
cttgacgac                                                            69

<210> SEQ ID NO 291
<211> LENGTH: 65
<212> TYPE: DNA
<213> ORGANISM: Homo sapiens

<400> SEQUENCE: 291
cagtcctcat gtactggtcc ctcattgcac tgtactcctc ttgacctgct gtgtcgagaa     60
``` tatcg                                                              65

<210> SEQ ID NO 292
<211> LENGTH: 74
<212> TYPE: DNA
<213> ORGANISM: Homo sapiens

<400> SEQUENCE: 292
tcttgctggt gtgaaatgac tgagtacaaa ctggtggtgg ttggagcagg tggtgttggg    60
aaaagcgcac tgat                                                    74

<210> SEQ ID NO 293
<211> LENGTH: 69
<212> TYPE: DNA
<213> ORGANISM: Homo sapiens

<400> SEQUENCE: 293
tcgcctgtcc tcatgtattg gtctctcatg gcactgtact cttcttgtcc agctgtatcc    60
agtatgtca                                                          69

<210> SEQ ID NO 294
<211> LENGTH: 73
<212> TYPE: DNA
<213> ORGANISM: Homo sapiens

<400> SEQUENCE: 294
cctgaggagc gatgacggaa tataagctgg tggtggtggg cgccggcggt gtgggcaaga    60
gtgcgctgac cac                                                     73

<210> SEQ ID NO 295
<211> LENGTH: 55
<212> TYPE: DNA
<213> ORGANISM: Homo sapiens

<400> SEQUENCE: 295
atgtactggt cccgcatggc gctgtactcc tcctggccgg cggtatccag gatga         55

<210> SEQ ID NO 296
<211> LENGTH: 62
<212> TYPE: DNA
<213> ORGANISM: Homo sapiens

<400> SEQUENCE: 296 aggacttttta gaattcttaa atgtcatccg cataggtgtt ttgtcaatat tataaacagg    60
at                                                                 62

<210> SEQ ID NO 297
<211> LENGTH: 75
<212> TYPE: DNA
<213> ORGANISM: Homo sapiens

<400> SEQUENCE: 297
tctagcttgc tggtgtattc ttcataggcc tataaaataa agcagactta tattcaatcc    60
ggactttgtc ctgat                                                   75

<210> SEQ ID NO 298
<211> LENGTH: 37
<212> TYPE: DNA
<213> ORGANISM: Artificial Sequence
<220> FEATURE:

<223> OTHER INFORMATION: synthetic construct

<400> SEQUENCE: 298
agacgtgtgc tcttccgatc tgtgctgtga ctgcttg                    37

<210> SEQ ID NO 299
<211> LENGTH: 38
<212> TYPE: DNA
<213> ORGANISM: Artificial Sequence
<220> FEATURE:
<223> OTHER INFORMATION: synthetic construct

<400> SEQUENCE: 299
agacgtgtgc tcttccgatc tagcacatga cggaggtt                   38

<210> SEQ ID NO 300
<211> LENGTH: 42
<212> TYPE: DNA
<213> ORGANISM: Artificial Sequence
<220> FEATURE:
<223> OTHER INFORMATION: synthetic construct

<400> SEQUENCE: 300
agacgtgtgc tcttccgatc tcaaatactc cacacgcaaa tt              42

<210> SEQ ID NO 301
<211> LENGTH: 42
<212> TYPE: DNA
<213> ORGANISM: Artificial Sequence
<220> FEATURE:
<223> OTHER INFORMATION: synthetic construct

<400> SEQUENCE: 301
agacgtgtgc tcttccgatc tatttggatg acagaaacac tt              42

<210> SEQ ID NO 302
<211> LENGTH: 41
<212> TYPE: DNA
<213> ORGANISM: Artificial Sequence
<220> FEATURE:
<223> OTHER INFORMATION: synthetic construct

<400> SEQUENCE: 302
agacgtgtgc tcttccgatc ttgtgatgat ggtgaggatg g               41

<210> SEQ ID NO 303
<211> LENGTH: 40
<212> TYPE: DNA
<213> ORGANISM: Artificial Sequence
<220> FEATURE:
<223> OTHER INFORMATION: synthetic construct

<400> SEQUENCE: 303
agacgtgtgc tcttccgatc tgggacggaa cagctttgag                 40

<210> SEQ ID NO 304
<211> LENGTH: 44
<212> TYPE: DNA
<213> ORGANISM: Artificial Sequence
<220> FEATURE:
<223> OTHER INFORMATION: synthetic construct

<400> SEQUENCE: 304
agacgtgtgc tcttccgatc tgcaatttct acacgagatc ctct            44

```
<210> SEQ ID NO 305
<211> LENGTH: 48
<212> TYPE: DNA
<213> ORGANISM: Artificial Sequence
<220> FEATURE:
<223> OTHER INFORMATION: synthetic construct

<400> SEQUENCE: 305
agacgtgtgc tcttccgatc tctttggagt atttcatgaa acaaatga          48

<210> SEQ ID NO 306
<211> LENGTH: 48
<212> TYPE: DNA
<213> ORGANISM: Artificial Sequence
<220> FEATURE:
<223> OTHER INFORMATION: synthetic construct

<400> SEQUENCE: 306
agacgtgtgc tcttccgatc tacagtaaaa ataggtgatt ttggtcta          48

<210> SEQ ID NO 307
<211> LENGTH: 41
<212> TYPE: DNA
<213> ORGANISM: Artificial Sequence
<220> FEATURE:
<223> OTHER INFORMATION: synthetic construct

<400> SEQUENCE: 307
agacgtgtgc tcttccgatc tgcaactact ggacgctgga c                 41

<210> SEQ ID NO 308
<211> LENGTH: 43
<212> TYPE: DNA
<213> ORGANISM: Artificial Sequence
<220> FEATURE:
<223> OTHER INFORMATION: synthetic construct

<400> SEQUENCE: 308
agacgtgtgc tcttccgatc tcaattttgt ttcaggacct gct               43

<210> SEQ ID NO 309
<211> LENGTH: 40
<212> TYPE: DNA
<213> ORGANISM: Artificial Sequence
<220> FEATURE:
<223> OTHER INFORMATION: synthetic construct

<400> SEQUENCE: 309
agacgtgtgc tcttccgatc tggcagcaac agtcttacct                   40

<210> SEQ ID NO 310
<211> LENGTH: 38
<212> TYPE: DNA
<213> ORGANISM: Artificial Sequence
<220> FEATURE:
<223> OTHER INFORMATION: synthetic construct

<400> SEQUENCE: 310
agacgtgtgc tcttccgatc tcccagcttg gaggctgc                     38

<210> SEQ ID NO 311
<211> LENGTH: 39
<212> TYPE: DNA
<213> ORGANISM: Artificial Sequence
<220> FEATURE:
<223> OTHER INFORMATION: synthetic construct
```

<400> SEQUENCE: 311
agacgtgtgc tcttccgatc tgccaggccg ctgaagaca        39

<210> SEQ ID NO 312
<211> LENGTH: 45
<212> TYPE: DNA
<213> ORGANISM: Artificial Sequence
<220> FEATURE:
<223> OTHER INFORMATION: synthetic construct

<400> SEQUENCE: 312
agacgtgtgc tcttccgatc tgcaattcac tgtaaagctg gaaag        45

<210> SEQ ID NO 313
<211> LENGTH: 47
<212> TYPE: DNA
<213> ORGANISM: Artificial Sequence
<220> FEATURE:
<223> OTHER INFORMATION: synthetic construct

<400> SEQUENCE: 313
agacgtgtgc tcttccgatc tgaagatata ttcctccaat tcaggac        47

<210> SEQ ID NO 314
<211> LENGTH: 49
<212> TYPE: DNA
<213> ORGANISM: Artificial Sequence
<220> FEATURE:
<223> OTHER INFORMATION: synthetic construct

<400> SEQUENCE: 314
agacgtgtgc tcttccgatc tcgtttcctt taaccacata attagaatc        49

<210> SEQ ID NO 315
<211> LENGTH: 40
<212> TYPE: DNA
<213> ORGANISM: Artificial Sequence
<220> FEATURE:
<223> OTHER INFORMATION: synthetic construct

<400> SEQUENCE: 315
agacgtgtgc tcttccgatc ttttcccttt ctccccacag        40

<210> SEQ ID NO 316
<211> LENGTH: 43
<212> TYPE: DNA
<213> ORGANISM: Artificial Sequence
<220> FEATURE:
<223> OTHER INFORMATION: synthetic construct

<400> SEQUENCE: 316
agacgtgtgc tcttccgatc ttcctgtagc aaaaccagaa atc        43

<210> SEQ ID NO 317
<211> LENGTH: 45
<212> TYPE: DNA
<213> ORGANISM: Artificial Sequence
<220> FEATURE:
<223> OTHER INFORMATION: synthetic construct

<400> SEQUENCE: 317
agacgtgtgc tcttccgatc tggtgagaaa gttaaaattc ccgtc        45

<210> SEQ ID NO 318
<211> LENGTH: 45

<210> SEQ ID NO 318
<211> LENGTH: 45
<212> TYPE: DNA
<213> ORGANISM: Artificial Sequence
<220> FEATURE:
<223> OTHER INFORMATION: synthetic construct

<400> SEQUENCE: 318
agacgtgtgc tcttccgatc tagcatgtca agatcacaga ttttg    45

<210> SEQ ID NO 319
<211> LENGTH: 39
<212> TYPE: DNA
<213> ORGANISM: Artificial Sequence
<220> FEATURE:
<223> OTHER INFORMATION: synthetic construct

<400> SEQUENCE: 319
agacgtgtgc tcttccgatc tcacctccac cgtgcagct    39

<210> SEQ ID NO 320
<211> LENGTH: 38
<212> TYPE: DNA
<213> ORGANISM: Artificial Sequence
<220> FEATURE:
<223> OTHER INFORMATION: synthetic construct

<400> SEQUENCE: 320
agacgtgtgc tcttccgatc taccacccgc acgtctgt    38

<210> SEQ ID NO 321
<211> LENGTH: 50
<212> TYPE: DNA
<213> ORGANISM: Artificial Sequence
<220> FEATURE:
<223> OTHER INFORMATION: synthetic construct

<400> SEQUENCE: 321
agacgtgtgc tcttccgatc tcttccatac ttgattcatg atattttact    50

<210> SEQ ID NO 322
<211> LENGTH: 42
<212> TYPE: DNA
<213> ORGANISM: Artificial Sequence
<220> FEATURE:
<223> OTHER INFORMATION: synthetic construct

<400> SEQUENCE: 322
agacgtgtgc tcttccgatc tacctcctca aacagctcaa ac    42

<210> SEQ ID NO 323
<211> LENGTH: 40
<212> TYPE: DNA
<213> ORGANISM: Artificial Sequence
<220> FEATURE:
<223> OTHER INFORMATION: synthetic construct

<400> SEQUENCE: 323
agacgtgtgc tcttccgatc ttgggagatc ttcacgctgg    40

<210> SEQ ID NO 324
<211> LENGTH: 39
<212> TYPE: DNA
<213> ORGANISM: Artificial Sequence
<220> FEATURE:
<223> OTHER INFORMATION: synthetic construct

<400> SEQUENCE: 324
agacgtgtgc tcttccgatc tccctgagcg tcatctgcc         39

<210> SEQ ID NO 325
<211> LENGTH: 39
<212> TYPE: DNA
<213> ORGANISM: Artificial Sequence
<220> FEATURE:
<223> OTHER INFORMATION: synthetic construct

<400> SEQUENCE: 325
agacgtgtgc tcttccgatc tgctggtgga ggctgacga         39

<210> SEQ ID NO 326
<211> LENGTH: 45
<212> TYPE: DNA
<213> ORGANISM: Artificial Sequence
<220> FEATURE:
<223> OTHER INFORMATION: synthetic construct

<400> SEQUENCE: 326
agacgtgtgc tcttccgatc ttccctatca aatatgtcaa cgact         45

<210> SEQ ID NO 327
<211> LENGTH: 42
<212> TYPE: DNA
<213> ORGANISM: Artificial Sequence
<220> FEATURE:
<223> OTHER INFORMATION: synthetic construct

<400> SEQUENCE: 327
agacgtgtgc tcttccgatc tattttggtc ttgccagaga ca         42

<210> SEQ ID NO 328
<211> LENGTH: 40
<212> TYPE: DNA
<213> ORGANISM: Artificial Sequence
<220> FEATURE:
<223> OTHER INFORMATION: synthetic construct

<400> SEQUENCE: 328
agacgtgtgc tcttccgatc tatcgactcc accgaggtca         40

<210> SEQ ID NO 329
<211> LENGTH: 39
<212> TYPE: DNA
<213> ORGANISM: Artificial Sequence
<220> FEATURE:
<223> OTHER INFORMATION: synthetic construct

<400> SEQUENCE: 329
agacgtgtgc tcttccgatc tacttggagg acctgcacg         39

<210> SEQ ID NO 330
<211> LENGTH: 40
<212> TYPE: DNA
<213> ORGANISM: Artificial Sequence
<220> FEATURE:
<223> OTHER INFORMATION: synthetic construct

<400> SEQUENCE: 330
agacgtgtgc tcttccgatc tcgtcaaggc actcttgcct         40

<210> SEQ ID NO 331
<211> LENGTH: 42
<212> TYPE: DNA
<213> ORGANISM: Artificial Sequence -continued

```
<220> FEATURE:
<223> OTHER INFORMATION: synthetic construct

<400> SEQUENCE: 331
agacgtgtgc tcttccgatc tgatattctc gacacagcag gt                              42

<210> SEQ ID NO 332
<211> LENGTH: 38
<212> TYPE: DNA
<213> ORGANISM: Artificial Sequence
<220> FEATURE:
<223> OTHER INFORMATION: synthetic construct

<400> SEQUENCE: 332
agacgtgtgc tcttccgatc ttcagtgcgc ttttccca                                   38

<210> SEQ ID NO 333
<211> LENGTH: 42
<212> TYPE: DNA
<213> ORGANISM: Artificial Sequence
<220> FEATURE:
<223> OTHER INFORMATION: synthetic construct

<400> SEQUENCE: 333
agacgtgtgc tcttccgatc tgacatactg gatacagctg ga                              42

<210> SEQ ID NO 334
<211> LENGTH: 40
<212> TYPE: DNA
<213> ORGANISM: Artificial Sequence
<220> FEATURE:
<223> OTHER INFORMATION: synthetic construct

<400> SEQUENCE: 334
agacgtgtgc tcttccgatc tggtcagcgc actcttgccc                                 40

<210> SEQ ID NO 335
<211> LENGTH: 40
<212> TYPE: DNA
<213> ORGANISM: Artificial Sequence
<220> FEATURE:
<223> OTHER INFORMATION: synthetic construct

<400> SEQUENCE: 335
agacgtgtgc tcttccgatc tcatcctgga taccgccggc                                 40

<210> SEQ ID NO 336
<211> LENGTH: 48
<212> TYPE: DNA
<213> ORGANISM: Artificial Sequence
<220> FEATURE:
<223> OTHER INFORMATION: synthetic construct

<400> SEQUENCE: 336
agacgtgtgc tcttccgatc tcctgtttat aatattgaca aaacacct                        48

<210> SEQ ID NO 337
<211> LENGTH: 41
<212> TYPE: DNA
<213> ORGANISM: Artificial Sequence
<220> FEATURE:
<223> OTHER INFORMATION: synthetic construct

<400> SEQUENCE: 337
agacgtgtgc tcttccgatc tcaggacaaa gtccggattg a                               41
```

<210> SEQ ID NO 338
<211> LENGTH: 103
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (80)..(85)
<223> OTHER INFORMATION: n is a, c, g, or t

<400> SEQUENCE: 338
cgagacggat caagcagaag acggcatacg agatnnacag ctatgtgact ggagttctag    60
acgtgtgctc ttccgatctn nnnnnctgtg ctgtgactgc ttg                     103

<210> SEQ ID NO 339
<211> LENGTH: 39
<212> TYPE: DNA
<213> ORGANISM: Artificial Sequence
<220> FEATURE:
<223> OTHER INFORMATION: synthetic construct

<400> SEQUENCE: 339 accccccgccc ggcacccgcg tccgcgccat ggccatcta                          39

<210> SEQ ID NO 340
<211> LENGTH: 39
<212> TYPE: DNA
<213> ORGANISM: Artificial Sequence
<220> FEATURE:
<223> OTHER INFORMATION: synthetic construct

<400> SEQUENCE: 340
aaccccgccc ggcacccgcg tccgcgccat ggccatcta                           39

<210> SEQ ID NO 341
<211> LENGTH: 38
<212> TYPE: DNA
<213> ORGANISM: Artificial Sequence
<220> FEATURE:
<223> OTHER INFORMATION: synthetic construct

<400> SEQUENCE: 341
acccccgccc gcacccgcgt ccgcgccatg gccatcta                            38

<210> SEQ ID NO 342
<211> LENGTH: 38
<212> TYPE: DNA
<213> ORGANISM: Artificial Sequence
<220> FEATURE:
<223> OTHER INFORMATION: synthetic construct

<400> SEQUENCE: 342
acccccgccc ggcacccgcg tccgcgccat ggccatca                            38

<210> SEQ ID NO 343
<211> LENGTH: 39
<212> TYPE: DNA
<213> ORGANISM: Artificial Sequence
<220> FEATURE:
<223> OTHER INFORMATION: synthetic construct

<400> SEQUENCE: 343
tcccccgccc ggcacccgcg tccgcgccat ggccatcta         39

<210> SEQ ID NO 344
<211> LENGTH: 38
<212> TYPE: DNA
<213> ORGANISM: Artificial Sequence
<220> FEATURE:
<223> OTHER INFORMATION: synthetic construct

<400> SEQUENCE: 344 accccgccc ggcacccgcg tccgcgccat ggcctcta         38

<210> SEQ ID NO 345
<211> LENGTH: 39
<212> TYPE: DNA
<213> ORGANISM: Artificial Sequence
<220> FEATURE:
<223> OTHER INFORMATION: synthetic construct

<400> SEQUENCE: 345
acccgcgccc ggcacccgcg tccgcgccat ggccaacta         39

<210> SEQ ID NO 346
<211> LENGTH: 38
<212> TYPE: DNA
<213> ORGANISM: Artificial Sequence
<220> FEATURE:
<223> OTHER INFORMATION: synthetic construct

<400> SEQUENCE: 346 accccgccg gcacccgcgt ccgcgccatg gccatcta         38

<210> SEQ ID NO 347
<211> LENGTH: 68
<212> TYPE: DNA
<213> ORGANISM: homo sapiens

<400> SEQUENCE: 347
caaactgatg ggacccactc catcgagatt tcactgtagc tagaccaaaa tcacctattt         60
ttactgtt         68

<210> SEQ ID NO 348
<211> LENGTH: 16
<212> TYPE: DNA
<213> ORGANISM: Artificial Sequence
<220> FEATURE:
<223> OTHER INFORMATION: synthetic construct

<400> SEQUENCE: 348
gagctttcac tgtcgc         16

<210> SEQ ID NO 349
<211> LENGTH: 15
<212> TYPE: DNA
<213> ORGANISM: Artificial Sequence
<220> FEATURE:
<223> OTHER INFORMATION: synthetic construct

<400> SEQUENCE: 349
ggccttcact gtcgc         15

<210> SEQ ID NO 350
<211> LENGTH: 16
<212> TYPE: DNA

```
<213> ORGANISM: Artificial Sequence
<220> FEATURE:
<223> OTHER INFORMATION: synthetic construct

<400> SEQUENCE: 350
aagctttcac tgtcgc                                                    16

<210> SEQ ID NO 351
<211> LENGTH: 16
<212> TYPE: DNA
<213> ORGANISM: Artificial Sequence
<220> FEATURE:
<223> OTHER INFORMATION: synthetic construct

<400> SEQUENCE: 351
gagatttcac tgtcgc                                                    16

<210> SEQ ID NO 352
<211> LENGTH: 16
<212> TYPE: DNA
<213> ORGANISM: Artificial Sequence
<220> FEATURE:
<223> OTHER INFORMATION: synthetic construct

<400> SEQUENCE: 352
aagatttcac tgtagc                                                    16

<210> SEQ ID NO 353
<211> LENGTH: 15
<212> TYPE: DNA
<213> ORGANISM: Artificial Sequence
<220> FEATURE:
<223> OTHER INFORMATION: synthetic construct

<400> SEQUENCE: 353
agctttcact gtcgc                                                     15

<210> SEQ ID NO 354
<211> LENGTH: 16
<212> TYPE: DNA
<213> ORGANISM: Artificial Sequence
<220> FEATURE:
<223> OTHER INFORMATION: synthetic construct

<400> SEQUENCE: 354
gagctctcac tgtcgc                                                    16

<210> SEQ ID NO 355
<211> LENGTH: 16
<212> TYPE: DNA
<213> ORGANISM: Artificial Sequence
<220> FEATURE:
<223> OTHER INFORMATION: synthetic construct

<400> SEQUENCE: 355
gagctttcgc tgtcgc                                                    16

<210> SEQ ID NO 356
<211> LENGTH: 16
<212> TYPE: DNA
<213> ORGANISM: Artificial Sequence
<220> FEATURE:
<223> OTHER INFORMATION: synthetic construct

<400> SEQUENCE: 356
gggctttcac tgtcgc                                                    16
```

<210> SEQ ID NO 357
<211> LENGTH: 16
<212> TYPE: DNA
<213> ORGANISM: Artificial Sequence
<220> FEATURE:
<223> OTHER INFORMATION: synthetic construct

<400> SEQUENCE: 357
gagctttcac tgtagc                                                  16

<210> SEQ ID NO 358
<211> LENGTH: 65
<212> TYPE: DNA
<213> ORGANISM: homo sapiens

<400> SEQUENCE: 358
cagtcctcat gtactggtcc ctcattgcac tgtactcctc ttgacctgct gtgtcgagaa    60
tatcg                                                              65

<210> SEQ ID NO 359
<211> LENGTH: 17
<212> TYPE: DNA
<213> ORGANISM: Artificial Sequence
<220> FEATURE:
<223> OTHER INFORMATION: synthetic construct

<400> SEQUENCE: 359
gcactgtact cctcttg                                                 17

<210> SEQ ID NO 360
<211> LENGTH: 17
<212> TYPE: DNA
<213> ORGANISM: Artificial Sequence
<220> FEATURE:
<223> OTHER INFORMATION: synthetic construct

<400> SEQUENCE: 360
gcacagtact cgtcctg                                                 17

<210> SEQ ID NO 361
<211> LENGTH: 17
<212> TYPE: DNA
<213> ORGANISM: Artificial Sequence
<220> FEATURE:
<223> OTHER INFORMATION: synthetic construct

<400> SEQUENCE: 361
gcaccgtact cctcttg                                                 17

<210> SEQ ID NO 362
<211> LENGTH: 17
<212> TYPE: DNA
<213> ORGANISM: Artificial Sequence
<220> FEATURE:
<223> OTHER INFORMATION: synthetic construct

<400> SEQUENCE: 362
acactgtact cctcttg                                                 17

<210> SEQ ID NO 363
<211> LENGTH: 17
<212> TYPE: DNA
<213> ORGANISM: Artificial Sequence
<220> FEATURE:

<223> OTHER INFORMATION: synthetic construct

<400> SEQUENCE: 363
gcactgtact ccccttg                                                     17

<210> SEQ ID NO 364
<211> LENGTH: 17
<212> TYPE: DNA
<213> ORGANISM: Artificial Sequence
<220> FEATURE:
<223> OTHER INFORMATION: synthetic construct

<400> SEQUENCE: 364
gcactgtact cctctcg                                                     17

<210> SEQ ID NO 365
<211> LENGTH: 17
<212> TYPE: DNA
<213> ORGANISM: Artificial Sequence
<220> FEATURE:
<223> OTHER INFORMATION: synthetic construct

<400> SEQUENCE: 365
gcactgtacc cctcttg                                                     17

<210> SEQ ID NO 366
<211> LENGTH: 16
<212> TYPE: DNA
<213> ORGANISM: Artificial Sequence
<220> FEATURE:
<223> OTHER INFORMATION: synthetic construct

<400> SEQUENCE: 366
gcacagtctc gtcttg                                                      16

<210> SEQ ID NO 367
<211> LENGTH: 17
<212> TYPE: DNA
<213> ORGANISM: Artificial Sequence
<220> FEATURE:
<223> OTHER INFORMATION: synthetic construct

<400> SEQUENCE: 367
gtactgtact cctcttg                                                     17

<210> SEQ ID NO 368
<211> LENGTH: 17
<212> TYPE: DNA
<213> ORGANISM: Artificial Sequence
<220> FEATURE:
<223> OTHER INFORMATION: synthetic construct

<400> SEQUENCE: 368
gcactgtgct cctcttg                                                     17

<210> SEQ ID NO 369
<211> LENGTH: 17
<212> TYPE: DNA
<213> ORGANISM: Artificial Sequence
<220> FEATURE:
<223> OTHER INFORMATION: synthetic construct

<400> SEQUENCE: 369
gcattgtact cttcttg                                                     17

```
<210> SEQ ID NO 370
<211> LENGTH: 17
<212> TYPE: DNA
<213> ORGANISM: Artificial Sequence
<220> FEATURE:
<223> OTHER INFORMATION: synthetic construct

<400> SEQUENCE: 370
gcactgtatt cctcttg                                              17
```